US011685934B2

(12) United States Patent
Walter

(10) Patent No.: US 11,685,934 B2
(45) Date of Patent: Jun. 27, 2023

(54) **METHODS FOR GENOMIC INTEGRATION FOR *KLUYVEROMYCES* HOST CELLS**

(71) Applicant: Amyris, Inc., Emeryville, CA (US)

(72) Inventor: Jessica Walter, Albany, CA (US)

(73) Assignee: Amyris, Inc., Emeryville, CA (US)

( * ) Notice: Subject to any disclaimer, the term of this patent is extended or adjusted under 35 U.S.C. 154(b) by 300 days.

(21) Appl. No.: 16/646,028

(22) PCT Filed: Sep. 12, 2018

(86) PCT No.: PCT/US2018/050732
§ 371 (c)(1),
(2) Date: Mar. 10, 2020

(87) PCT Pub. No.: WO2019/190590
PCT Pub. Date: Oct. 3, 2019

(65) Prior Publication Data

US 2020/0263205 A1 Aug. 20, 2020

Related U.S. Application Data

(60) Provisional application No. 62/560,029, filed on Sep. 18, 2017, provisional application No. 62/667,000, filed on May 4, 2018.

(51) Int. Cl.
*C12N 15/90* (2006.01)
*C12N 9/22* (2006.01)
*C12N 15/11* (2006.01)
*C12N 15/81* (2006.01)

(52) U.S. Cl.
CPC ............. *C12N 15/905* (2013.01); *C12N 9/22* (2013.01); *C12N 15/11* (2013.01); *C12N 15/815* (2013.01); *C12N 2310/20* (2017.05); *C12N 2800/80* (2013.01)

(58) Field of Classification Search
CPC ............ C12N 2800/80; C12N 2310/20; C12N 15/905; C12N 15/11; C12N 15/815; C12N 9/22; C12N 15/102
See application file for complete search history.

(56) References Cited

U.S. PATENT DOCUMENTS

| | | | | |
|---|---|---|---|---|
| 8,685,737 | B2 | 4/2014 | Serber et al. | |
| 9,476,065 | B2 | 10/2016 | Horwitz et al. | |
| 11,390,874 | B2 | 7/2022 | Jiang | |
| 2020/0263188 | A1 * | 8/2020 | Tsegaye ............ | C07K 16/2893 |

FOREIGN PATENT DOCUMENTS

| | | | |
|---|---|---|---|
| WO | 2012/149470 | A1 | 11/2012 |
| WO | 2012/176981 | A1 | 12/2012 |
| WO | 2015/095804 | A1 | 6/2015 |
| WO | 2015/138855 | A1 | 9/2015 |

OTHER PUBLICATIONS

Heus et al., Chromatin structures of Kluyveromyces lactis centromeres in K. lactis and *Saccharomyces cerevisiae*. Chromosoma, 1993, vol. 102: 660-667. (Year: 1993).*
Hoshida et al., Non-homologous end joining-mediated functional marker selection for DNA cloning in the yeast *Kluyveromyces marxianus*. Yeast, 2014, vol. 31: 29-46. (Year: 2014).*
Iborra et al., Kluyveromyces marxianus Small DNA Fragments Contain Both Autonomous Replicative and Centromeric Elements that also Function in Kluyveromyces lactis. Yeast, 1994, vol. 10: 1621-1629. (Year: 1994).*
Liachko et al., An autonomously replicating sequence for use in a wide range of budding yeasts. FEMS Yeast Res., 2014, vol. 14: 364-37. (Year: 2014).*
International Search Report and Written Opinion in PCT Application PCT/US2018/050732 dated Nov. 8, 2019; 14 pages.
Chen, X.J. et al.; "A gene-cloning system for Kluyveromyces lactis and isolation of a chromosomal gene required for killer toxin production"; *Journal of Basic Microbiology*; vol. 28, No. 4; Jan. 1, 1988; pp. 211-220.
Dicarlo, J.E. et al.; "Genome engineering in *Saccharomyces cerevisiae* using CRISPR-Cas systems"; *Nucleic Acid Research*; vol. 41, No. 7; Mar. 4, 2013; pp. 4336-4343.
Horwitz, A.A. et al.; "Efficient Multiplexed Integration of Synergistic Alleles and Metabolic Pathways in Yeasts via CRISPR-Cas"; *Cell Systems*: vol. 1, No. 1; Jul. 1, 2015; pp. 88-96.
Lobs, A-K. et al.; "CRISPR-Cas9-0enabled genetic disruptions for understanding ethanol and ethyl acetate biosynthesis in Kluyveromyces marxianus"; *Biotechnology for Biofuels*; vol. 10, No. 1; Jun. 24, 2017; 14 pages.
Walter, J.M. et al.; "CRISPR-Cas-Assisted Multiplexing (CAM): Simple Same-Day Multi-Locus Engineering in Yeast"; *Journal of Cellular Physiology*: vol. 231, No. 12; Dec. 1, 2016; pp. 2563-2569.
Divisional U.S. Appl. No. 17/841,429, filed Jun. 15, 2022, for "Methods for Genomic Integration in Pichia and Other Host Cells".
Abdel-Banat, B. M.A. et al.; "Random and targeted gene integrations through the control of non-homologous end joining in the yeast Kluyveromyces marxianus" *Yeast*; vol. 27; 2010; pp. 29-39.

* cited by examiner

*Primary Examiner* — Ganapathirama Raghu
(74) *Attorney, Agent, or Firm* — Kilpatrick Townsend and Stockton LLP

(57) ABSTRACT

The present invention provides high efficiency targeted and marker-less single or simultaneous multiple integrations using nucleases and a stable plasmid in *Kluyveromyces* host cells.

7 Claims, 8 Drawing Sheets

Figure 1:
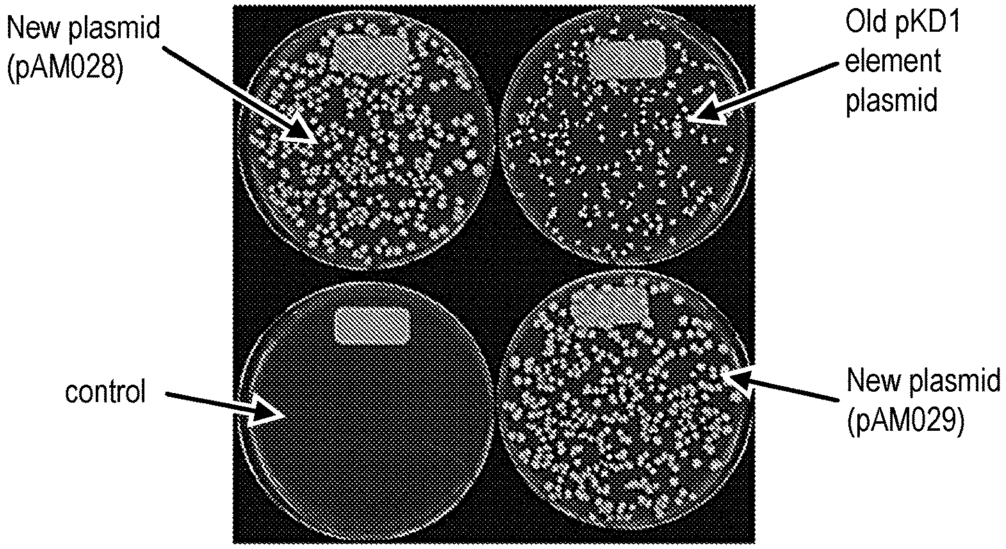

Specification includes a Sequence Listing.

CRISPR multiplexing efficiency using CEN/ARS_1 in KM Strain 1

CRISPR multiplexing efficiency using CEN/ARS_2 in KM Strain 1

CRISPR multiplexing efficiency using CEN/ARS_3 in KM Strain 1

CRISPR multiplexing efficiency using CEN/ARS_4 in KM Strain 1

CRISPR multiplexing efficiency using CEN/ARS_5 in KM Strain 1

METHODS FOR GENOMIC INTEGRATION FOR *KLUYVEROMYCES* HOST CELLS

2. CROSS-REFERENCES TO RELATED APPLICATIONS

The present application is a U.S. National Phase Application Under 371 of PCT/US2018/050732 filed Sep. 12, 2018, which claims priority to U.S. Provisional Application Nos. 62/560,029, filed Sep. 18, 2017, and 62/667,000, filed May 4, 2018, the disclosures of which are incorporated herein in their entireties.

1. STATEMENT AS TO RIGHTS TO INVENTIONS MADE UNDER FEDERALLY SPONSORED RESEARCH AND DEVELOPMENT

This invention was made with Government support under Agreement HR0011-15-3-0001, awarded by DARPA. The Government has certain rights in the invention.

REFERENCE TO SUBMISSION OF A SEQUENCE LISTING AS A TEXT FILE

The Sequence Listing written in file 101928-1100593_SL.txt created on Mar. 5, 2020, 48,386 bytes, machine format IBM-PC, MS-Windows operating system, is hereby incorporated by reference in its entirety for all purposes.

3. FIELD OF THE INVENTION

The methods and compositions provided herein generally relate to the fields of molecular biology and genetic engineering.

4. BACKGROUND

Genetic engineering techniques to introduce targeted modification into a host cell genome find use in a variety of fields. Fundamentally, the determination of how genotype influences phenotype relies on the ability to introduce targeted insertions or deletions to impair or abolish native gene function. In the field of synthetic biology, the fabrication of genetically modified microbes capable of producing compounds or proteins or interest requires the insertion of customized DNA sequences into a chromosome of the host cell; industrial scale production generally requires the introduction of multiple genes in a host cell genome.

For certain host cells, particularly for conventional yeast cells (e.g., *Saccharomyces cerevisiae*), genetic tools are well developed to perform targeted genomic gene deletions and integrations. A variety of non-conventional yeast cells are attractive hosts for industrial applications (e.g., small molecule and protein production). However, the tools for engineering these species are generally poor. For example, the genus *Kluyveromyces*, in particular *K. marxianus*, is an attractive yeast host for the production of industrial products and antibodies due to its fast growth, high acid tolerance and high temperature tolerance. However, making targeted genomic changes to *K. marxianus* has been historically time-consuming due to a high basal rate of non-homologous end joining (NHEJ) and difficulty of maintaining a stable plasmid. CRISPR-based disruption of genes in *K. marxianus* was recently reported for the first time, but no genes were integrated and disruption relied upon NHEJ. Currently, neither meganuclease-mediated, targeted, single genomic integrations nor multiplexed integrations have been reported in *K. marxianus*. Such integrations would dramatically reduce the genetic engineering cycle time by at least 50%.

Therefore, currently known methods for genomic modification for various *Kluyveromyces* host cells are in need for improvement. The present invention addresses these and other needs.

5. SUMMARY

The present invention provides methods of modifying a target site in a *Kluyveromyces* host cell genome. The methods comprise contacting the host cell, which has reduced non-homologous end joining (NHEJ) activity, with: a first linear nucleic acid capable of homologous recombination with itself or with one or more additional linear nucleic acids contacted with the host cell, whereby homologous recombination in the host cell results in formation of a circular extrachromosomal nucleic acid comprising a coding sequence for a selectable marker and a stability element from *K. marxianus*. In some embodiments, the stability element comprises a CEN sequence at least 95% identical to SEQ ID NO: 2 and an ARS consensus sequence at least 90% identical to SEQ ID NO: 3; a nuclease capable of cleaving the target site; and a donor DNA molecule capable of homologous recombination at the cleaved target site, whereby homologous recombination in the host cell results in integration of the donor linear nucleic acid at the target site. Transformed host cells expressing the selectable marker are then selected. In some embodiments, the methods further comprise recovering a host cell wherein the donor DNA molecule has homologously recombined at the target site.

In some embodiments the stability element is at least 90% identical to a sequence less than 750 bp in length and comprising residues 202 to 876 or residues 537 to 1252 of SEQ ID NO: 1 In other embodiments, the stability element is at least 95% identical to SEQ ID NO: 1. The host cell can be *K. marxianus.*

In some embodiments, the step of contacting includes contacting the host cell with two or more donor DNA molecules capable of homologous recombination with different target sites in the host cell genome, whereby homologous recombination in the host cell results integration of the donor DNA molecules at the different target sites.

In some embodiments, the circular extrachromosomal nucleic acid further comprises a coding sequence for the nuclease. The nuclease in some cases may be an RNA-guided DNA endonuclease, as a Cas9 endonuclease.

In some embodiments, the circular extrachromosomal nucleic acid further comprises a sequence that encodes a crRNA activity and a tracrRNA activity that enables site-specific recognition and cleavage of the target site by the RNA-guided DNA endonuclease. The crRNA activity and the tracrRNA activity may be expressed as a single contiguous RNA molecule.

In some embodiments, the nucleic acid encoding the RNA-guided DNA endonuclease is pre-integrated into the host cell genome prior to contacting the host cell with sequences that encode a crRNA activity and a tracrRNA activity. The NHEJ may be reduced by integrating the nucleic acid encoding the RNA-guided endonuclease at YKU70 or YKU80 loci. The invention also provides method for modifying a target site in a *Kluyveromyces* host cell genome, these methods comprise: contacting the host cell, which has reduced non-homologous end joining (NHEJ) activity, with a nucleic acid molecule comprising a stability element comprising a CEN sequence at least 95% identical to SEQ ID NO: 2 and an ARS consensus sequence at least 90% identical to SEQ ID NO: 3 and nucleic acid sequence encoding a nuclease capable of cleaving the target site; and a donor DNA molecule capable of homologous recombination at the cleaved target site. A transformed host cell is then selected in which the donor DNA molecule integrated into the target site. The host cell may be *K. marxianus*. The nuclease may be a meganuclease, as F-CphI. In some emdodiments, the stability element is at least 90% identical to a sequence less than 750 bp in length and comprising residues 202 to 876 of SEQ ID NO: 1. In other embodiments, the stability element is at least 95% identical to SEQ ID NO: 1.

The invention also provides host cells made by the methods of invention.

The invention further provides recombinant nucleic acid molecules comprising (1) a nucleic acid sequence encoding a nuclease, or a nucleic acid sequence encoding a crRNA activity and a tracrRNA activity that enables site-specific recognition and cleavage of a target site by an RNA-guided DNA endonuclease and (2) a stability element comprising a CEN sequence at least 95% identical to SEQ ID NO: 2 and an ARS consensus sequence at least 90% identical to SEQ ID NO: 3. In some emdodiments, the stability element is at least 90% identical to a sequence less than 750 bp in length and comprising residues 202 to 876 of SEQ ID NO: 1. In other embodiments, the stability element is at least 95% identical to SEQ ID NO: 1. The nuclease may be an RNA-guided DNA endonuclease, such as a Cas9 endonuclease. The nuclease may be meganuclease, such as F-CphI.

The invention further provides recombinant nucleic acid molecules and host cells comprising a stability element comprising a CEN sequence and/or ARS consensus sequence shown in SEQ ID NOS: 4, 7, or 10. The invention further provides recombinant nucleic acid molecules and host cells comprising a stability element comprising a sequence that is at least 90% or 95% identical to the CEN sequence and/or ARS consensus sequence shown in SEQ ID NOS: 4, 7, or 10. The invention further provides methods described herein using these recombinant nucleic acid molecules and host cells.

Definitions

As used in this specification and the appended claims, the singular forms "a," "an," and "the" include plural reference unless the context clearly dictates otherwise.

As used herein, the term "stability element" refers to a nucleic acid sequence of between about 200 and about 1300 bp, usually between about 400 and about 900 bp, and often between about 600 and about 750 bp comprising an autonomously replicating sequence (ARS) consensus sequence and, optionally, a centromere sequence (CEN). A stability element allows an extrachromosomal DNA molecule (either linear or circular) comprising the stability element to remain stable in a host cell for extended periods of culturing in non-selective media. The stability elements of the invention typically provide for stability of an extrachromosomal DNA molecule for at least about 10 generations, usually about 20, and often about 30 or more generations in non-selective media.

ARS and CEN sequences have been well studied in yeast. ARSs are origins of DNA replication in yeast chromosomes and are typically short modular DNA sequences comprising an 11-17 bp core sequence element called the ARS Consensus Sequence (ACS), as well as flanking sequences. CEN sequences are part of the complex structures on chromosomes to which spindle fibers attach during meiosis and mitosis. Such sequences are typically between about 100 and about 200 bp long and can be subdivided into three conserved DNA elements CDEI, CDEII and CDEIII. Exemplary CEN sequences of the invention include SEQ ID NOs: 2, 5, 8, and 11. Exemplary ARS consensus sequences of the invention include SEQ ID NOs: 3, 6, 9, and 12).

Exemplary stability elements of the invention are derived from *K. marxianus* and include SEQ ID NOs: 1, 4, 7, 10, 13, and 14). Also included are subsequences of these sequence which comprise the ARS consensus sequence, optionally a CEN sequence, and any intervening sequences. Exemplary stability elements of this type include residues 202-876 or residues 537-1252 of SEQ ID NO: 1 and residues 1 to 566 or residues 348-1043 of SEQ ID NO: 4.

One of skill will recognize that the exemplified sequences noted above can be modified and still provide stability for extrachromosomal DNA molecules. For example, CEN sequences, ARS consensus sequences, or stability elements having at least about 90%, 91%, 92% 93%, 94%, 95%, 96%, 97%, 98%, or 99% sequence identity to the exemplified sequences are contemplated by the invention. Those of skill in the art readily understand how to determine the identity of two nucleic acids. For example, the identity can be calculated after aligning the two sequences so that the identity is at its highest level. Another way of calculating identity can be performed by published algorithms. For example, optimal alignment of sequences for comparison can be conducted using the algorithm of Needleman and Wunsch, J. Mol. Biol. 48: 443 (1970).

The term "nucleic acid" or "nucleotide" refers to deoxyribonucleic acids (DNA) or ribonucleic acids (RNA) and polymers thereof in either single- or double-stranded form. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260: 2605-2608 (1985); and Rossolini et al., Mol. Cell. Probes 8:91-98 (1994)).

The term "gene" can refer to the segment of DNA involved in producing or encoding a polypeptide chain. It may include regions preceding and following the coding region (leader and trailer) as well as intervening sequences (introns) between individual coding segments (exons). Alternatively, the term "gene" can refer to the segment of DNA involved in producing or encoding a non-translated RNA, such as an rRNA, tRNA, gRNA, or micro RNA A "promoter" is defined as one or more a nucleic acid control sequences that direct transcription of a nucleic acid. As used herein, a promoter includes necessary nucleic acid sequences near the start site of transcription. A promoter also optionally includes distal enhancer or repressor elements, which can be located as much as several thousand base pairs from the start site of transcription.

As used herein, the term "marker-less" refers to integration of a donor DNA into a target site within a host cell genome without accompanying integration of a selectable marker. In some embodiments, the term also refers to the recovery of such a host cell without utilizing a selection scheme that relies on integration of selectable marker into the host cell genome. For example, in certain embodiments, a selection marker that is episomal or extrachromasomal may be used to select for cells comprising a plasmid comprising a gRNA. Such use is considered marker-less, as long as the selectable marker is not integrated into the host cell genome.

As used herein, the term "operably linked" refers to a functional linkage between nucleic acid sequences such that the sequences encode a desired function. For example, a coding sequence for a gene of interest, e.g., a selectable marker, is in operable linkage with its promoter and/or regulatory sequences when the linked promoter and/or regulatory region functionally controls expression of the coding sequence. It also refers to the linkage between coding sequences such that they may be controlled by the same linked promoter and/or regulatory region; such linkage between coding sequences may also be referred to as being linked in frame or in the same coding frame. "Operably linked" also refers to a linkage of functional but non-coding sequences, such as an autonomous propagation sequence or origin of replication. Such sequences are in operable linkage when they are able to perform their normal function, e.g., enabling the replication, propagation, and/or segregation of a vector bearing the sequence in a host cell.

As used herein, the term "transformation" refers to a genetic alteration of a host cell resulting from the introduction of exogenous genetic material into the host cell.

As used herein, the term "selecting a host cell expressing a selectable marker" also encompasses enriching for host cells expressing a selectable marker from a population of transformed cells.

As used herein, the term "selectable marker" refers to a gene which functions as guidance for selecting a host cell comprising a marker, for example, a marker expressed by a circular, extrachromosomal nucleic acid in the host cell, as described herein. The selectable markers may include, but are not limited to: fluorescent markers, luminescent markers and drug selectable markers, and the like. The fluorescent markers may include, but are not limited to, genes encoding fluorescence proteins such as green fluorescent protein (GFP), cyan fluorescent protein (CFP), yellow fluorescent protein (YFP), red fluorescent protein (dsRFP) and the like. The luminescent markers may include, but are not limited to, genes encoding luminescent proteins such as luciferases. Drug selectable markers suitable for use with the methods and compositions provided herein include, but are not limited to, resistance genes to antibiotics, such as ampicillin, streptomycin, gentamicin, kanamycin, hygromycin, tetracycline, chloramphenicol, and neomycin. In some embodiments, the selection may be positive selection; that is, the cells expressing the marker are isolated from a population, e.g. to create an enriched population of cells comprising the selectable marker. In other instances, the selection may be negative selection; that is, the population is isolated away from the cells, e.g. to create an enriched population of cells that do not comprise the selectable marker. Separation can be by any convenient separation technique appropriate for the selectable marker used. For example, if a fluorescent marker is used, cells can be separated by fluorescence activated cell sorting, whereas if a cell surface marker has been inserted, cells can be separated from the heterogeneous population by affinity separation techniques, e.g. magnetic separation, affinity chromatography, "panning" with an affinity reagent attached to a solid matrix, or other convenient technique.

"Polypeptide," "peptide," and "protein" are used interchangeably herein to refer to a polymer of amino acid residues. As used herein, the terms encompass amino acid chains of any length, including full-length proteins, wherein the amino acid residues are linked by covalent peptide bonds.

As used herein, the term "complementary" or "complementarity" refers to specific base pairing between nucleotides or nucleic acids. In some embodiments, for example, and not to be limiting, base pairing between a gRNA (gRNA) and a target site or region in the genome of a host cell is described. Complementary nucleotides are, generally, A and T (or A and U), and G and C. The gRNAs described herein can comprise sequences, for example, a DNA targeting sequence that is perfectly complementary or substantially complementary (e.g., having 1-4 mismatches) to a genomic sequence in a host cell.

The "CRISPR/Cas" system refers to a widespread class of bacterial systems for defense against foreign nucleic acid. CRISPR/Cas systems are found in a wide range of eubacterial and archaeal organisms. CRISPR/Cas systems include type I, II, and III sub-types. Wild-type type II CRISPR/Cas systems utilize an RNA-guided DNA endonuclease, Cas9, in complex with a gRNA to recognize and cleave foreign nucleic acid.

As used herein, the terms "cleave," "cleavage" and/or "cleaving" with respect to homing endonuclease, zinc-finger nuclease, TAL-effector nuclease, or an RNA-guided endonuclease, for example, Cas9, refers to the act of creating a break in a particular nucleic acid. The break can leave a blunt end or sticky end (i.e., 5' or 3' overhang), as understood by those of skill in the art. The terms also encompass single strand DNA breaks ("nicks") and double strand DNA breaks.

As used herein, the term "Cas9" refers to an RNA-guided nuclease (e.g., of bacterial or archeal orgin, or derived therefrom). RNA-guided nucleases include the foregoing Cas9 proteins and homologs thereof, and include but are not limited to, Cpfl (See, e.g., Zetsche et al., Cell, Volume 163, Issue 3, p759-771, 22 Oct. 2015).

Cas9 homologs are found in a wide variety of eubacteria, including, but not limited to bacteria of the following taxonomic groups: Actinobacteria, Aquificae, Bacteroidetes-Chlorobi, Chlamydiae-Verrucomicrobia, Chlroflexi, Cyanobacteria, Firmicutes, Proteobacteria, Spirochaetes, and Thermotogae. An exemplary Cas9 protein is the *Streptococcus pyogenes* Cas9 protein. Additional Cas9 proteins and homologs thereof are described in, e.g., Chylinksi, et al., RNA Biol. 2013 May 1; 10(5): 726-737 ; Nat. Rev. Microbiol. 2011 June; 9(6): 467-477; Hou, et al., Proc Natl Acad Sci USA. 2013 Sep. 24; 110(39):15644-9; Sampson et al., Nature. 2013 May 9; 497(7448):254-7; and Jinek, et al., Science. 2012 Aug. 17; 337(6096):816-21. Variants of any of the Cas9 nucleases provided herein can be optimized for efficient activity or enhanced stability in the host cell. Thus, engineered Cas9 nucleases, for example, codon optimized Cas9 nucleases for expression in *Kluyveromyces* are also contemplated.

As used herein, the terms "modifying," or "modification," in the context of modifying a target site in a host cell genome refers to inducing a nucleic acid break in the target site. A modification can be used to edit the genome. As used herein the term "editing" refers to a structural change in the sequence of the genome at a target site. For example, the host cell genome may be edited by deleting or inserting a nucleotide sequence into the genome of the cell. The nucleotide sequence can encode a polypeptide or a fragment thereof. Such editing can be performed, for example, by inducing a double stranded break within a target site in the genome of a host cell, or a pair of single stranded nicks on opposite strands and flanking the target site in the genome of a host cell. Methods for inducing single or double stranded breaks at or within a target site include the use of nucleases, such as a meganuclease, an RNA-guided DNA endonuclease, or a derivatives thereof.

As used herein, the phrases "introducing" or "contacting" in the context of introducing a nucleic acid or protein into a host cell refers to any process that results in the presence of a heterologous nucleic acid or polypeptide inside the host cell. For example, the terms encompass introducing a nucleic acid molecule (e.g., a plasmid or a linear nucleic acid) that encodes the nucleic acid of interest (e.g., an RNA molecule) or polypeptide of interest and results in the transcription of the RNA molecules and translation of the polypeptides. The terms also encompass integrating the nucleic acid encoding the RNA molecules or polypeptides into the genome of a progenitor cell. The nucleic acid is then passed through subsequent generations to the host cell, so that, for example, a nucleic acid encoding an RNA-guided endonuclease is "pre-integrated" into the host cell genome. In some cases, introducing refers to translocation of a nucleic acid or polypeptide from outside the host cell to inside the host cell. Various methods of introducing nucleic acids, polypeptides and other biomolecules into host cells are contemplated, including but not limited to, electroporation, contact with nanowires or nanotubes, spheroplasting, PEG 1000-mediated transformation, biolistics, lithium acetate transformation, lithium chloride transformation, and the like.

As used herein the phrase "heterologous" refers to what is not normally found in nature. The term "heterologous nucleotide sequence" refers to a nucleotide sequence not normally found in a given cell in nature. As such, a heterologous nucleotide sequence may be: (a) foreign to its host cell (i.e., is exogenous to the cell); (b) naturally found in the host cell (i.e., endogenous) but present at an unnatural quantity in the cell (i.e., greater or lesser quantity than naturally found in the host cell); or (c) be naturally found in the host cell but positioned outside of its natural locus.

As used herein the term "homologous recombination" refers to a cellular process in which nucleotide sequences are exchanged between two sufficiently identical molecules of DNA. Two DNA molecules have "sufficient" sequence identity if the two sequences have at least 70%, at least 75%>, at least 80%>, at least 85%>, at least 90%>, at least 95%>, at least 99%>, or 100%, identity between recombination regions, over a length of, for example, at least 15 base pairs, at least 20 base pairs, at least 50 base pairs, at least 100 base pairs, at least 250 base pairs, at least 500 base pairs, or more than 500 base pairs. Those of skill in the art readily understand how to determine the identity of two nucleic acids. For example, the identity can be calculated after aligning the two sequences so that the identity is at its highest level. Another way of calculating identity can be performed by published algorithms. For example, optimal alignment of sequences for comparison can be conducted using the algorithm of Needleman and Wunsch, J. Mol. Biol. 48: 443 (1970). For a discussion of effective lengths of homology between recombination regions, see Hasty et al. (Mol Cell Biol 11:5586-91 (1991)).

As used herein, the term "non-homologous end joining" or NHEJ refers to a cellular process in which cut or nicked ends of a DNA strand are directly ligated without the need for a homologous template nucleic acid. NHEJ can lead to the addition, the deletion, substitution, or a combination thereof, of one or more nucleotides at the repair site.

As used herein, the term homology directed repair (HDR) refers to a cellular process in which cut or nicked ends of a DNA strand are repaired by polymerization from a homologous template nucleic acid, for example a donor DNA molecule. Thus, the original sequence is replaced with the sequence of the template. The homologous template nucleic acid can be provided by homologous sequences elsewhere in the genome (sister chromatids, homologous chromosomes, or repeated regions on the same or different chromosomes). Alternatively, an exogenous template nucleic acid, for example, a donor DNA molecule can be introduced to obtain a specific HDR-induced change of the sequence at the target site. In this way, specific sequences can be introduced at the cut site.

As used herein, the term "KU70" is used interchangeably with "YKu70", and the term "KU80" is used interchangeably with "YKu80". The proteins encoded from YKu70 (or KU70) and YKu80 (or KU80) loci are involved in non-homologous end joining. KU exists as a heterodimer of two polypeptides of approximately 70 kDa (generally referred to as YKu70 or KU70 depending organisms), and 80 kDa (generally referred to as YKu80 or KU80 depending on organisms).

6. BRIEF DESCRIPTION OF THE FIGURES

FIG. 1 illustrates a schematic diagram of petri dishes showing growth of colonies. FIG. 1 illustrates that the new *K. marxianus* CEN/ARS plasmid generated is more stable than the same plasmid with a pKD1 element instead of *K. marxianus*-specific CEN/ARS sequences. Colonies transformed with the *K. marxianus* CEN/ARS plasmid are larger and rounder than the old colonies, which were rough due to colony sectoring and loss of the plasmid. In addition, colonies containing the new plasmid grew overnight in liquid culture under Nat selection (unlike colonies containing the pKD1 element plasmid), and transformable plasmid was recovered from yeast minipreps.

Figure 2:
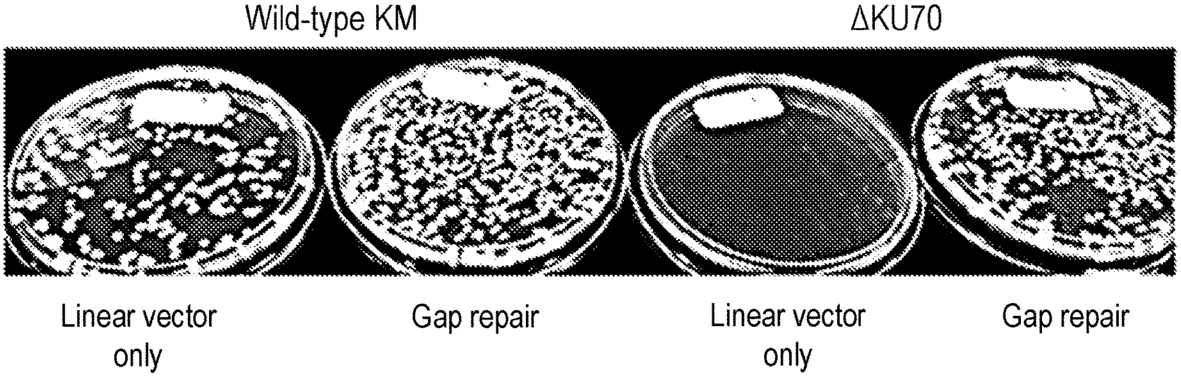

FIG. 2 illustrates a schematic diagram of petri dishes showing growth of colonies. FIG. 2 illustrates that deletion of YKU70 eliminates NHEJ-mediated circularization of linear plasmids, and homologous recombination is demonstrated by plasmid gap repair in the same background. Wild-type *K. marxianus* (left) circularizes a linear vector fragment with or without an overlapping gap repair fragment. A YKU70 deleted strain (right) only circularizes the plasmid when the gap repair fragment is supplied.

Figure 3A:
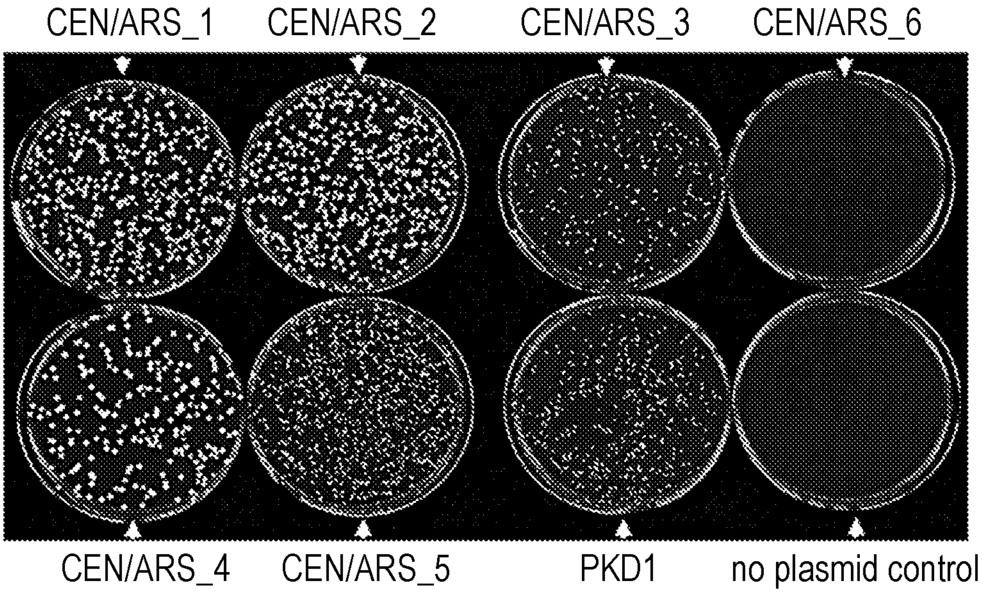
Figure 3B:
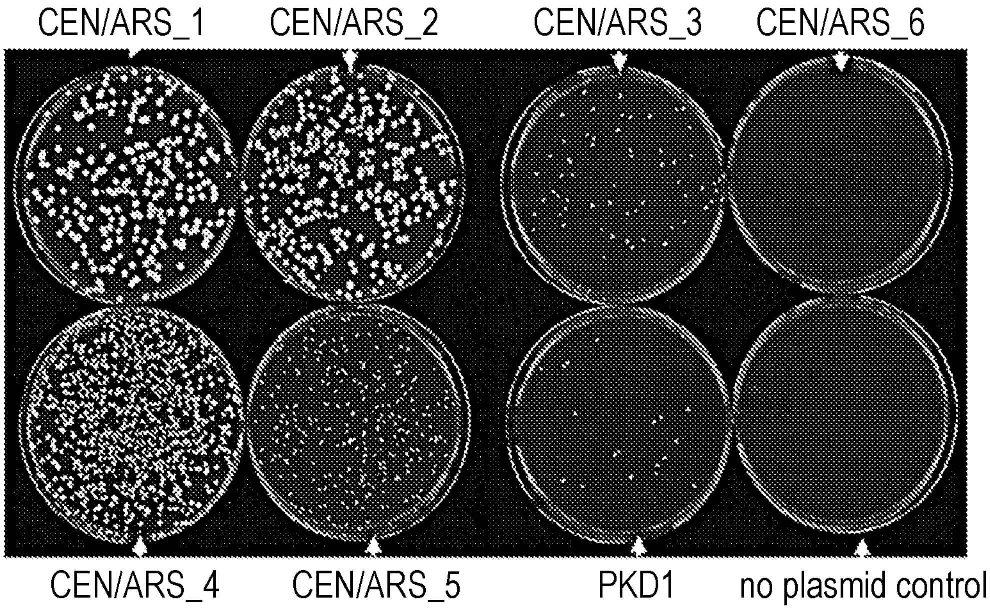

FIG. 3 shows transformation of *K. marxianus* wild-type strains with plasmids containing different *K. marxianus* CEN/ARS elements. 100 ng of miniprepped plasmid was used in each transformation. A. Transformation of Strain 1; B. Transformation of Strain 2.

Figure 4:
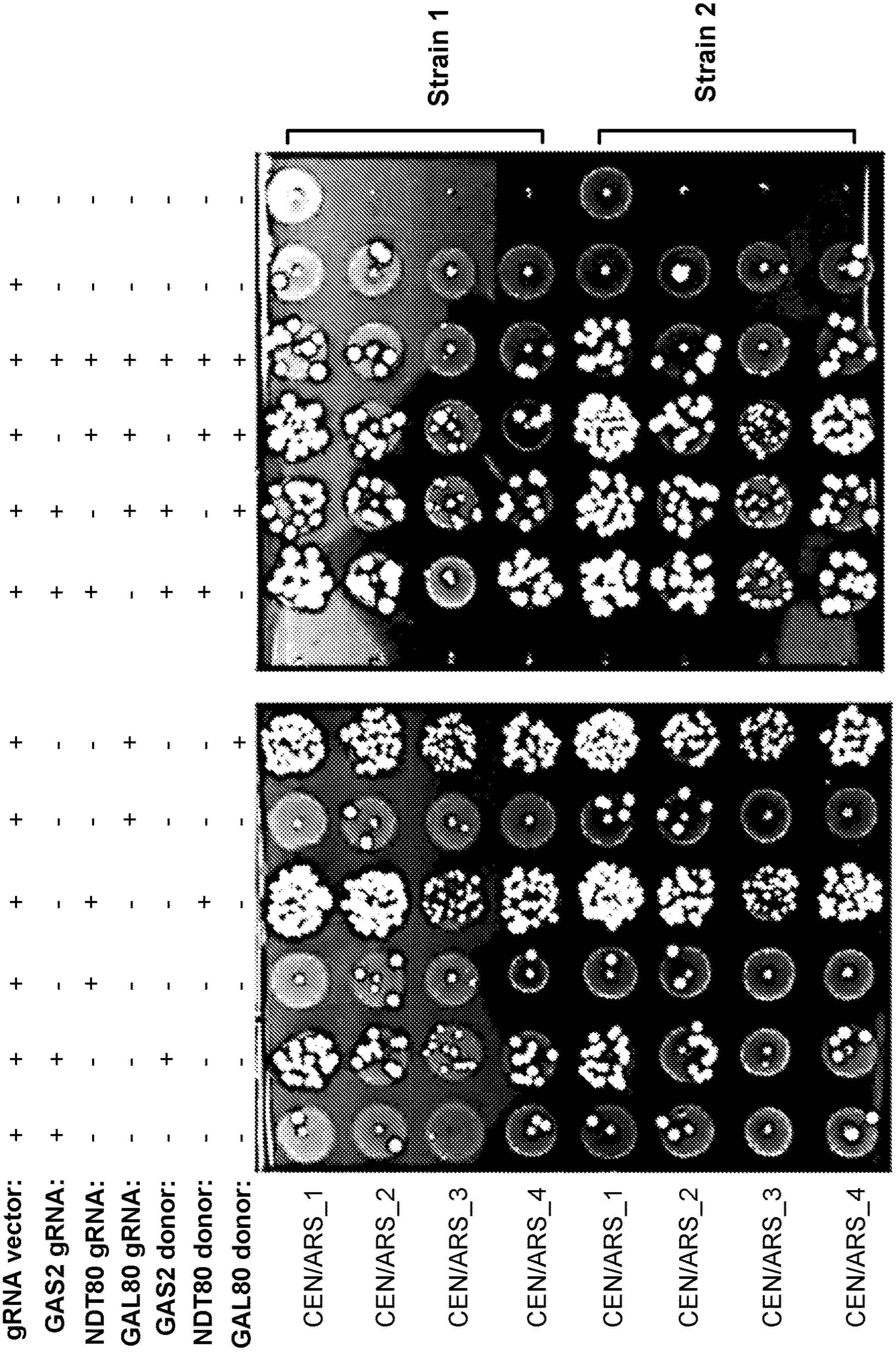

FIG. 4 shows the experiment lay-out for *K. marxianus* transformation using gRNA vector containing different CEN/ARS elements. Both strains served as host for transformation. Each transformation contained 50 ng of linear gRNA vector with CEN/ARS_1 to CEN/ARS_4; 200 ng of gRNA and 500 ng of donor DNA was added to the transformation according to the plate lay-out.

Figure 5:
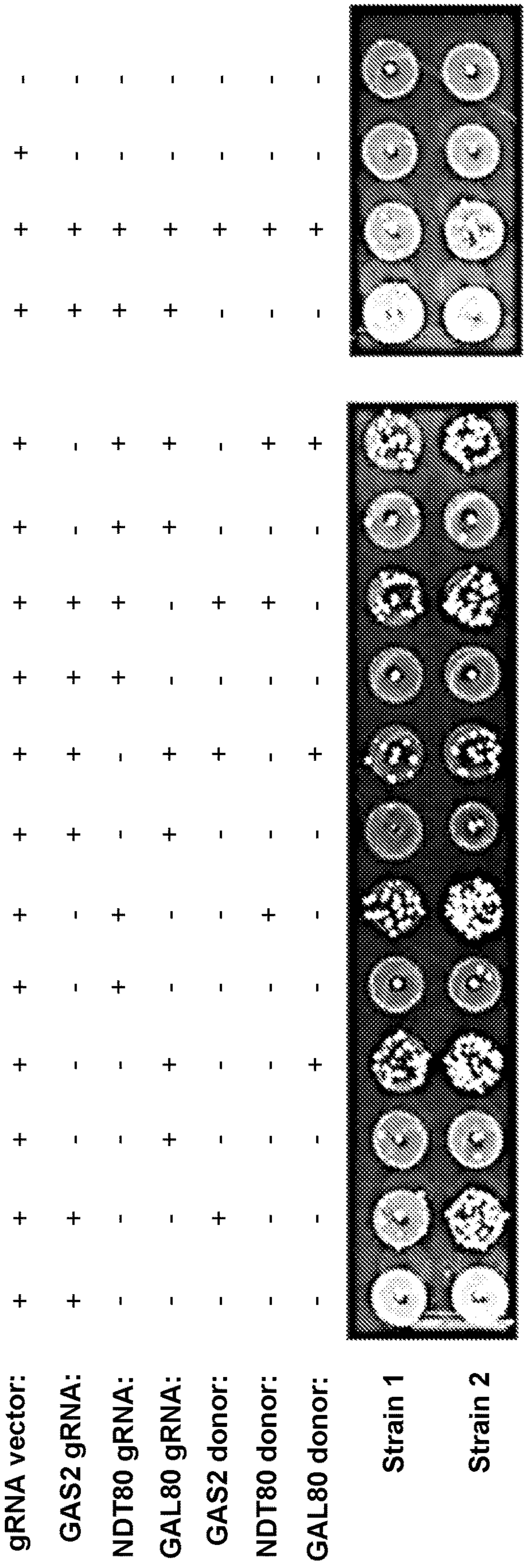
Figure 6A:
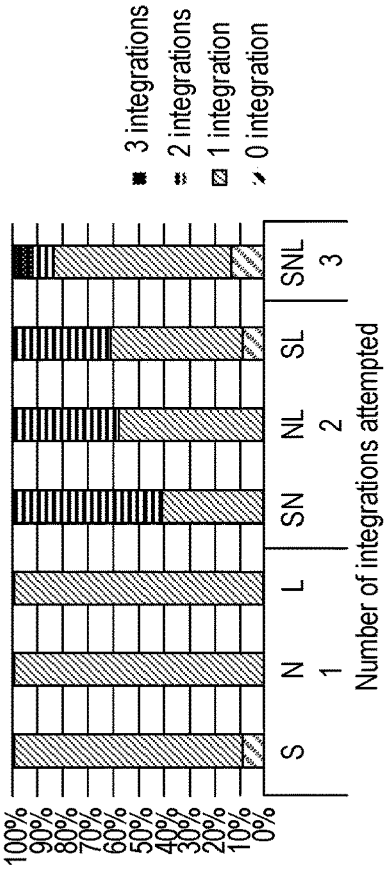
Figure 6B:
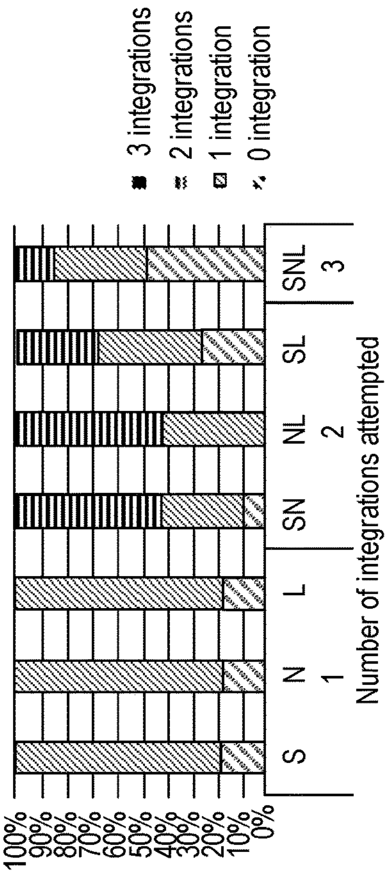
Figure 6C:
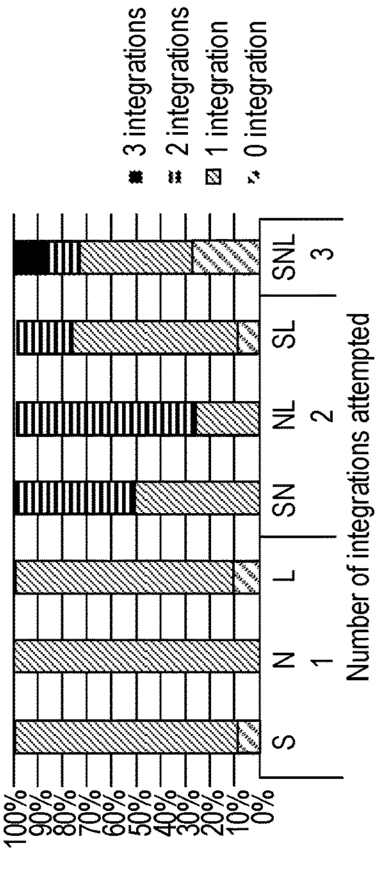
Figure 6D:
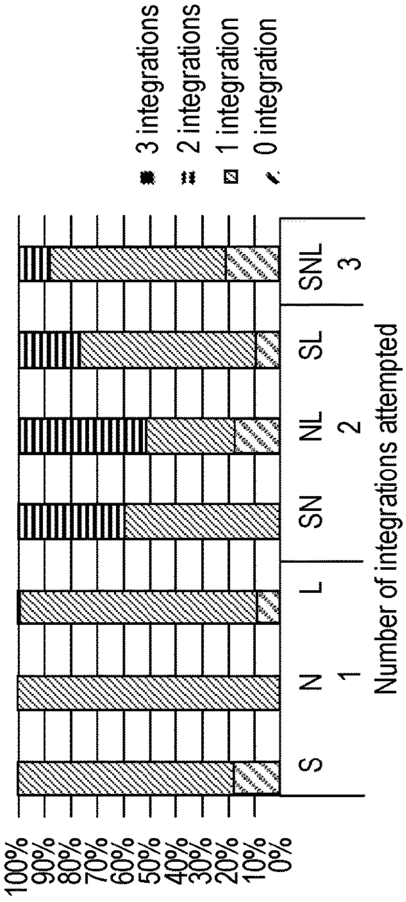
Figure 6E:
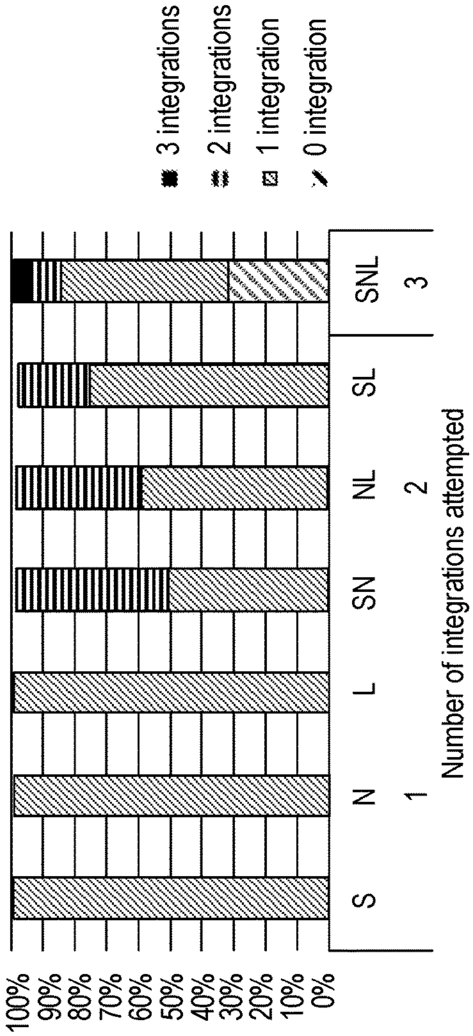
Figure 7A:
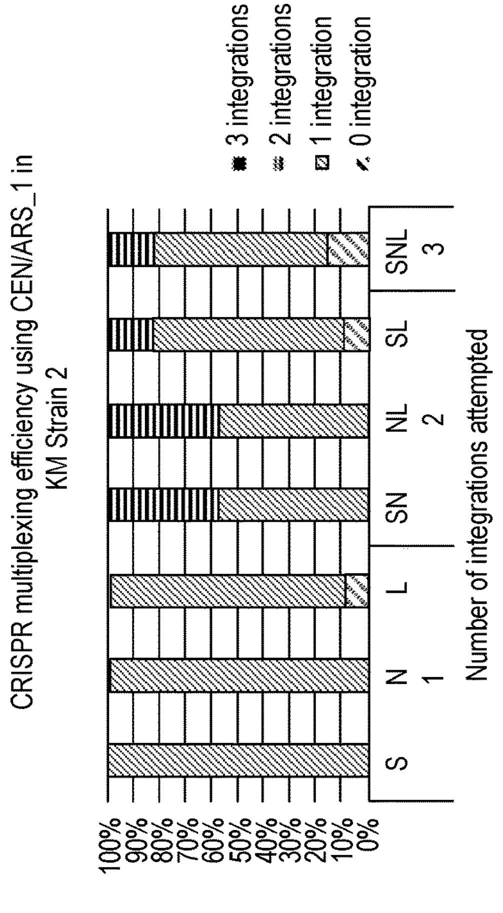
Figure 7B:
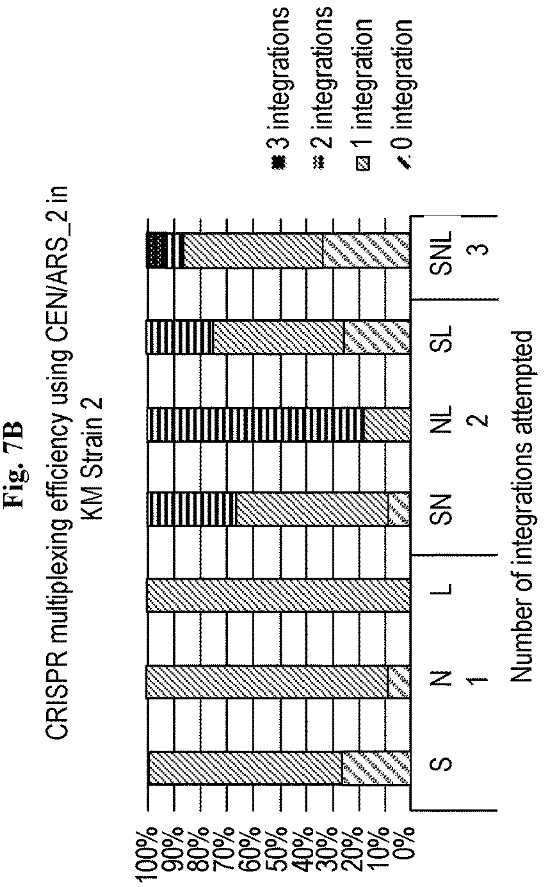
Figure 7C:
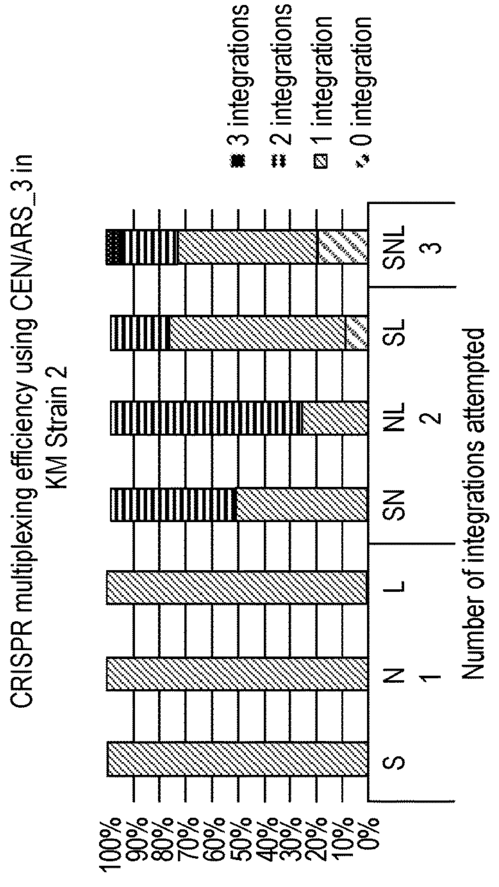
Figure 7D:
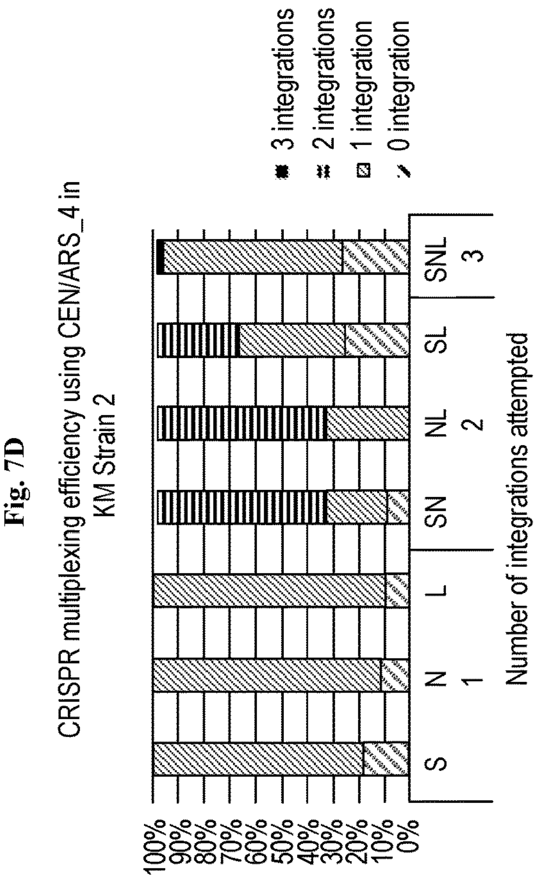
Figure 7E:
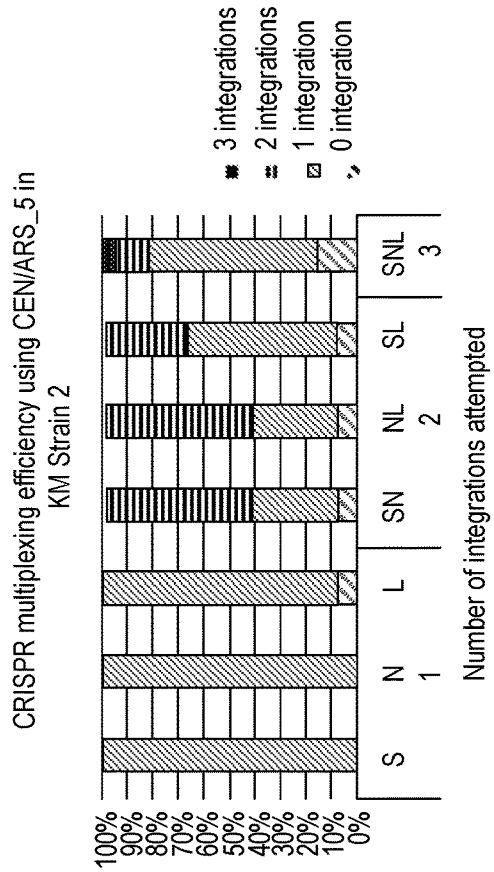

FIG. 5 shows *K. marxianus* transformation using gRNA vector containing CEN/ARS_5. Both strains served as host for transformation. Each transformation contained 50 ng of linear gRNA vector with CEN/ARS_5; 200 ng of gRNA and 500 ng of donor DNA was added to the transformation according to the plate lay-out.

FIG. 6 is a summary of integration at three loci GAS2, NDT80 and GAL80 from transformation of *K. marxianus*

Strain 1. Each locus was screened by colony PCR using sequence-specific primers. 12 colonies were tested for single and double integrations; 30 colonies were tested for triple integrations. GAS2: S; NDT80: N; GAL80: L. A to E: summary of efficiency of CEN/ARS_1 to CEN/ARS_5.

FIG. 7 is a summary of integration at three loci GAS2, NDT80 and GAL80 from transformation of *K. marxianus* Strain 2. Each locus was screened by colony PCR using sequence-specific primers. 12 colonies were tested for single and double integrations; 30 colonies were tested for triple integrations. GAS2: S; NDT80: N; GAL80: L. A to E: summary of efficiency of CEN/ARS_1 to CEN/ARS_5.

7. DETAILED DESCRIPTION OF THE EMBODIMENTS

The present invention provides methods of modifying one or more target sites in a *Kluyveromyces* host cell genome. The methods of the invention use DNA molecules comprising a stability element of the invention that allows the DNA molecules to remain stable in the host cell for multiple generations.

7.1 Gap Repair

In some embodiments, modification of the target sites comprises methods which use CRISPR/Cas systems and in vivo assembly of marker and/or gRNA vectors via gap repair, as described in WO2015/095804, which is incorporated herein by reference.

In these methods, the *Kluyveromyces* host cell, which has reduced non-homologous end joining (NHEJ) activity, is contacted with a linear nucleic acid comprising a stability element of the invention. The linear nucleic acid molecule is capable of homologous recombination with itself or with one or more additional linear nucleic acids contacted with the host cell, whereby homologous recombination in the host cell results in formation of a circular extrachromosomal nucleic acid comprising a coding sequence for a selectable marker and the stability element. The cell also comprises a nuclease capable of cleaving the target site and, optionally, a donor DNA molecule capable of homologous recombination at the cleaved target site, whereby homologous recombination in the host cell results in integration of the donor linear nucleic acid at the target site. Transformed cells are identified by the presence of the selectable marker on the circular extrachromosomal nucleic acid.

The donor DNA molecule is typically heterologous to the host cell and is flanked by nucleotide sequences that are homologous to genomic sequences flanking the target site. In some embodiments, the donor DNA molecule comprises a homologous sequence at the 5' terminus that is about 70%, 75%, 80%, 85%, 90%, 95% or 100% homologous to a 5' region of a selected genomic target site In some embodiments, the donor DNA molecule comprises a homologous sequence at the 3' terminus that is about 70%, 75%, 80%, 85%, 90%, 95% or 100% homologous to a 3' region of a selected genomic target site. In some cases, each of the homologous sequences flanking the donor DNA molecule comprises from about 50 to about 1500 nucleotides.

The donor DNA molecule may comprise any nucleic acid of interest. For example, the donor DNA molecule may comprise a gene of interest that can be knocked in to a host genome. In other embodiments, the donor DNA molecule functions as a knockout construct that is capable of specifically disrupting a target gene upon integration of the construct into the target site of the host cell genome, thereby rendering the disrupted gene non-functional. Examples of nucleic acids of interest include, but are not limited to, a protein-coding sequence, a promoter, an enhancer, terminator, transcriptional activator, transcriptional repressor, transcriptional activator binding site, transcriptional repressor binding site, intron, exon, poly-A tail, multiple cloning site, nuclear localization signal, mRNA stabilization signal, integration loci, epitope tag coding sequence, degradation signal, or any other naturally occurring or synthetic DNA molecule. In specific embodiments, the nucleic acid of interest does not comprise a nucleic acid encoding a selectable marker.

NHEJ activity in the host cell may be disrupted in a number of ways. Typically, a gene locus that is involved in NHEJ activity of the cell is disrupted. For example, the YKU70 gene locus may be disrupted, such that NHEJ activity is reduced in the cell. In some cases, the YKU70 gene locus is disrupted by inserting or integrating a nucleic acid encoding an RNA-guided endonuclease in the YKU70 gene locus. The reduction in NHEJ activity can be a reduction of at least 20%, 30%, 40%, 50%, 60%, 70%, 80%, 90%, 100% or any percent reduction in between these percentages, as compared to a *Kluyveromyces* cell that does not have a disruption in a gene controlling NHEJ in the cell.

In some embodiments, the RNA-guided DNA endonuclease is provided by introducing a nucleic acid encoding the endonuclease into the host cell. For example, a plasmid or vector comprising a stability element of the invention and a nucleic acid encoding the RNA-guided DNA endonuclease can be introduced into the cell. In some embodiments, the plasmid can further comprise a nucleic acid sequence encoding a selectable marker for maintenance of the plasmid in the host cell. In some embodiments the nucleic acid encoding the endonuclease further comprises a promoter sequence. In some embodiments, the nucleic acid encoding the RNA-guided DNA endonuclease is integrated into genome of the host cell. In certain embodiments, the RNA-guided DNA endonuclease, for example, Cas9, is integrated into the YKU70 gene of the *Kluyveromyces* host cell, thereby reducing NHEJ activity in the yeast cell. In some embodiments, the nucleic acid encoding the RNA-guided DNA endonuclease is under the control of a constitutive promoter. In some embodiments, the RNA-guided DNA endonuclease can be introduced into the host cell prior to, simultaneously with, or after introduction of the first and second linear nucleic acids. In other embodiments, the RNA-guided DNA endonuclease can be introduced into the host cell prior to, simultaneously with, or after introduction of the first linear nucleic acids, the second linear nucleic acid and the donor DNA molecule.

In some embodiments, the first linear nucleic acid comprises two internal homologous sequences that are capable of homologously recombining with each other, whereby homologous recombination of the internal homologous sequences results in formation of the circular extrachromosomal nucleic acid comprising a stability element of the invention and expressing the selectable marker. Once circularized, the extrachromosomal nucleic acid includes a coding sequence for a selectable marker, and suitable regulatory sequences such as a promoter and/or a terminator that enables expression of the marker in the host cell. Providing the selectable marker on a circular, extrachromosomal nucleic acid, allows markerless integration of one or more donor DNA molecules into a host cell genome, while avoiding the integration of extraneous sequences (i.e., a selectable marker) into the genome and any deleterious effects associated with prolonged marker expression.

In some embodiments, the methods of the invention provide for markerless recovery of a transformed host cell comprising a successfully integrated donor nucleic acid. Such a cell occurs within a frequency of about one every 1000, 900, 800, 700, 600, 500, 400, 300, 200 or 100 contacted host cells, or clonal populations thereof, screened. In particular embodiments, markerless recovery of a transformed host cell comprising a successfully integrated donor nucleic acid occurs within a frequency of about one every 90, 80, 70, 60, 50, 40, 30, 20, or 10 contacted host cells, or clonal populations thereof, screened. In more particular embodiments, markerless recovery of a transformed cell comprising a successfully integrated donor nucleic acid occurs within a frequency of about one every 9, 8, 7, 6, 5, 4, 3, or 2 contacted host cells, or clonal populations thereof, screened.

A variety of methods are available to identify those cells having an altered genome at or near the target site without the use of a selectable marker. In some embodiments, such methods seek to detect any change in the target site, and include but are not limited to PCR methods, sequencing methods, nuclease digestion, e.g., restriction mapping, Southern blots, and any combination thereof. Phenotypic readouts, for example, a predicted gain or loss of function, can also be used as a proxy for effecting the intended genomic modification(s).

In some embodiments, the first linear nucleic acid comprising a selectable marker is capable of recombining with a second linear nucleic acid encoding, for example, one or more gRNAs. After introduction of the first and second linear nucleic acids, the first and second linear nucleic acids undergo homologous recombination to form a circular, episomal or extrachromosomal nucleic acid comprising the coding sequence for the selectable marker and the one or more gRNAs.

Subsequent to formation of the extrachromosomal nucleic acid comprising the coding sequence for the selectable marker and the gRNA, the gRNA is transcribed from the extrachromosomal nucleic acid and guides the RNA-guided DNA endonuclease expressed in the host cell to a target site in the genome of the host cell, where the endonuclease creates a break at the target site.

In typical embodiments, the methods of the invention are used to integrate a plurality (i.e., two or more) donor DNA molecules into a plurality of target sites of the host cell genome. In these embodiments, the *Kluyveromyces* host cell is contacted with a first linear nucleic acid and two or more second linear nucleic acid molecules, wherein each second linear nucleic acid molecule comprises a nucleic acid encoding a different gRNA which targets a different site in the host cell genome. Each different second linear nucleic acid can recombine with the first linear nucleic acid to form two or more different, circular, extrachromosomal nucleic acids in the host cell. It is understood that the term "first linear nucleic acid" and "second linear nucleic acid" includes multiple copies of the same nucleic acid molecule. For example, the host cell can be contacted with two or more second linear nucleic acid molecules, wherein each second linear nucleic acid molecule comprises a nucleic acid encoding a different gRNA to target two, three, four, five, six, seven or more different sites in the host cell genome. In some embodiments, once the gRNA guides the RNA-guided endonuclease to two or more target sites, the endonuclease creates a break at the two or more target sites and two or more donor DNA molecules are integrated into the host cell genome via homologous recombination.

In some embodiments, the first linear nucleic acid comprising a selectable marker is a gapped vector comprising a pair of homologous flanking sequences that recombine with a pair of homologous sequences flanking the gRNA cassette in the second linear nucleic acid to form a larger circular vector where the gap has been repaired by inserting the second linear nucleic acid into the gapped vector. In some embodiments each homologous flanking sequence of the pair of homologous flanking sequences in the first nucleic acid contains a recombination region comprising a nucleotide sequence of sufficient length and sequence identity that allows for homologous recombination with the pair of homologous flanking sequences in the second linear nucleic acid, but not with other regions of the first or second linear nucleic acid participating in the in vivo assembly, nor with any genomic regions of the host cell. For in vivo assembly of marker/gRNA vectors via gap repair and for selection of cells capable of homologous recombination and gap repair, see, for example, Horwitz et al. (Cell Systems 1:88-96 (2015)) and WO2015/095804, both of which are incorporated herein in their entireties by this reference.

In some embodiments, the gRNA is introduced into the cell on circular extrachromosomal nucleic acid (i.e., a plasmid) that is not formed through homologous recombination of linear nucleic acid molecules. In these embodiments, the plasmid comprises a stability element of the invention. These embodiments are used, for example, when integration of a single donor DNA molecule is desired.

Using the methods provided herein, one or more target sites in a host cell genome can be modified with surprisingly high efficiency compared to conventional CRISPR/Cas systems. The efficiency of alteration in a population of cells can be at least about 5%, 10%, 15%, 20%, 25%, 30%, 35%, 40%, 45%, 50%, 55%, 60%, 65%, 70%, 75% or 80% or higher, or any percentage in between these percentages.

As used throughout, a guide RNA (gRNA) sequence is a sequence that interacts with an RNA-guided DNA endonuclease and specifically binds to or hybridizes to a target nucleic acid within the genome of a cell, such that the gRNA and the targeted nuclease co-localize to the target nucleic acid in the genome of the cell. Each gRNA includes a DNA targeting sequence of about 10 to 50 nucleotides in length that specifically binds to or hybridizes to a target DNA sequence in the genome. For example, the DNA targeting sequence is about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides in length. Each gRNA contains a gRNA scaffold sequence that binds to the RNA-guided DNA endonuclease that does not comprise the DNA targeting sequence. In some embodiments, the gRNA comprises a crRNA sequence and a transactivating crRNA (tracrRNA) sequence. In some embodiments, the gRNA does not comprise a tracrRNA sequence.

Generally, the DNA targeting sequence is designed to complement (e.g., perfectly complement) or substantially complement the target DNA sequence. In some cases, the DNA targeting sequence can incorporate wobble or degenerate bases to bind multiple genetic elements. In some cases, the 19 nucleotides at the 3' or 5' end of the binding region are perfectly complementary to the target genetic element or elements. In some cases, the binding region can be altered to increase stability. For example, non-natural nucleotides, can be incorporated to increase RNA resistance to degradation. In some cases, the binding region can be altered or designed to avoid or reduce secondary structure formation in the binding region. In some cases, the binding region can be designed to optimize G-C content. In some cases, G-C content is preferably between about 40% and about 60% (e.g., 40%, 45%, 50%, 55%, 60%).

Any RNA-guided DNA endonuclease can be used in the methods provided herein. In some embodiments, the RNA-guided DNA endonuclease is an active Cas9 endonuclease such that when bound to a target nucleic acid as part of a complex with a gRNA, a double strand break is introduced into the target nucleic acid. In some embodiments, the double strand break is repaired by HDR to insert a donor DNA molecule into the genome of the host cell. Various Cas9 endonucleases can be used in the methods described herein. For example, a Cas9 nuclease that requires an NGG protospacer adjacent motif (PAM) immediately 3' of the region targeted by the gRNA can be utilized. As another example, Cas9 proteins with orthogonal PAM motif requirements can be used to target sequences that do not have an adjacent NGG PAM sequence. Exemplary Cas9 proteins with orthogonal PAM sequence specificities include, but are not limited to, those described in Esvelt et al. (Nature Methods 10: 1116-1121 (2013)).

In some cases, the Cas9 protein is a nickase, such that when bound to target nucleic acid as part of a complex with a gRNA, a single strand break or nick is introduced into the target nucleic acid. A pair of Cas9 nickases, each bound to a different gRNA, can be targeted to two proximal sites of a target genomic region and thus introduce a pair of proximal single stranded breaks into the target genomic region. Nickase pairs can provide enhanced specificity because off-target effects are likely to result in single nicks, which are generally repaired without lesion by base-excision repair mechanisms. Exemplary Cas9 nickases include Cas9 nucleases having a D10A or H840A mutation (See, for example, Ran et al. "Double nicking by RNA-guided CRISPR Cas9 for enhanced genome editing specificity," Cell 154(6): 1380-1389 (2013)).

7.2 Site-Specific Nucleases

In some embodiments, modification of the target sites comprises methods which use extrachromosomal DNA molecules, which comprise a stability element of the invention and one or more nucleic acid sequence encoding a nuclease, as described in WO 2012/149470, which is incorporated herein by reference.

In these methods, a donor DNA molecule is introduced into a *Kluyveromyces* host cell, wherein the donor DNA comprises a nucleic acid of interest flanked by a first homology region and a second homology region. The first and second homology regions share homology with 5' and 3' regions, respectively, of the genomic target site. An extrachromosomal DNA comprising a stability element of the invention and a nucleic acid sequence encoding site-specific nuclease is also introduced to the host cell. The nuclease is capable of recognizing and cleaving a unique recognition sequence (also called a landing pad) within the target site. Upon induction of a double-stranded break within the target site by the site-specific nuclease, endogenous homologous recombination machinery integrates the nucleic acid of interest at the cleaved target site at a higher frequency as compared to a target site not comprising a double-stranded break. This increased frequency of integration obviates the need to co-integrate a selectable marker in order to select transformants having undergone a recombination event.

A variety of methods are available to identify those cells having an altered genome at or near the target site without the use of a selectable marker. In some embodiments, such methods seek to detect any change in the target site, and include but are not limited to PCR methods, sequencing methods, nuclease digestion, e.g., restriction mapping, Southern blots, and any combination thereof.

The methods of the invention can be used for simultaneous genomic integration of a plurality of exogenous nucleic acids of interest using a plurality of site-specific nucleases. These methods, for example, allow for the simultaneous integration of a plurality of genes in a single enzymatic pathway.

As in the case for gap repair embodiments described above, the donor DNA molecule may comprise any nucleic acid of interest. For example, the donor DNA molecule may comprise a gene of interest that can be knocked in to a host genome. In other embodiments, the donor DNA molecule functions as a knockout construct that is capable of specifically disrupting a target gene upon integration of the construct into the target site of the host cell genome, thereby rendering the disrupted gene non-functional. Examples of nucleic acids of interest include, but are not limited to, a protein-coding sequence, a promoter, an enhancer, terminator, transcriptional activator, transcriptional repressor, transcriptional activator binding site, transcriptional repressor binding site, intron, exon, poly-A tail, multiple cloning site, nuclear localization signal, mRNA stabilization signal, integration loci, epitope tag coding sequence, degradation signal, or any other naturally occurring or synthetic DNA molecule. In specific embodiments, the nucleic acid of interest does not comprise a nucleic acid encoding a selectable marker.

As noted above, a double-strand break at a selected target site is induced by site specific endonucleases, for example, site-specific recombinases, transposases, topoisomerases, and zinc finger nucleases, and include modified derivatives, variants, and fragments thereof. The nuclease cleaves the target site at a recognition sequence, that is specifically recognized and/or bound by a double-strand break inducing agent. The length of the recognition sequence can vary, and includes, for example, sequences that are at least 10, 12, 14, 16, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70 or more nucleotides in length.

In some embodiments, the recognition sequence is palindromic, that is, the sequence on one strand reads the same in the opposite direction on the complementary strand. In some embodiments, the nick/cleavage site is within the recognition sequence. In other embodiments, the nick/cleavage site is outside of the recognition sequence. In some embodiments, cleavage produces blunt end termini. In other embodiments, cleavage produces single-stranded overhangs, i.e., "sticky ends," which can be either 5' overhangs, or 3' overhangs.

The recognition sequence within the selected target site can be endogenous or exogenous to the host cell genome. When the recognition site is exogenous to the host cell genome, it may be introduced into the host cell genome by any means known to those of skill in the art. For example, the recognition sequence can be introduced using the gap-repair methods described above. The recognition sequence is typically recognized by a naturally-occurring double-strand break inducing agent. Alternatively, a recognition site could be recognized and/or bound by a modified or engineered double-strand break inducing agent designed or selected to specifically recognize the recognition sequence to produce a double-strand break. In some embodiments, the modified double-strand break inducing agent is derived from a native, naturally-occurring double-strand break inducing agent. In other embodiments, the modified double-strand break inducing agent is artificially created or synthesized. Methods for selecting such modified or engineered double-strand break inducing agents are known in the art. For example, amino acid sequence variants of the protein(s) can be prepared by mutations in the DNA. Methods for mutagenesis and nucleotide sequence alterations include, for example, Kunkel, (1985) *Proc Natl Acad Sci* USA 82:488-92; Kunkel, et al., (1987) *Meth Enzymol* 154:367-82; U.S. Pat. No. 4,873,192; Walker and Gaastra, eds. (1983) *Techniques in Molecular Biology* (MacMillan Publishing Company, New York) and the references cited therein. Guidance regarding amino acid substitutions not likely to affect biological activity of the protein is found, for example, in the model of Dayhoff, et al., (1978) *Atlas of Protein Sequence and Structure* (Natl Biomed Res Found, Washington, D.C.). Conservative substitutions, such as exchanging one amino acid with another having similar properties, may be preferable. Conservative deletions, insertions, and amino acid substitutions are not expected to produce radical changes in the characteristics of the protein, and the effect of any substitution, deletion, insertion, or combination thereof can be evaluated by routine screening assays. Assays for double strand break inducing activity are known and generally measure the overall activity and specificity of the agent on DNA substrates containing recognition sites.

Endonucleases useful in the present invention include homing endonucleases, which like restriction endonucleases, bind and cut at a specific recognition sequence. However the recognition sites for homing endonucleases are typically longer, for example, about 18 bp or more. Homing endonucleases, also known as meganucleases, are well known to those of skill in the art and have been classified into the following families based on conserved sequence motifs: an LAGLIDADG homing endonuclease, an HNH homing endonuclease, a His-Cys box homing endonuclease, a GIY-YIG homing endonuclease, and a cyanobacterial homing endonuclease. Examples of homing endonuclease useful in the present invention include , but are not limited to: H-DreI, I-SeeI, I-SceII, I-SceIII, I-SceIV, I-SceV, I-See VI, ISceVII, I-CeuI, I-CeuAIIP, I-CreI, I-CrepsbIP, I-CrepsbIIP, I-CrepsbIIIP, I-CrepsbIVP, I-TliI, I-PpoI, Pi-PspI, F-SceI, F-SceII, F-SuvI, F-CphI, F-TevI, F-TevII, I-AmaI, I-AniI, I-ChuI, ICmoeI, I-CpaI, I-CpaII, I-CsmI, I-CvuI, I-CvuAIP, I-DdiI, I-DdiII, I-DirI, I-DmoI, I-HmuI, IHmuII, I-HsNIP, I-LlaI, I-MsoI, I-NaaI, I-NanI, I-NclIP, I-NgrIP, I-NitI, I-NjaI, I-Nsp236IP, IPakI, I-PboIP, I-PcuIP, I-PcuAI, I-PcuVI, I-PgrIP, I-PobIP, I-PorI, I-PorIIP, I-PbpIP, ISpBetaIP, I-SeaI, I-SexIP, I-SneIP, I-SpomI, I-SpomCP, I-SpomIP, I-SpomIIP, I-SquIP, ISsp68031, I-SthPhiJP, I-SthPhiST3P, I-SthPhiSTe3bP, I-TdeIP, I-TevI, I-TevII, I-TevIII, IUarAP, I-UarHGPAIP, I-UarHGPA13P, I-VinIP, I-ZbiIP, PI-MgaI, PI-MtuI, PI-MtuHIP PIMtuHIIP, PI-PfuI, PI-PfuII, PI-PkoI, PI-PkoII, PI-Rma43812IP, PI-SpBetaIP, PI-SeeI, PI-TfuI, PI-TfuII, PI-ThyI, PI-TliI, or PI-TliII, or any variant or derivative thereof.

In some embodiments the nuclease is a TAL-effector DNA binding domain-nuclease fusion protein (TALEN). TAL effectors of plant pathogenic bacteria in the genus *Xanthomonas* play important roles in disease, or trigger defense, by binding host DNA and activating effector-specific host genes. The TAL-effector DNA binding domain may be engineered to bind to a desired target sequence, and fused to a nuclease domain, e.g., from a type II restriction endonuclease, typically a nonspecific cleavage domain from a type II restriction endonuclease such as FokI, HhaI, HindIII, Nod, BbvCI, EcoRI, BglI, and AlwI. Thus, in preferred embodiments, the TALEN comprises a TAL effector domain comprising a plurality of TAL effector repeat sequences that, in combination, bind to a specific nucleotide sequence in the target DNA sequence, such that the TALEN cleaves the target DNA within or adjacent to the specific nucleotide sequence. TALENS useful for the methods provided herein include those described in WO10/079430 and U.S. Patent Application Publication No. 2011/0145940.

In some embodiments the nuclease is a site-specific recombinase. A site-specific recombinase, also referred to as a recombinase, is a polypeptide that catalyzes conservative site-specific recombination between its compatible recombination sites, and includes native polypeptides as well as derivatives, variants and/or fragments that retain activity, and native polynucleotides, derivatives, variants, and/or fragments that encode a recombinase that retains activity. In some embodiments, the recombinase is a serine recombinase or a tyrosine recombinase. In some embodiments, the recombinase is from the Integrase or Resolvase families. In some embodiments, the recombinase is an integrase selected from the group consisting of FLP, Cre, lambda integrase, and R.

In some embodiments the nuclease is a transposase. Transposases are polypeptides that mediate transposition of a transposon from one location in the genome to another. Transposases typically induce double strand breaks to excise the transposon, recognize subterminal repeats, and bring together the ends of the excised transposon, in some systems other proteins are also required to bring together the ends during transposition. Examples of transposons and transposases include, but are not limited to, the Ac/Ds, Dt/rdt, Mu-Ml/Mn, and Spm(En)/dSpm elements from maize, the Tam elements from snapdragon, the Mu transposon from bacteriophage, bacterial transposons (Tn) and insertion sequences (IS), Ty elements of yeast (retrotransposon), Ta 1 elements from *Arabidopsis* (retrotransposon), the P element transposon from *Drosophila,* the Copia, Mariner and Minos elements from *Drosophila,* the Hermes elements from the housefly, the PiggyBack elements from *Trichplusia ni,* Tc1 elements from *C. elegans,* and IAP elements from mice (retrotransposon).

In some embodiments the nuclease is a zinc-finger nuclease (ZFN). ZFNs are engineered double-strand break inducing agents comprised of a zinc finger DNA binding domain and a double strand break inducing agent domain. Engineered ZFNs consist of two zinc finger arrays (ZFAs), each of which is fused to a single subunit of a non-specific endonuclease, such as the nuclease domain from the FokI enzyme, which becomes active upon dimerization.

7.3 Cell Culture

The *Kluyveromyces* host cells are cultured using methods well known to those of skill in the art. If a selectable maker is used, the cells are cultured for a period of time sufficient for expression of the selectable marker from the circularized extrachromosomal vector. In some embodiments where the selectable marker is a drug resistance marker, the culturing is carried out for a period of time sufficient to produce an amount of the marker protein that can support the survival of cells expressing the marker in selectable media. In certain embodiments, these conditions also select against the survival of cells not expressing the selectable marker. Selective pressure can be applied to cells using a variety of compounds or treatments that would be known to one of skill in the art. For example, selective pressure can be applied by exposing host cells to conditions that are suboptimal for or deleterious to growth, progression of the cell cycle or viability, such that cells that are tolerant or resistant to these conditions are selected for compared to cells that are not tolerant or resistant to these conditions. Conditions that can be used to exert or apply selective pressure include, but are not limited to, antibiotics, drugs, mutagens, compounds that slow or halt cell growth or the synthesis of biological building blocks, compounds that disrupt RNA, DNA or protein synthesis, deprivation or limitation of nutrients, amino acids, carbohydrates or compounds required for cell growth and viability from cell growth or culture media, treatments such as growth or maintenance of cells under conditions that are suboptimal for cell growth, for instance at suboptimal temperatures, atmospheric conditions (e.g., % carbon dioxide, oxygen or nitrogen or humidity) or in deprived media conditions. The level of selective pressure that is used can be determined by one of skill in the art. This can be done, for example, by performing a kill curve experiment, where control cells and cells that comprise resistance markers or genes are tested with increasing levels, doses, concentrations or treatments of the selective pressure and the ranges that selected against the negative cells only or preferentially over a desired range of time (e.g., from 1 to 24 hours, 1 to 3 days, 3 to 5 days, 4 to 7 days, 5 to 14 days, 1 to 3 weeks, 2 to 6 weeks). The exact levels, concentrations, doses, or treatments of selective pressure that can be used depends on the cells that are used, the desired properties themselves, the markers, factors or genes that confer resistance or tolerance to the selective pressure as well as the levels of the desired properties that are desired in the cells that are selected and one of skill in the art would readily appreciate how to determine appropriate ranges based on these considerations.

The culturing can be performed in a suitable culture medium in a suitable container, including but not limited to a cell culture plate, a flask, or a fermentor. In some embodiments, the culture medium is an aqueous medium comprising assimilable carbon, nitrogen and phosphate sources. Such a medium can also include appropriate salts, minerals, metals and other nutrients. In some embodiments, in addition to the selection agent, the suitable medium is supplemented with one or more additional agents, such as, for example, an inducer (e.g., when one or more nucleotide sequences encoding a gene product are under the control of an inducible promoter), a repressor (e.g., when one or more nucleotide sequences encoding a gene product are under the control of a repressible promoter). Materials and methods for the maintenance and growth of cell cultures are well known to those skilled in the art of microbiology or fermentation science (see, for example, Bailey et al., Biochemical Engineering Fundamentals, second edition, McGraw Hill, New York, 1986). Consideration must be given to appropriate culture medium, pH, temperature, and requirements for aerobic, microaerobic, or anaerobic conditions, depending on the specific requirements of the host cell, the fermentation, and the process. In some embodiments, the culturing is carried out for a period of time sufficient for the transformed population to undergo a plurality of doublings until a desired cell density is reached. In some embodiments, the culturing is carried out for a period of time sufficient for the host cell population to reach a cell density (OD600) of between 0.01 and 400 in the fermentation vessel or container in which the culturing is being carried out. In other embodiments, the culturing is carried for a period of at least 12, 24, 36, 48, 60, 72, 84, 96 or more than 96 hours. In some embodiments, the culturing is carried out for a period of between 3 and 20 days. In some embodiments, the culturing is carried out for a period of 1, 2, 3, 4, 5, 6, 7, 8, 9, 10, 11, 12, 13, 14, 15, 16, 17, 18, 19, 20 or more than 20 days.

In some embodiments of the methods described herein, the methods further comprise the step of eliminating the circularized extrachromosomal vector from the host cell, for example, once a selected host cell has been identified as comprising the desired genomic integration(s). Plasmid-based systems generally require selective pressure on the plasmids to maintain the foreign DNA in the cell. In some embodiments, elimination of a plasmid encoding the selective marker from a selected cell can be achieved by allowing the selected cells to undergo sufficient mitotic divisions such that the plasmid is effectively diluted from the population. Alternatively, plasmid-free cells can be selected by selecting for the absence of the plasmid, e.g., by selecting against a counter-selectable marker (such as, for example, URA3) or by plating identical colonies on both selective media and non-selective media and then selecting a colony that does not grow on the selective media but does grow on the non-selective media.

7.4 Host Cells

The methods of the invention can be used to modify one or more target sites in a *Kluyveromyces* host cell genome. The host cell can be any member of the genus *Kluyveromyces*, including, for example, *K. marxianus, K. lactis, K. aestuarii K. africanus, K. bacillisporus K. blattae, K. dobzhanskii, K. hubeiensis, K. lodderae, K. nonfermentans, K. piceae, K. sinensis, K. thermotolerans, K. waltii, K. wickerhamii,* and *K. yarrowii.*

7.5 Methods of Producing a Product of Interest

As noted above, the donor DNA can be used integrate any desired nucleic acid sequence into the genome of the *Kluyveromyces* host cell. Thus, the methods of the invention comprise culturing a host cell comprising one or more integrated donor DNA molecules of interest encoding one or more proteins of interest under conditions suitable for production of the protein and recovering the protein produced by the host cell. Methods for preparing purified proteins from cell cultures are well known to those of skill in the art. In some embodiments, the protein of interest is a protein selected from the group consisting of an antibody, an enzyme, a hormone, a growth factor, an anticoagulant, blood factors, an engineered protein, an interferon, an interleukin, a thrombolytic, a viral protein or a bacterial protein.

In some embodiments, one or more secretion signal sequences (e.g., two, three, four, five, six, seven, eight, nine, or ten secretion signal sequences) may be inserted in the donor DNA molecules. The secretion signal sequence encodes a secretion signal peptide that is recognized by the molecular machinery of the host cell, which then secretes the protein from the cell. The choice of a secretion signal peptide may depend on the type of the host cell.

In some embodiments, the nucleic acid sequence(s) encoding the polypeptide of interest may be codon optimized according to codon frequencies of the host cell. Using the codon with the highest occurrence frequency in the host cell may reduce unwanted mutations and improve translation efficiency. The donor DNA molecules may also include appropriate expression control elements known in the art, including promoters, enhancers, selection markers, and transcription terminators well known to those of skill in the art. Methods for expressing therapeutic proteins are known in the art. See, for example, Paulina Balbas, Argelia Lorence (eds.) *Recombinant Gene Expression: Reviews and Protocols* (*Methods in Molecular Biology*), Humana Press; 2nd ed. 2004 edition (Jul. 20, 2004); Vladimir Voynov and Justin A. Caravella (eds.) *Therapeutic Proteins: Methods and Protocols* (*Methods in Molecular Biology*) Humana Press; 2nd ed. 2012 edition (Jun. 28, 2012).

The methods and compositions described herein are also useful in introducing multiple modifications in the genome of the host cell and thus provide particular advantages for constructing recombinant organisms comprising optimized biosynthetic pathways, for example, towards the conversion of biomass into biofuels, pharmaceuticals or biomaterials. Functional non-native biological pathways have been successfully constructed in microbial hosts for the production of a number of valuable products, including precursors to the antimalarial drug artemisinin, fatty acid derived fuels and chemicals (e.g., fatty esters, fatty alcohols and waxes), methyl halide derived fuels and chemicals, polyketide synthases that make cholesterol lowering drugs, and polyketides.

Disclosed are materials, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutations of these compounds may not be explicitly disclosed, each is specifically contemplated and described herein. For example, if a method is disclosed and discussed and a number of modifications that can be made to one or more molecules including in the method are discussed, each and every combination and permutation of the method, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed compositions. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

8. EXAMPLE 1

8.1 Materials and Methods 8.1.1. Preparation of *K. marxianus* Host Strain for CRISPR-Cas A wild-type *K. marxianus* strain was used. A *S. cerevisiae* codon-optimized version of the *Streptococcus pyogenes* Cas9 gene was fused to an SV40 nuclear localization sequence designed and cloned into an integration cassette under the expression of the *S. cerevisiae* TEF1 promoter with a CYC1 terminator (Horwitz et al., 2015, *Cell Systems* (1): 88-96; DiCarlo et al. 2013, Nucleic Acids Res 2013 41(7) 4336-43); see sequence listing). The construct, marked with an hphA (hygromycin resistance) cassette, was stably integrated at the YYKU70 locus of wild-type *K. marxianus* strain. The integration construct has a nucleic acid sequence of SEQ ID NO: 23. Correct integration at YYKU70 locus was verified by colony PCR reactions.

8.1.2. Construction of Stable Plasmids for *Kluyveromyces*

New stable plasmids for replicating and/or expressing a gRNA or nucleases were prepared. The new stable plasmids contain *K. marxianus* specific stability element comprising a centromere sequence (CEN) and an autonomously replicating consensus sequence (ARS). Plasmid pAM028 contains the CEN/ARS sequences shown in SEQ ID NO:1. Plasmid pAM029 contains the CEN/ARS sequence shown in SEQ ID NO: 4. The "Old pKD1 element plasmid" shown in FIG. 1 has a pKD1 stability element from a pKD1 plasmid (Chen, Wesolowski-Louvel et al., *J Basic Microbiol* 28(4): 211-220, 1988) instead of the CEN/ARS sequences shown in SEQ ID NOs: 1 or 4.

Using homologous recombination, the stability element (comprising ARS/CEN sequence shown in SEQ ID NO:1) was cloned into a linearized vector containing a promoter driving RNA expression, terminator, chimeric gRNA sequence, origin of replication, bacterial and yeast antibiotic selection markers. The plasmid is referred to as *K. marxianus* gRNA entry vector (sequence shown in SEQ ID NO: 21). Once this plasmid was created and verified, it was used to generate a stable plasmid for meganuclease expression (sequence shown in SEQ ID NO: 22). A linear version of this plasmid was generated by PCR with the *K. marxianus* CEN/ARS, origin of replication, bacterial and yeast antibiotic selection markers. A PCR product containing the f-CphI open reading frame, promoter and terminator was also amplified and cloned into the linear fragment described above.

8.1.3. Guide-RNA Expression Cassettes

Cas9 protein is targeted to cut sites by association with a generic structural RNA and a specific targeting RNA. The standard "chimeric" configuration was adopted, in which the targeting and structural RNAs are fused to create a single gRNA. Expression of the gRNA construct was driven by the SNR52 polymerase III promoter, with a SUP4 terminator. The gRNA cassette was cloned into low copy, stable vector using the *K. marxianus* chromosome V CEN/ARS elements by gap repair directly into a Cas9-expressing host strain (Orr-Weaver et al., 1983). The low copy, stable vector for gRNA entry has a sequence shown in SEQ ID NO: 21. In order to gap repair the gRNA cassette/s directly into the expression vector in the host strain, we first generated full-length gRNA cassettes with 500 bp flanking homology to the linearized vector. In certain embodiments, we co-transformed host cells with single or multiple DNA fragments (for multiplexing) containing gRNA cassettes bearing flanking homology to the linear plasmid.

8.1.4. Selection of Target Sites and Generation of Donor DNA

Candidate CRISPR target sites inside the targeted open reading frames (ORFs) were identified based on the presence of a PAM sequence N(19)NGG. The following genomic loci were selected as target sites: NDT80, YKU80, GAS2, GAL80, and LEU2. The gRNA sequences for these target sites are shown as SEQ ID NOs: 15-20. Donor DNA constructs with 500 bp of flanking homology were generated using standardized linkers for assembly as described in U.S. Pat. No. 8,110,360, which is hereby incorporated by reference in its entirety. See also, Horwitz et al. 2015.

8.1.5. *K. marxianus* Transformation Protocol and Genomic Integrations of Markerless DNA The *K. marxianus* transformation protocol we developed was a variant of the Gietz et al. 2007 (*Nat Protoc* 2:31-34) adapted for these strains. After 1-2 days growth on agar plates, single colonies were picked and used to inoculate 3 ml of liquid rich media (e.g., YPD). This liquid culture was growth overnight with shaking and then diluted into fresh media the next morning to an OD of 0.05-0.2. The diluted culture was grown with shaking incubation until an OD of 0.6-0.9, undergoing a minimum of two doublings. 5 ml of culture was harvested for each transformation, centrifuged to precipitate cells (7000×g, 2 minutes) and then resuspended in an equal volume of sterile water. Centrifugation was repeated, and cells were resuspended in 100 mM lithium acetate. Centrifugation was repeated one last time, and cells were resuspended in 100 mM lithium acetate at a volume 250-fold lower than the original volume (e.g., 20 μl for an original volume of 5 ml). To each transformation, 240 μl of 50% PEG solution, 36 μl of 1.5M lithium acetate, 10 μl of boiled salmon sperm DNA, 54 μl transformation DNA mixed with water and 20 μl cell mixture were added. The transformation mixture was briefly vortexed to distribute cells and reagents evenly, followed by incubation at 30° C. for 30 minutes then 42° for 40 minutes. After heat shock, the transformation mixture was centrifuged again at lower speed (3000×g, 2 minutes), followed by aspiration of the PEG suspension and resuspension of the cell pellet in 2 ml liquid rich media. This culture was then incubated with shaking overnight followed by plating onto selective media. Each marker-less integrations were confirmed using a colony PCR.

8.2 Results and Discussion 8.2.1. Establishment of High-Efficiency, High Throughput Integrations in *Kluyveromyces* Using CRISPR-Cas The molecular biology tools available for *Kluyveromyces marxianus* (KM) genetic engineering were not as robust as those used in *Saccharomyces cerevisiae* (SC). Currently, only one report of CRISPR use in *K. marxianus* for knockouts reliant upon random mutation has been published in the literature. (See Löbs et al. CRISPR-Cas9-enabled genetic disruptions for understanding ethanol and ethyl acetate biosynthesis in *Kluyveromyces marxianus.* 2017. Biotechnology for Biofuels). A high-throughput method would require higher rates of marker-less knockout/integration if markerless, multiplex engineering in *K. marxianus* would be achieved. As used herein, the term "markerless" refers to integration of a donor DNA into a target site within a host cell genome without accompanying integration of a selectable marker. In some embodiments, the term also refers to the recovery of such a host cell without utilizing a selection scheme that relies on integration of selectable marker into the host cell genome. For example, in certain embodiments, a selection marker that is episomal or extrachromasomal may be utilized to select for cells comprising a plasmid encoding a nuclease capable of cleaving a genomic target site. Such use would be considered "markerless" so long as the selectable marker is not integrated into the host cell genome.

The first step toward obtaining higher transformation efficiencies was construction of a more stable plasmid. Previously, a plasmid containing a pKD1-element from *K. lactis* was used in *K. marxianus,* and transformants were obtained, but the plasmid was unstable (FIG. 1, top right). Colonies transformed with this plasmid showed evidence of colony sectoring, as small colonies with rough edges are formed when the plasmid is lost at high frequency. Two new plasmids pAM028 and pAM029 containing *K. marxianus*-specific CEN/ARS sequences (SEQ ID NO: 1 and SEQ ID NO: 4, respectively) were made (FIG. 1, top left and bottom right). The CEN/ARS sequences were incorporated to generate stable plasmids. Colonies transformed with these plasmids are large, round, and smooth, indicating stable expression of the antibiotic-resistance cassette. In addition, plasmids can be recovered from these colonies, demonstrating that the new plasmids are maintained and not integrated.

The second step towards high genomic integration efficiency was achieved by reducing or eliminating genomic double-strand break repair via NHEJ. NHEJ relies on the YKU complex (a heterodimer of YKU70 and YKU80 proteins) and DNA ligase. By deleting YKU70, the level of NHEJ was greatly reduced. "Gap repair" of plasmids by homologous recombination was achieved. (see FIG. 2). Plasmid gap repair occurs when multiple overlapping linear fragments generate an intact, selectable circular vector (see, WO2015/095804, which is incorporated herein by reference).

Together, a stable plasmid and elimination of NHEJ led to the first high-efficiency markerless integration in *K. marxianus* using CRISPR-Cas. In this example, three components were used for efficiently targeted integrations or deletions using CRISPR-Cas: expressed Cas9 protein, gRNA specific for the targeted locus, and donor DNA for repair of the induced double-strand break. A construct for Cas9 expression was previously integrated into a *K. marxianus* strain, disrupting the YKU70 locus. A chimeric gRNA was expressed from a Nat-marked *K. marxianus* plasmid using the *Saccharomyces cerevisiae* pSNR52 promoter and SUP4 terminator. (See Horwitz et al., 2015, *Cell Systems,* (1)88-96). Donor DNA was supplied as linear MssI-digested fragment with 500 bp of GAL80 upstream and downstream homology flanking a GFP expression construct. When Donor DNA was not supplied, no colonies were recovered. When donor DNA was supplied, many colonies grew. (Data not shown). This phenotype is indicative of double-strand breaks induced by gRNA expression at a single location (GAL80) repaired by homologous recombination with the supplied donor DNA construct. cPCR of 24 colonies of marker-less integration at GAL80 show that 22 out of 24 colonies correctly integrated donor DNA at the target sites. In other words, 92% of the colonies tested by cPCR successfully integrated the GFP sequence in place of the GAL80 open reading frame (ORF).

8.2.2. CRISPR-Mediated Multiplex, Markerless, Simultaneous Genomic Integration in *K. marxianus* Host Cells Several gRNAs for new loci were identified that gave high efficiency, marker-less integration in *K. marxianus* with CRISPR-Cas system: NDT80, YKU80, GAS2, LEU2, and GAL80. 96-well transformations were performed using the same basic protocol described above. PCR-generated linear gRNA cassettes were co-transformed with PCR-generated linear selectable marker-marked *K. marxianus* vector. 24 colonies of each type of 1 and 2-locus integration and 32 colonies of each type of 3-locus integrations were verified by colony PCR (cPCR). Rates of successful integration at all attempted loci were 94% at one locus, 34% at two loci and 7% at three loci. 368 colonies were screened by colony PCR. Among these colonies screened, a small proportion of cases (about 5%), no PCR fragment bands were observed on a gel, and these colonies were not included in the calculation of integration efficiencies.

TABLE 1

| Targeted Loci | Description of Integration | Integration Type | Integration Efficiency |
|---|---|---|---|
| GAL80 | marker-less integration with simultaneous gene deletion | Single | 100% |
| KU80 | marker-less integration with simultaneous gene deletion | Single | 88% |
| NDT80 | marker-less integration with simultaneous gene deletion | Single | 96% |
| GAS2 | marker-less integration with simultaneous gene deletion | Single | 96% |
| GAL80, NDT80 | marker-less integration with simultaneous gene deletion | Double | 61% |
| GAL80, GAS2 | marker-less integration with simultaneous gene deletion | Double | 52% |
| NDT80, GAS2 | marker-less integration with simultaneous gene deletion | Double | 41% |
| GAL80, KU80 | marker-less integration with simultaneous gene deletion | Double | 22% |

TABLE 1-continued

| Targeted Loci | Description of Integration | Integration Type | Integration Efficiency |
|---|---|---|---|
| NDT80, KU80 | marker-less integration with simultaneous gene deletion | Double | 38% |
| KU80, GAS2 | marker-less integration with simultaneous gene deletion | Double | 21% |
| GAL80, NDT80, KU80 | marker-less integration with simultaneous gene deletion | Triple | 7% |
| GAL80, NDT80, GAS2 | marker-less integration with simultaneous gene deletion | Triple | 0% |
| GAL80, KU80, GAS2 | marker-less integration with simultaneous gene deletion | Triple | 6% |
| NDT80, KU80, GAS2 | marker-less integration with simultaneous gene deletion | Triple | 13% |

8.2.3. High-Efficiency Multiplex Integrations in *Kluyveromyces* Using Meganuclease CRISPR-Cas system can provide a highly efficient method for multiplex insertion or deletion of genes. However, each locus requires a unique gRNA, increasing the number of components required for each transformation as the number of target loci increases. F-CphI is a meganuclease that cuts a specific 24 bp recognition sequence ("landing pad"). This sequence can be inserted at multiple locations in the genome. Transformation and selection for a single plasmid expressing F-CphI then leads to double-strand breaks at all recognition sites, followed by repair of these breaks by donor DNA containing homologous ends.

A *K. marxianus* plasmid expressing F-CphI was constructed and tested in several *K. marxianus* strains. This plasmid was shown to facilitate the excision of antibiotic resistance cassettes flanked by cut sites with sequence repeats and the integration of genes at one, two and three loci in pre-constructed strains. In all cases, the desired genotype was obtained with high efficiency, and colony numbers reduced as more loci were engineered simultaneously. For excision of antibiotic resistance cassettes, 100% of tested colonies successfully removed the cassette. Similarly, 100% of tested single landing-pad colonies integrated the desired DNA, 96% of double landing-pad colonies, and 20% of triple landing-pad colonies. Triple landing-pad strains produced very few colonies (<15/transformation), and were much more variable in integration efficiency (16-100% depending on the transformation).

TABLE 2

| Targeted Loci | Description of Integration | Integration Type | Integration Efficiency |
|---|---|---|---|
| KU80 | marker-less integration into f-CphI landing pad | Single | 99% |
| KU80, GAS2 | marker-less integration into f-CphI landing pad | Double | 56% |
| KU80, GAS2, GAL80 | marker-less integration into f-CphI landing pad | Triple | 8% |

8.2.4. Compatibility of SC Codon-Optimized Genes and Promoters in *Kluyveromyces*

Compatibility of SC codon-optimized genes and promoters were tested in *K. marxianus*. *K. marxianus* was transformed with a SC codon-optimized nucleic acid encoding fluorescent proteins operably linked by the SC pGAL1/10 bidirectional promoter. Two *K. marxianus* strains were made, one with the SC pGAL1/10 promoter driving GFP and RFP expression, and one with the *K. marxianus* pGAL1/10 promoter driving GFP and RFP expression. These constructs were integrated at the GAL80 locus (deleting the GAL80 ORF), and fluorescence was measured in a Tecan plate reader during log-phase growth. Both GFP and RFP were present at similar levels, indicating that in this case, *Saccharomyces cerevisiae* codon optimization and pGAL1/10 promoter expression were functional. (Data not shown).

The results shown in the Example section illustrate that *Kluyveromyces* is highly engineerable, allowing multiple genomic integration of heterologous nucleic acids simultaneously. Compared to CHO cells which have a doubling time of about 19-24 hours and a total genetic engineering cycling time (from one transformation to the next transformation) of about three months, *Kluyveromyces* has a cell population doubling time of about 2 hours and a total cycling time of about two weeks with the new stable plasmids provided in the present invention. The compositions and methods provided herein provide a large step forward in our ability to engineer *Kluyveromyces* for the production of new biomolecules.

9. EXAMPLE 2

This example presents results of experiments using the stability elements in Table 3. The experiments were carried out generally as described above in Example 1, using the same strain used in Example 1 (referred to as Strain 1) and a second wild-type *K. marxianus* strain (referred to as Strain 2). The results show successful marker-less triple integrations with three CEN/ARS sequences (CEN/ARS_2, 3 and 5). Rates of triple integration with the CEN/ARS_2, 3 and 5 were 3%, 13% and 3% respectively (of n=30 colonies tested). Rates in Strain 1 are those directly comparable to those found in Example 1. Strain 2 had similar rates of triple integration but did not recapitulate the original data for CEN/ARS_1.

TABLE 3

| CEN/ARS | Length | Genome Location |
|---|---|---|
| CEN/ARS_1 SEQ ID NO: 1 | 1259 bp | Chr 5 Strain 1 |
| CEN/ARS_2 SEQ ID NO: 4 | 1205 bp | Chr 6 Strain 1 |
| CEN/ARS_3 SEQ ID NO: 7 | 2234 bp | Chr 3 Strain 1 |
| CEN/ARS_4 SEQ ID NO: 13 | 1256 bp | Chr 5 Strain 2 |
| CEN/ARS_5 SEQ ID NO: 14 | 232 bp | Chr 2 |
| CEN/ARS_6 SEQ ID NO: 10 | 1157 bp | Chr 4 Strain 1 |

9.1 Materials and Methods 9.1.1. Computational Search for Additional CEN/ARS Sequences We searched the *K. marxianus* genome for three sequence elements (CDE1, CDE2, ARS) within 4000 bp of each other. Each sequence was allowed mismatches, with total homology as low at 5 bp. The percentage of A/T nucleotides was required to be greater than or equal to 60%. We identified 4 chromosomal sequences with this method (CEN/ARS_1

(SEQ ID NO: 1), CEN/ARS_2 (SEQ ID NO: 4), CEN/ARS_3 (SEQ ID NO: 7), and CEN/ARS_6 (SEQ ID NO: 10)). CEN/ARS_5 is published in Cernak and Estrela, bioRxiv doi:10.1101/353680.

9.1.2. Strains, Gene Loci, gRNA and Donor DNA

Wild-type Strains 1 and 2 were transformed with gRNA vectors containing CEN/ARS elements to confirm CEN/ARS activity in maintaining the plasmid. For CRISPR-Cas engineering, we used the Cas9-integrated strains to perform single, double and triple integrations.

Three *K. marxianus* gene loci, GAS2, GAL80 and NDT80, were chosen to test the efficiency of CRISPR-Cas engineering. Their corresponding donor DNA fragments contain upstream and downstream sequences of each gene, resulting in gene knockout if successfully integrated. The gRNA sequences for each locus were as follows: GAS2 (SEQ ID NO: 16), GAL80 (SEQ ID NO: 20) and NDT80 (SEQ ID NO: 19).

9.1.3. Preparation of Nucleic Acids and Transformations

Plasmid containing gRNA or donor DNA was extracted from *E. coli* culture by miniprep. Using miniprepped plasmid as template, high-fidelity PCR (Phusion polymerase, NEB) was carried out to amplify both gRNAs using primers SEQ ID NO: 24 and SEQ ID NO: 25 (Table 4), and donor DNA fragments were prepared as described in Section 8.1.4, above. Linear gRNA vector was generated by PCR (primers SEQ ID NO: 26 and SEQ ID NO: 27 in Table 4) followed by gel-extraction. Transformations were carried as described in Section 8.1.5, above.

backbone) showed relatively low background colony count, as well as transformations with gRNA but without donor DNA. As the number of loci increased for simultaneous integration, fewer colonies were observed. In addition, transformation with CEN/ARS_3 resulted in small, sectoring colonies, which is in consistent with the stability experiment (FIG. 3). Similar to CEN/ARS_3, transformation with CEN/ARS_5 vector also showed small, sectoring colonies (FIG. 5).

Colony PCR was performed to screen for successful integrations at each locus. For single and double integrations, 12 colonies were screened. 30 colonies were tested for triple integrations due to the low integration rate. Results for cPCR screening are shown in FIGS. 6 and 7. In general, a high rate of successful single integration ranging from 75%~100% was observed, with vast majority of the single-locus integration rate at above 90%. Positive rate for double integration was generally from 25%~58%. CEN/ARS_1, CEN/ARS_2, CEN/ARS_3, CEN/ARS_5 all demonstrated successful triple integrations. CEN/ARS_3 showed the highest triple integration rate at ~13%. From the results of the stability test (FIG. 3) and CRISPR-Cas multiplexing, CEN/ARS_3 was considered to be a weak element in maintaining plasmid stability. Here the results indicates that the relationship between transformation efficiency and plasmid stability could be much more sophisticated. Besides Strain 1, Strain 2 also showed integration at all three loci at a rate ranging from 3% to 7% for CEN/ARS_2, CEN/ARS_3 and CEN/ARS_5.

TABLE 4

| SEQ ID NO | gRNA sequence | purpose |
|---|---|---|
| SEQ ID NO: 24 | CCTTATAAATCAAAAGAATAGACCGAGATAGG | gRNA amplification |
| SEQ ID NO: 25 | TGTTGTGTGGAATTGTGAGCGG | gRNA amplification |
| SEQ ID NO: 26 | GTTTTAGAGCTAGAAATAGCAAGTTAAAATAAGGC | Linear gRNA vector PCR |
| SEQ ID NO: 27 | CGATCATTTATCTTTCACTGCGGAG | Linear gRNA vector PCR |

9.2 Results 9.2.1. gRNA Vector Stability with New CEN/ARS Elements

In order to test the stability of plasmids containing different CEN/ARS elements. We transformed both Strain 1 and Strain 2 with each CEN/ARS-carrying plasmid. One plasmid that carries a PKD-1 element, as described above, was also tested. Plasmids with CEN/ARS_1, CEN/ARS_2 and CEN/ARS_5 resulted in large, round colonies with smooth edge (FIG. 3). On the other hand, plasmids with CEN/ARS_3, CEN/ARS_5 and PKD1 element gave rise to small and sectoring colonies, suggesting a weaker activity in maintaining plasmid stability. In addition, transformation with plasmid containing CEN/ARS_6 showed no colonies on the plate. This indicates that this computationally predicted CEN/ARS sequence may not have an actual activity. Similar phenotype regarding to colony shape and size was observed in both strains.

9.2.2. CRISPR-Cas Markerless Multiplex Transformation in *K. marxianus*

Three loci, GAS2, NDT80 and GAL80, were chosen for CRISPR-Cas-mediated integration. The 96-well transformation set-up is shown in FIGS. 4 and 5. As it is shown, strain control (no DNA construct) and plasmid control (only vector In summary, we have shown that using the new CEN/ARS elements, we are able to achieve simultaneous multiplex integration in *K. marxianus.*

One or more features from any embodiments described herein or in the figures may be combined with one or more features of any other embodiment described herein in the figures without departing from the scope of the invention.

All publications, patents and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

Informal Sequence Listing:

SEQ ID NO: 1 (CEN/ARS 1)
Centromeric DNA elements (CDE) are underlined.
Centromere sequence (CEN) is in bold. (SEQ ID NO: 2)
ARS consensus sequence is double underlined. (SEQ ID NO: 3)

```
         1         11         21         31         41
        GGATCCGATC TCCTTTCATT TCTGATAAAA GTAAGGCTTC TCTATTTACC

   51   TTTTAACCTA CATATTCATA GTTGGAAGTT ATCCTTCTAA GTACGTATAC

  101   AATATTAATT CAACGTAAAA ACAAAACTTA CTGTAAATAT GTGTAAAAAA

  151   AATCTATTAA ATTCATGGCA GTTTCAAGAA AAGAAAACTA TTATGGTCTG

  201   G**TCACGTGTA TACAAATTAT TAATTTTAAA ACTATATAAT TTATTATTTT**

  251   **TTTATTTTGA AGTTTAGAGT AATTTTAGTA GTATTTTATA TTTTAAATAA**

  301   **ATATGCTTTA AATTTTTACT TAATATTTTA TTATTTTTAA ATACAACGTT**

  351   **TTTATTTAAA ACAAAATTAT AAGTTAAAAA GTTGTTCCGA AAGT**AAAATA

  401   TATTTTATGG GTTTTACAAA AATAAATTAT TTTTAATGTA TTTTTTTAAT

  451   TATATTTTTG TATGTAATTA TATCCACAGG TATTATGTTG AATTTAGCTG

  501   TTTTAGTTTA CCTGTGTGGT ACTATGATTT TTTTAGAACT CTCCTCTTAG

  551   AAATAGGTGG TGTTGCGGTT GACTTTTAAC GATATATCAT TTTCAATTTA

  601   TTTATTTTAA AGTGACATAG AGAGATTCCT TTTAATTTTT TAATTTTTAT

  651   TTTCAATAAT TTTAAAAATG GGGGACTTTT AAATTGGAAC AAAATGAAAA

  701   ATATCTGTTA TACGTGCAAC TGAATTTTAC TGACCTTAAA GGACTATCTC

  751   GAACTTGGTT CGGAAATCCT TGAAATGATT GATATTTTGG TGGATTTTCT

  801   CTGATTTTCA AACAAGTAGT ATTTTATTTA ATATTTATTA TATTTTTTAC

  851   ATTTTTTTAT ATTTTTTTAT TGTTTGGAAG GTAAAGCAAC AATTACTTTC

  901   AAAATATATA AATCAAACTG AAATACTTAA TAAGAGACAA ATAACATTCA

  951   AGAATCAAAT ACTGGGTTAT TAATCAAAAG ATCTCTCTAC ATGCGCCCAA

 1001   ATTCACTATT TAAATTTACT ATACCACTGA CAGAATATAT GAACCCAGAT

 1051   TAAGTAGCCA GAGGCTCTTC CACTATATTG AGTATATAGC CTTACATATT

 1101   TTCTGCGCAT AATTTACTGA TGTAAAATAA ACAAAAATAG TTAGTTTGTA

 1151   GTTATGAAAA AAGGCTTTTG GAAAATGCGA AATACGTGTT ATTTAAGGTT

 1201   AATCAACAAA ACGCATATCC ATAGTGGATA GTTGGATAAA ACTTCAATTG

 1251   ATGCGGCCGC
```

SEQ ID NO: 4 (CEN/ARS 2)
Centromeric DNA elements (CDE) are underlined.
Centromere sequence (CEN) is in bold. (SEQ ID NO: 5)
ARS consensus sequence is double underlined. (SEQ ID NO: 6)

```
         1         11         21         31         41
        GATCCAAGTC TGAAGGTTGG TTTGGCACTA ACTTTACTCT TGTTATATTC

   51   AGAATTGTAT CAAGTTTATT TGGTAGAGTG GAGCCTTTTT TTATCCGTAA

  101   CACTTTTTCC CTGCTCCATT TTGAAAAACG ATTTCAGGCC ATCTTGGCTA

  151   TTCCGAATGA ATTTGGAATA TGTTTAAATT AATAAAAATA AAATAAAATA

  201   AAATAAAATA AAATAAAAAT TAAATCAAAT TAAATTAAAT TAAATTAAAT
```

-continued

```
 251 TAAATTAAAT TAAATAAAAA TAAATACAAC CAATACAACA TGGTAATATT

 301 CTTGCATCGT AATGAATATT AAATATCACT TTATTAATCT CATCATGTTT

 351 TATTGTTTTT GTAAGGACTT TAATATATTT GAATCAATAT TCTTTCAATT

 401 ACTAGTACTT TTTTTATATG ACTAAAATTG TTACACATTG GACTGACAGT

 451 AATTTTTAAA ATTTATGATT TATTCTTACT TTATATCTTT AAAAGTAGAA

 501 ATATTATACG GACGCTTTGA ATACAATTGA CAACTTATCT TACTAGTGTG

 551 AATCAACCCT ATCGATGTAG TACTCTTAAA ATACGGCCTT CTTGATAAAG

 601 TGTTAAATTC ATTTGGGTAA TGATTTTTCG AAAACCACAT TGAATGAACG

 651 ATCTAAATAA ATATAGGATG CAAAAGCATT TTAATAATTC AGAAACAAAC

 701 AAATTATTAA ACAGGAGCAG TTGAACGGTA TGTTAGCGAG TTTTGTAAAG

 751 GGTGAGTACA TTTATAGCTC TATTGAACAT AATAAATACA TATAAATAGT

 801 ATTTTTTGAC CCTCTATGAA GATGGCTTAC CAGCAACTTA TGTCTTTTAA

 851 TTCACGTGAC TACTAAACAA AAAAATATGT TATTTAAAAA ATATTTATTT

 901 AAATTTTTAA ACTATTATAG ATTATTTGTG AATGCATTAT TTTTTAATTT

 951 ATTAATTAAA AGAATTGCTA TTTACTTAAA ATAAGAATAA AAGCTTTTTA

1001 TTTTTTTAAA AGAAAAATAT ATTAAAAACA CTTTTCCGAA AGTTAAAATA

1051 ATTTTATATT TATCGGTAGC TGCAATTTAT AGACATAATA TTTTATATTT

1101 TTTAAAATTT ATTATTATTT TGTTTGAAAT AATAACGTCG GTGAGTGTTT

1151 AAGGTGAACT AAGACTGAAA AAGTACATAA TTTTTGTTAA TTTTATGATA

1201 TGATC
```

SEQ ID NO: 7 (CEN/ARS 3)
Centromeric DNA elements (CDE) are underlined.
Centromere sequence (CEN) is in bold. (SEQ ID NO: 8)
ARS consensus sequence is double underlined. (SEQ ID NO: 9)

```
   1          11         21         31         41

   AACAGATTGG TGGGTGGTCA ACGCACAAGC GATATCCCAA CACAGTCGGA

  51 AAAACTCTCG TTCATTCCAA AACTGATTGC TTCAGATCAC AACTCCGCTG

 101 GAGAAGATGA GTCCGTCACT TTCTTTCAAG ATTTGATTAA CGTTGATCGT

 151 TTGAAACGTC TCAGAAATGT CACTGGTATG TCTATCGAAA TCGTGCTTGG

 201 GACGCATAGA GAAATCCCAC AGCAACAGCA GCAGCAGCAG GAGTCACCTG

 251 TAGCAGAAGG TGTTCCGGTC GCCCAGGATA ATGGACATGT AACCACGAAC

 301 GACAATGCGG CAAATACTTC ATTGGAAGAA CCAAGTTCAC CCATTGACCA

 351 GGTTTATGGA TACCTCCTAC AACAGAACAT GTCTACGTTG CCAGAAGTTA

 401 CACTTTCGGA AAGTGATATC GCTATGAGCT ACCCGACGGA TCCAGTACCC

 451 TCTTACAGCA GCAACTTTAA CAACTTTGCT CTGCCTACTA TTGCCGATGA

 501 CAAACAAGAA TTAGAACAGA TGAGATTAAA GGAGCTAGAA AGTGAACCTC

 551 CTATCTGAAC ACTTAACGAG AAATATTTAT ATGTGTGTTT TTGTTTGTAT

 601 GTATGTATGT ATGTATGCCT GTGTATCATT AAATATATTA GCGGATCCCG

 651 GAGTTTTTAT TATCGTGTTC TTTTCATTAT ATAGTGAACC TAAAGTGACT
```

-continued

701 TTCAATTCCA AATTATGGAA AGATTCCTGG CATTATGCCT TATAATAATC

751 ACTTGTTTAC AACATTCCAT TAACAACACA TGTACACTCA AATTCCATTC

801 CATAAAACCA AAAAAAACCT TATTGAATTC TCCAGACCTC TCTGTCGGCT

851 TGACTTTGCT TGCTCAATTC GCGTTTGGCT GAAGATCACT CCAGAACCTA

901 GGACGTCATT ATTGAAATCT GATCACGTGA TTCGCATATT CATATAGACG

951 TATATTTTTC GCCACTTTTC TCTCTTGAAA AAAAGTTGTG CTAGATGAAC

1001 TTTGAGAACA AAACACATTG AAAGAAAAGT GGAACATTAT AATAATTGGA

1051 AAGAATAGTA GATTGGGTGG CCAAGTGGAA GAATTTAGTA ACTTTAGTGG

1101 TTAGAGCTTG TTTGAACGAC CAATCCAGTA AACTAATCAA CCATTGAACA

1151 ATGAGTATTC CTATCTTTGG AGATCAAGTT ACCGAAGAGA GAGCAGAAAA

1201 TGCTCGTATG AGTGCCTTTG TTGGTGCCAT CGCCGTTGGT GATCTAGTGA

1251 AAACTACACT AGGTCCAAAA GGTATGGATA AGTTACTTCA AAGTGCATCC

1301 AATAGCTCGA GTTTGGTTAC AAACGATGGT GCTACCATTC TAAAATCTAT

1351 TCCTTTGGAC AACCCTGCTG CCAAGGTGCT TGTTAACATC AGTAAAGTGC

1401 AAGATGATGA AGTTGGTGAC GGTACAACAA GTGTTACTGT TCTAAGTGCA

1451 GAATTATTGA GGGAAGCTGA AAAACTTGTT GAACAAGGCA GAATTCACCC

1501 ACAAACTATC ATCGAGGGTT ACAGAATTGC TTCTGCTGCT GCCCTCTCTG

1551 CATTGGAAAA GGCTGCTGTG GACAACTCCA AGAATAAAGA AGAATTTTAC

1601 AATGATTTGA TCAGCATCGC CAACACAACG CTATCTTCTA AAATTCTATC

1651 TCAAGATAAG GCTCACTTCT CTAAGTTGGC TACCGATGCT ATCTTAAGAT

1701 TAAAGGGCTC TACGAACTTG GAACACATTC AAATTATTAA GATCATTGGT

1751 GGTAAATTAT CGGATTCTTT CCTAGATGAA GGTTTCATTT TGCCAAAGAG

1801 ATTTGGTACC AACCAACCAA AACGTGTTGA AAATGCGAAG ATTTTGATTG

1851 CCAACACTTC TCTAGATACA GACAAGGTTA AAATCTTTGG TACCAAATTT

1901 AAGGTCGACT CTACTTCCAA GTTAGCTGAA CTAGAAAAAG CTGAGCGTGA

1951 AAAAATGAAG AGAAAGATAG AAAAGATTGC ACAATTCAAC ATTAATACCT

2001 TTATCAACAG ACAATTAATC TATGACTACC CTGAACAGAT GTTTACCGAC

2051 ATGGGTATCA ACTCCATCGA ACATGCTGAC TTTGAAGGTG TTGAAAGATT

2101 AGCACTTGTC ACTGGCGGTG AGGTTGTTTC TACATTTGAC AACCCAGAAA

2151 AATGTAAGCT AGGTGAATGT AAGTTGATCG AAGAAGTTAT AATTGGTGAG

2201 GAAATCTTTA CTAAATTTAC CGGGTGCAAG TCTGGTGAAG CTTGTACCAT

2251 TGTTCTAAGG GGTGCCACTG AGCAAGTCTT GGATGAAGCA GAAAGATCTC

2301 TACATGATGC CCTATCTGTT CTTTCCCAAA CAACAAAGGA GACTAGAACC

2351 GTTCTTGGTG GTGGTTGTGC AGAAATGATA ATGTCTAAAG CAGTTGATAC

2401 TGCAGCTCAA A

-continued

SEQ ID NO: 10 (CEN/ARS 6
Centromeric DNA elements (CDE) are underlined.
Centromere sequence (CEN) is in bold. (SEQ ID NO: 11)
ARS consensus sequence is double underlined. (SEQ ID NO: 12)

```
        1          11         21         31         41

        TCAATTACAA AGGGTGGAAA GTGATGGGGG GAATATCATC TGCACAATTT

     51 TGGCTCGCTT TATATAGTGC CGAGATTAGT AGGGTCTGGA TAAAAAAGCG

    101 AAGGAGAATA GGAAGAGGAA GAAAATTTTT TTTCTTCCTC TTTGAAAGGC

    151 CGGGTAACAA AGTCTCATCG TCCTCCAACC TAGGGCTTTC CTTTCCGCTT

    201 TTTTTTTCTT CTTCTCCTCC AAACAAGACC CAACCATACA CACCCACACA

    251 GACAGAAGAA AAAGTGTAAG GATGAGCGTT GTGTCGTTTT TTTTTTTTTT

    301 TTTTTTTTTT TTGGCGGAGA ATGTGTGCAC GTGCACAGAC ACACACGGGA

    351 GCGGCTGTGC CTCCGTATAC GGCAACTGCC ACGACAACCG AGGGCACAGA

    401 TACACGAGGT TATGTCAAAG AGGCGTGCTG GCCTGGGGGG GGGAGGCTGC

    451 GGATGCCTGA TACTGGGGCC TGATACTGAG CCCCAAGGCT CAGTCTCGGT

    501 CTCTGTCTCA AGCTCAAGCC AATTCCTTCC GGGGAACCCA ACCACCTCCG

    551 GATTTTTTCC GAAAGTATCC CCGAACGTCT ATGGATTATC CATGTATACA

    601 CAGAACAGGG AGTGAGTGAG TGAGTGCGAA AAACGAAAAA AAATACAGTA

    651 AAACATAAAC CAGAGATAGC AGGGAAAAGA GCCGTGGTGC GGCGCACTGC

    701 GCGCCGCCCT GGGGACGGCG CCTCTCTCTA GTTCCCCCAG AAAAAAGAGT

    751 CACGTGTACA CAGCCGCAGC CGCAGCCGCA GCCGCAGTAT CTCCGTGTCA

    801 CATAGATTGG ACTGAACTGG ACTAGACTAG ACTAGACTAG AGAGTAGACG

    851 AGAATAGACG AGACTAGACG CTCTGGCGTT TCAGATAACA CCAACACTAT

    901 CTATGTTATC ATTACACACA CGATACGTAA TACGTTGGGG CTCCAGCGGT

    951 CAAGGTTGGG GGTGTGGCCC ACATACGTAA CGTCTCGCCC TACACCATAC

   1001 ACGGCATTTT TGTCTGCCTG CCGGCTTTGG CTTGCGCTTT GGTACTTGGT

   1051 ATTTTTTCCT CTTTCTTTTT GTTTCCACCT TCAACAGACA TCTACGCTTT

   1101 TACAGTTCAA GACATTGAAA TTTCAAGACT AGAACTAGAA TTAGAAATTG

   1151 GAAATGAAAT TGGAATTATA ATAGATATTA GAAATAGATA GATATTAGAA

   1201 TAGAGATAGA TATTCGAGTA ATAGAAAGGA CAAAAGTCAG GAAGAAGAAA

   1251 ACTTAGGGCG AGCGAAGCTG CCGTATTAAT CTATTGGAAA ACTGAAATAC

   1301 TAGGTTTCAG AGAAGAAGAA CAAACAAAAA GCGCAATAAC CAGCACTTTA

   1351 TCCAAGTTAC AAGTGTGAGT GAGTGTATAT CTGCAAGCAA GGTGTGATTG

   1401 AGTGAGTGAT CCGCTTGTGA TGGATTCTGT CGCTGATAGC ACCCTTGTTT

   1451 CCAAAGCTGT AGCACAGCCT TCGCCGCATC ATGCTGTGAT AAAGCGTGAA
```

-continued

1501 CATGAGCAGG AAAGAGAAAG ACAAATAGAA GCCGAAGCAG AGGCAGAAGC

1551 AGAGGCAGAA GCAGAAGCAG AAACAGAAAT AGA (CEN/ARS 4)

SEQ ID NO: 13

GAGCTCCTTTCATTTCTGATAAAAGTAAGGTTTCTCTATTTATCTTTTCACCCACATTATCCTTCGAA

GTACGTATACAATATTAGTTCAACGTAAAAACAAAACTTACTGTAAATATGCGTAAAAAAAATCTATT

AAATTCATAGCAGTTTCAAGGAAAGAGAACCATTATGGTCTGGTCACGTGTGTATAAATTATTAATT

TTAACACTATATAATTTATTATTTTTTTATTTTGAAGTTTAGAGTAATTTTAGTAGTATTTTATATTTTA

AATAAATATATTTTAAATTTTTACTTAATATTTTATTATTTTTTAATACAATGTTTTTATTTAAAACAAAA

TTATAAATTAAAATGTTGTTCGAAAGTAAAATATATTTTATGGTTTTTACAAAAATAAATTATTTTTAA

TGTATTTTTTTAATTATATTTTTGTATGTAATTATATCCACAGGTATTATGTTGAATTTAGCTGTTTTA

GTTTACCTGTGTGGTACTATGAGTTTTTTGCCTCTCAAAAGCTATTTTTTAGAACTCTCTCTCCTCTT

AGAAATAGGTGGTGTTGCGGTTGACTTTTAACGATATATCATTTTCAATTTATTTATTTTAAAGTGAC

ATAGAGAGATTCCTTTTAATTTTTTAATTTTTATTTTCAATAATTTTAAAAATGGGGGACTTTTAGATT

GGAACAAAATGAAAAATATCTGTTATACGTGCAACTGAATTTTACTGACCTTAAAGGACTATCTCGA

ACTTGGTTCGGAAATCCTTGAAATGATTGATATTTTGGTGGATTTTCTCTGATTTTCAAACAAGTAGT

ATTTTATTTAATATTTATTATATTTTTTACATTTTTTTATATTTTTTTATTGTTTGGAAGGGAAAGCAAC

AATTACTTTCAAAATATATAAATTAAACTGAAATACTTAATAAGAGACAAATAACATTCAAGAATCAAA

TACTGGGTTATTAATCAAAAGATCTCTCTACATGCACCCAAATTCACTATTTAAATTTACTATACCAC

TGACAGAATATATGAACCCAGATTAAGTAGCCAGAGGCTCTTCCACTATATTGAGTATATAGCCTTA

CATATTTTCTGCGCATAATTTTTCTGGATGTAAAATAAACAAAAATAGTTAGTTTGTAGTTATGAAAAA

AGGCTTTTGGAAAATGCGGAATACGTGTTATTTAAGGTTAATCAACAAAACGCATATCCATAGTGGA

TAGTTGGATAAAACTTCAATTGAT (CEN/ARS 5)

SEQ ID NO: 14

GTCCCAGGTCTCTACAGTGAAAATATTTGCTAATTGCATACAGGAGGCTTAACTATCTCCGTTATAT

AAAAATATGAACACCCTTTTAAAACAGTTGCTGTCAACTAAATTTAGAATGTTTTTTCACTTTGGATG

AACTTTTTAATGTGATCCACTAGTTTTAATTAAATATGATTGGAAAGCACTTTTCCGTAACAAAATGA

TACAAAATGGTCAATGTTAGAAAGTACTG

| gRNA name | gRNA sequence |
|---|---|
| YYKU80_Km.gRNA_1.gg | CACGGGCAGCGCGGGGTCG SEQ ID NO: 15 |
| GAS2_Km.gRNA_0.gg | GAATCCCCCAGACCACACT SEQ ID NO: 16 |
| LEU2_Km.gRNA_0.gg | GCAGTTCCCTTGGCGTACT SEQ ID NO: 17 |
| YYKU80_Km.gRNA_0.gg | GGCCGCGGGCAACAGCCCG SEQ ID NO: 18 |
| NDT80_Km.gRNA_0.gg | GTCCGCCCAGCACAGCGCA SEQ ID NO: 19 |
| GAL80_Km.gRNA_0.gg | GCCCGGCTCAAAACCGCCC SEQ ID NO: 20 |

*K. marxianus* gRNA entry vector sequence

SEQ ID NO: 21

TCGCGCGTTTCGGTGATGACGGTGAAAACCTCTGACACATGCAGCTCCCGGAGACGGTCACAG

CTTGTCTGTAAGCGGATGCCGGGAGCAGACAAGCCCGTCAGGGCGCGTCAGCGGGTGTTGGCG

GGTGTCGGGGCTGGCTTAACTATGCGGCATCAGAGCAGATTGTACTGAGAGTGCAAATACACA

-continued

TCATCGTCCTACAAGTTCATCAAAGTGTTGGACAGACAACTATACCAGCATGGATCTCTTGTA

TCGGTTCTTTTCTCCCGCTCTCTCGCAATAACAATGAACACTGGGTCAATCATAGCCTACACA

GGTGAACAGAGTAGCGTTTATACAGGGTTTATACGGTGATTCCTACGGCAAAAATTTTTCATT

TCTAAAAAAAAAAAGAAAAATTTTTCTTTCCAACGCTAGAAGGAAAAGAAAAATCTAATTAAA

TTGATTTGGTGATTTTCTGAGAGTTCCCTTTTTCATATATCGAATTTTGAATATAAAAGGAGA

TCGAAAAAATTTTTCTATTCAATCTGTTTTCTGGTTTTATTTGATAGTTTTTTTGTGTATTAT

TATTATGGATTAGTACTGGTTTATATGGGTTTTTCTGTATAACTTCTTTTTATTTTAGTTTGT

TTAATCTTATTTTGAGTTACATTATAGTTCCCTAACTGCAAGAGAAGTAACATTAAAAATGAC

CACTCTTGACGACACGGCTTACCGGTACCGCACCAGTGTCCCGGGGGACGCCGAGGCCATCGA

GGCACTGGATGGGTCCTTCACCACCGACACCGTCTTCCGCGTCACCGCCACCGGGGACGGCTT

CACCCTGCGGGAGGTGCCGGTGGACCCGCCCCTGACCAAGGTGTTCCCCGACGACGAATCGGA

CGACGAATCGGACGCCGGGGAGGACGGCGACCCGGACTCCCGGACGTTCGTCGCGTACGGGGA

CGACGGCGACCTGGCGGGCTTCGTGGTCGTCTCGTACTCCGGCTGGAACCGCCGGCTGACCGT

CGAGGACATCGAGGTCGCCCCGGAGCACCGGGGGCACGGGGTCGGGCGCGCGTTGATGGGGCT

CGCGACGGAGTTCGCCCGCGAGCGGGGCGCCGGGCACCTCTGGCTGGAGGTCACCAACGTCAA

CGCACCGGCGATCCACGCGTACCGGCGGATGGGGTTCACCCTCTGCGGCCTGGACACCGCCCT

GTACGACGGCACCGCCTCGGACGGCGAGCAGGCGCTCTACATGAGCATGCCCTGCCCCTGAGT

TTAACTTGATACTACTAGATTTTTTCTCTTCATTTATAAAATTTTTGGTTATAATTGAAGCTT

TAGAAGTATGAAAAAATCCTTTTTTTTCATTCTTTGCAACCAAAATAAGAAGCTTCTTTTATT

CATTGAAATGATGAATATAAACCTAACAAAAGAAAAACAGTCGAATATCAAACATTAAAAAAA

AATAAAAGAGGTTATCTGTTTTCCCATTTAGTTGGAGTTTGCATTTTCTAATAGATAGAACTC

TCAATTAATGTGGATTTAGTTTCTCTGTTCGTTTTTTTTTGTTTTGTTCTCACTGTATTTACA

TTTCTATTTAGTATTTAGTTATTCATATAATCTTAACTTGCGGTGTGAAATACCGCACAGATG

CGTAAGGAGAAAATACCGCATCAGGAAATTGTAAGCGTTAATATTTTGTTAAAATTCGCGTTA

AATTTTTGTTAAATCAGCTCATTTTTTAACCAATAGGCCGAAATCGGCAAAATCCCTTATAAA

TCAAAAGAATAGACCGAGATAGGGTTGAGTGTTGTTCCAGTTTGGAACAAGAGTCCACTATTA

AAGAACGTGGACTCCAACGTCAAAGGGCGAAAAACCGTCTATCAGGGCGATGGCCCACTACGT

GAACCATCACCCTAATCAAGTTTTTTGGGGTCGAGGTGCCGTAAAGCACTAAATCGGAACCCT

AAAGGGAGCCCCCGATTTAGAGCTTGACGGGGAAAGCCTCTTTGAAAAGATAATGTATGATTA

TGCTTTCACTCATATTTATACAGAAACTTGATGTTTTCTTTCGAGTATATACAAGGTGATTAC

ATGTACGTTTGAAGTACAACTCTAGATTTTGTAGTGCCCTCTTGGGCTAGCGGTAAAGGTGCG

CATTTTTTCACACCCTACAATGTTCTGTTCAAAAGATTTTGGTCAAACGCTGTAGAAGTGAAA

GTTGGTGCGCATGTTTCGGCGTTCGAAACTTCTCCGCAGTGAAAGATAAATGATCGCAGTTCC

CTTGGCGTACTCGTTTTAGAGCTAGAAATAGCAAGTTAAAATAAGGCTAGTCCGTTATCAACT

TGAAAAAGTGGCACCGAGTCGGTGGTGCTTTTTTTGTTTTTTATGTCTCAGCTTTTGTTCCCT

TTAGTGAGGGTTAATTGCGCGCTTGGCGTAATCATGGTCATAGCTGTTTCCTGTGTGAAATTG

TTATCCGCTCACAATTCCACACAACATAGGAGCCGGAAGCATAAAGTGTAAAGCCTGGGGTGC

CTAATGAGTGAGGTAACTCACATTAATTGCGTTGCGCTCACTGCCCGCTTTCCAGTCGGGAAA

CCTGTCGTGCCAGGGATCCGATCTCCTTTCATTTCTGATAAAAGTAAGGCTTCTCTATTTACC

TTTTAACCTACATATTCATAGTTGGAAGTTATCCTTCTAAGTACGTATACAATATTAATTCAA

-continued

CGTAAAAACAAAACTTACTGTAAATATGTGTAAAAAAAATCTATTAAATTCATGGCAGTTTCA

AGAAAAGAAAACTATTATGGTCTGGTCACGTGTATACAAATTATTAATTTTAAAACTATATAA

TTTATTATTTTTTTATTTTGAAGTTTAGAGTAATTTTAGTAGTATTTTATATTTTAAATAAAT

ATGCTTTAAATTTTTACTTAATATTTTATTATTTTTAAATACAACGTTTTTATTTAAAACAAA

ATTATAAGTTAAAAAGTTGTTCCGAAAGTAAAATATATTTTATGGGTTTTACAAAAATAAATT

ATTTTTAATGTATTTTTTTAATTATATTTTTGTATGTAATTATATCCACAGGTATTATGTTGA

ATTTAGCTGTTTTAGTTTACCTGTGTGGTACTATGATTTTTTTAGAACTCTCCTCTTAGAAAT

AGGTGGTGTTGCGGTTGACTTTTAACGATATATCATTTTCAATTTATTTATTTTAAAGTGACA

TAGAGAGATTCCTTTTAATTTTTTAATTTTTATTTTCAATAATTTTAAAAATGGGGGACTTTT

AAATTGGAACAAAATGAAAAATATCTGTTATACGTGCAACTGAATTTTACTGACCTTAAAGGA

CTATCTCGAACTTGGTTCGGAAATCCTTGAAATGATTGATATTTTGGTGGATTTTCTCTGATT

TTCAAACAAGTAGTATTTTATTTAATATTTATTATATTTTTTACATTTTTTTATATTTTTTTA

TTGTTTGGAAGGTAAAGCAACAATTACTTTCAAAATATATAAATCAAACTGAAATACTTAATA

AGAGACAAATAACATTCAAGAATCAAATACTGGGTTATTAATCAAAAGATCTCTCTACATGCG

CCCAAATTCACTATTTAAATTTACTATACCACTGACAGAATATATGAACCCAGATTAAGTAGC

CAGAGGCTCTTCCACTATATTGAGTATATAGCCTTACATATTTTCTGCGCATAATTTACTGAT

GTAAAATAAACAAAAATAGTTAGTTTGTAGTTATGAAAAAAGGCTTTTGGAAAATGCGAAATA

CGTGTTATTTAAGGTTAATCAACAAAACGCATATCCATAGTGGATAGTTGGATAAAACTTCAA

TTGATGCGGCCGCCTGCATTAATGAATCGGCCAACGCGCGGGGAGAGGCGGTTTGCGTATTGG

GCGCTCTTCCGCTTCCTCGCTCACTGACTCGCTGCGCTCGGTCGTTCGGCTGCGGCGAGCGGT

ATCAGCTCACTCAAAGGCGGTAATACGGTTATCCACAGAATCAGGGGATAACGCAGGAAAGAA

CATGTGAGCAAAAGGCCAGCAAAAGGCCAGGAACCGTAAAAAGGCCGCGTTGCTGGCGTTTTT

CCATAGGCTCCGCCCCCCTGACGAGCATCACAAAAATCGACGCTCAAGTCAGAGGTGGCGAAA

CCCGACAGGACTATAAAGATACCAGGCGTTTCCCCCTGGAAGCTCCCTCGTGCGCTCTCCTGT

TCCGACCCTGCCGCTTACCGGATACCTGTCCGCCTTTCTCCCTTCGGGAAGCGTGGCGCTTTC

TCATAGCTCACGCTGTAGGTATCTCAGTTCGGTGTAGGTCGTTCGCTCCAAGCTGGGCTGTGT

GCACGAACCCCCCGTTCAGCCCGACCGCTGCGCCTTATCCGGTAACTATCGTCTTGAGTCCAA

CCCGGTAAGACACGACTTATCGCCACTGGCAGCAGCCACTGGTAACAGGATTAGCAGAGCGAG

GTATGTAGGCGGTGCTACAGAGTTCTTGAAGTGGTGGCCTAACTACGGCTACACTAGAAGGAC

AGTATTTGGTATCTGCGCTCTGCTGAAGCCAGTTACCTTCGGAAAAAGAGTTGGTAGCTCTTG

ATCCGGCAAACAAACCACCGCTGGTAGCGGTGGTTTTTTTGTTTGCAAGCAGCAGATTACGCG

CAGAAAAAAAGGATCTCAAGAAGATCCTTTGATCTTTTCTACGGGGTCTGACGCTCAGTGGAA

CGAAAACTCACGTTAAGGGATTTTGGTCATGAGATTATCAAAAAGGATCTTCACCTAGATCCT

TTTAAATTAAAAATGAAGTTTTAAATCAATCTAAAGTATATATGAGTAAACTTGGTCTGACAG

TTACCAATGCTTAATCAGTGAGGCACCTATCTCAGCGATCTGTCTATTTCGTTCATCCATAGT

TGCCTGACTCCCCGTCGTGTAGATAACTACGATACGGGAGGGCTTACCATCTGGCCCCAGTGC

TGCAATGATACCGCGAGACCCACGCTCACCGGCTCCAGATTTATCAGCAATAAACCAGCCAGC

CGGAAGGGCCGAGCGCAGAAGTGGTCCTGCAACTTTATCCGCCTCCATCCAGTCTATTAATTG

TTGCCGGGAAGCTAGAGTAAGTAGTTCGCCAGTTAATAGTTTGCGCAACGTTGTTGCCATTGC

TACAGGCATCGTGGTGTCACGCTCGTCGTTTGGTATGGCTTCATTCAGCTCCGGTTCCCAACG

ATCAAGGCGAGTTACATGATCCCCCATGTTGTGCAAAAAAGCGGTTAGCTCCTTCGGTCCTCC

GATCGTTGTCAGAAGTAAGTTGGCCGCAGTGTTATCACTCATGGTTATGGCAGCACTGCATAA

TTCTCTTACTGTCATGCCATCCGTAAGATGCTTTTCTGTGACTGGTGAGTACTCAACCAAGTC

ATTCTGAGAATAGTGTATGCGGCGACCGAGTTGCTCTTGCCCGGCGTCAATACGGGATAATAC

CGCGCCACATAGCAGAACTTTAAAAGTGCTCATCATTGGAAAACGTTCTTCGGGGCGAAAACT

CTCAAGGATCTTACCGCTGTTGAGATCCAGTTCGATGTAACCCACTCGTGCACCCAACTGATC

TTCAGCATCTTTTACTTTCACCAGCGTTTCTGGGTGAGCAAAAACAGGAAGGCAAAATGCCGC

AAAAAAGGGAATAAGGGCGACACGGAAATGTTGAATACTCATACTCTTCCTTTTTCAATATTA

TTGAAGCATTTATCAGGGTTATTGTCTCATGAGCGGATACATATTTGAATGTATTTAGAAAAA

TAAACAAATAGGGGTTCCGCGCACATTTCCCCGAAAAGTGCCACCTGAACGAAGCATCTGTGC

TTCATTTTGTAGAACAAAAATGCAACGCGAGAGCGCTAATTTTTCAAACAAAGAATCTGAGCT

GCATTTTTACAGAACAGAAATGCAACGCGAAAGCGCTATTTTACCAACGAAGAATCTGTGCTT

CATTTTTGTAAAACAAAAATGCAACGCGAGAGCGCTAATTTTTCAAACAAAGAATCTGAGCTG

CATTTTTACAGAACAGAAATGCAACGCGAGAGCGCTATTTTACCAACAAAGAATCTATACTTC

TTTTTTGTTCTACAAAAATGCATCCCGAGAGCGCTATTTTTCTAACAAAGCATCTTAGATTAC

TTTTTTTCTCCTTTGTGCGCTCTATAATGCAGTCTCTTGATAACTTTTTGCACTGTAGGTCCG

TTAAGGTTAGAAGAAGGCTACTTTGGTGTCTATTTTCTCTTCCATAAAAAAAGCCTGACTCCA

CTTCCCGCGTTTACTGATTACTAGCGAAGCTGCGGGTGCATTTTTTCAAGATAAAGGCATCCC

CGATTATATTCTATACCGATGTGGATTGCGCATACTTTGTGAACAGAAAGTGATAGCGTTGAT

GATTCTTCATTGGTCAGAAAATTATGAACGGTTTCTTCTATTTTGTCTCTATATACTACGTAT

AGGAAATGTTTACATTTTCGTATTGTTTTCGATTCACTCTATGAATAGTTCTTACTACAATTT

TTTTGTCTAAAGAGTAATACTAGAGATAAACATAAAAAATGTAGAGGTCGAGTTTAGATGCAA

GTTCAAGGAGCGAAAGGTGGATGGGTAGGTTATATAGGGATATAGCACAGAGATATATAGCAA

AGAGATACTTTTGAGCAATGTTTGTGGAAGCGGTATTCGCAATATTTTAGTAGCTCGTTACAG

TCCGGTGCGTTTTTGGTTTTTTGAAAGTGCGTCTTCAGAGCGCTTTTGGTTTTCAAAAGCGCT

CTGAAGTTCCTATACTTTCTAGAGAATAGGAACTTCGGAATAGGAACTTCAAAGCGTTTCCGA

AAACGAGCGCTTCCGAAAATGCAACGCGAGCTGCGCACATACAGCTCACTGTTCACGTCGCAC

CTATATCTGCGTGTTGCCTGTATATATATATACATGAGAAGAACGGCATAGTGCGTGTTTATG

CTTAAATGCGTACTTATATGCGTCTATTTATGTAGGATGAAAGGTAGTCTAGTACCTCCTGTG

ATATTATCCCATTCCATGCGGGGTATCGTATGCTTCCTTCAGCACTACCCTTTAGCTGTTCTA

TATGCTGCCACTCCTCAATTGGATTAGTCTCATCCTTCAATGCTATCATTTCCTTTGATATTG

GATCATATTAAGAAACCATTATTATCATGACATTAACCTATAAAAATAGGCGTATCACGAGGC

CCTTTCGTC

*K. marxianus* f-CphI plasmid sequence

SEQ ID NO: 22

TCGCGCGTTTCGGTGATGACGGTGAAAACCTCTGACACATGCAGCTCCCGGAGACGGTCACAG

CTTGTCTGTAAGCGGATGCCGGGAGCAGACAAGCCCGTCAGGGCGCGTCAGCGGGTGTTGGCG

GGTGTCGGGGCTGGCTTAACTATGCGGCATCAGAGCAGATTGTACTGAGAGTGCAAATACACA

TCATCGTCCTACAAGTTCATCAAAGTGTTGGACAGACAACTATACCAGCATGGATCTCTTGTA

TCGGTTCTTTTCTCCCGCTCTCTCGCAATAACAATGAACACTGGGTCAATCATAGCCTACACA

-continued

GGTGAACAGAGTAGCGTTTATACAGGGTTTATACGGTGATTCCTACGGCAAAAATTTTTCATT

TCTAAAAAAAAAAAGAAAAATTTTTCTTTCCAACGCTAGAAGGAAAAGAAAAATCTAATTAAA

TTGATTTGGTGATTTTCTGAGAGTTCCCTTTTTCATATATCGAATTTTGAATATAAAAGGAGA

TCGAAAAAATTTTTCTATTCAATCTGTTTTCTGGTTTTATTTGATAGTTTTTTTGTGTATTAT

TATTATGGATTAGTACTGGTTTATATGGGTTTTTCTGTATAACTTCTTTTTATTTTAGTTTGT

TTAATCTTATTTTGAGTTACATTATAGTTCCCTAACTGCAAGAGAAGTAACATTAAAAATGGG

TAAGGAAAAGACTCACGTTTCGAGGCCGCGATTAAATTCCAACATGGATGCTGATTTATATGG

GTATAAATGGGCTCGCGATAATGTCGGGCAATCAGGTGCGACAATCTATCGATTGTATGGGAA

GCCCGATGCGCCAGAGTTGTTTCTGAAACATGGCAAAGGTAGCGTTGCCAATGATGTTACAGA

TGAGATGGTCAGACTAAACTGGCTGACGGAATTTATGCCTCTTCCGACCATCAAGCATTTTAT

CCGTACTCCTGATGATGCATGGTTACTCACCACTGCGATCCCCGGCAAAACAGCATTCCAGGT

ATTAGAAGAATATCCTGATTCAGGTGAAAATATTGTTGATGCGCTGGCAGTGTTCCTGCGCCG

GTTGCATTCGATTCCTGTTTGTAATTGTCCTTTTAACAGCGATCGCGTATTTCGTCTCGCTCA

GGCGCAATCACGAATGAATAACGGTTTGGTTGATGCGAGTGATTTTGATGACGAGCGTAATGG

CTGGCCTGTTGAACAAGTCTGGAAAGAAATGCATAAGCTTTTGCCATTCTCACCGGATTCAGT

CGTCACTCATGGTGATTTCTCACTTGATAACCTTATTTTTGACGAGGGGAAATTAATAGGTTG

TATTGATGTTGGACGAGTCGGAATCGCAGACCGATACCAGGATCTTGCCATCCTATGGAACTG

CCTCGGTGAGTTTTCTCCTTCATTACAGAAACGGCTTTTTCAAAAATATGGTATTGATAATCC

TGATATGAATAAATTGCAGTTTCATTTGATGCTCGATGAGTTTTTCTAAGTTTAACTTGATAC

TACTAGATTTTTTCTCTTCATTTATAAAATTTTTGGTTATAATTGAAGCTTTAGAAGTATGAA

AAAATCCTTTTTTTTCATTCTTTGCAACCAAAATAAGAAGCTTCTTTTATTCATTGAAATGAT

GAATATAAACCTAACAAAAGAAAAAGACTCGAATATCAAACATTAAAAAAAAATAAAAGAGGT

TATCTGTTTTCCCATTTAGTTGGAGTTTGCATTTTCTAATAGATAGAACTCTCAATTAATGTG

GATTTAGTTTCTCTGTTCGTTTTTTTTTGTTTTGTTCTCACTGTATTTACATTTCTATTTAGT

ATTTAGTTATTCATATAATCTTAACTTGCGGTGTGAAATACCGCACAGATGCGTAAGGAGAAA

ATACCGCATCAGGAAATTGTAAGCGTTAATATTTTGTTAAAATTCGCGTTAAATTTTTGTTAA

ATCAGCTCATTTTTTAACCAATAGGCCGAAATCGGCAAAATCCCTTATAAATCAAAAGAATAG

ACCGAGATAGGGTTGAGTGTTGTTCCAGTTTGGAACAAGAGTCCACTATTAAAGAACGTGGAC

TCCAACGTCAAAGGGCGAAAAACCGTCTATCAGGGCGATGGCCCACTACGTGAACCATCACCC

TAATCAAGTTTTTTGGGGTCGAGGTGCCGTAAAGCACTAAATCGGAACCCTAAAGGGAGCCCC

CGATTTAGAGCTTGACGGGGAAAGCCGGCGAACGTGGCGAGAAAGGAAGGGAAGAAAGCGAAA

GGAGCGGGCGCTAGGGCGCTGGCAAGTGTAGCGGTCACGCTGCGCGTAACCACCACACCCGCC

GCGCTTAATGCGCCGCTACAGGGCGCGTCGCGCCATTCGCCATTCAGGCTGCGCAACTGTTGG

GAAGGGCGATCGGTGCGGGCCTCTTCGCTATTACGCCAGCTGGCGAAAGGGGGATGTGCTGCA

AGGCGATTAAGTTGGGTAACGCCAGGGTTTTCCCAGTCACGACGTTGTAAAACGACGGCCAGT

GAGCGCGCGTAATACGACTCACTATAGGGCGGAATAAAAAACACGCTTTTTCAGTTCGAGTTT

ATCATTATCAATACTGCCATTTCAAAGAATACGTAAATAATTAATAGTAGTGATTTTCCTAAC

TTTATTTAGTCAAAAAATTAGCCTTTTAATTCTGCTGTAACCCGTACATGCCCAAAATAGGGG

GCGGGTTACACAGAATATATAACATCGTAGGTGTCTGGGTGAACAGTTTATTCCTGGCATCCA

-continued

CTAAATATAATGGAGCCCGCTTTTTAAGCTGGCATCCAGAAAAAAAAAGAATCCCAGCACCAA

AATATTGTTTTCTTCACCAACCATCAGTTCATAGGTCCATTCTCTTAGCGCAACTACAGAGAA

CAGGGGCACAAACAGGCAAAAAACGGGCACAACCTCAATGGAGTGATGCAACCTGCCTGGAGT

AAATGATGACACAAGGCAATTGACCCACGCATGTATCTATCTCATTTTCTTACACCTTCTATT

ACCTTCTGCTCTCTCTGATTTGGAAAAAGCTGAAAAAAAAGGTTGAAACCAGTTCCCTGAAAT

TATTCCCCTACTTGACTAATAAGTATATAAAGACGGTAGGTATTGATTGTAATTCTGTAAATC

TATTTCTTAAACTTCTTAAATTCTACTTTTATAGTTAGTCTTTTTTTTAGTTTTAAAACACCA

AGAACTTAGTTTCGAATAAACACACATAAACAAACAAAATGACTAAGTTGTATTCTGACTTGT

ACAGGACCTGCATGACATGCGGAGAAGAAAAATTGTCAACCGAGTTCTACGTCAGGAACAAGA

AGACCGGAGTTAGACATTCATCATGCAAAGAGTGTGACAAGGTCAGGGTCAAATCAAGACACA

AGGAGAACCCTGAAAGGACCAAAAACAACGACTTGAAGAGATTGTACGGAATCACCTTGGACG

AGCATACCCAAATGTATGAGGAACAAAATGGTGTATGTGCAATTTGCAAGGGAGAAGGAGATG

GAAAGTGGAAGAAATTGTGTGTTGACCATGATCACGAAACAGGAAAGGTCAGGCAGTTGTTGT

GTAGGAACTGCAATATGATGTTGGGTCAGGTCAACGACAACGTTAACTTATTATCAGAAATGA

TAAAGTATTTGAAAAGATATCAGTAAAACCTGCAGGCCGCGAGCGCCGATTAAGTGAATTTAC

TTTAAATCTTGCATTTAAATAAATTTTCTTTTTATAGCTTTATGACTTAGTTTCAATTTATAT

ACTATTTTAATGACATTTTCGATTCATTGATTGAAAGCTTTGTGTTTTTTCTTGATGCGCTAT

TGCATTGTTCTTGTCTTTTTCGCCACATGTAATATCTGTAGTAGATACCTGATACATTGTGGA

TGCTGAGTGAAATTTTAGTTAATAATGGAGGCGCTCTTAATAATTTTGGGGATATTGGCTTAA

CGCGATCGCCGACGCCGCCGATGGGGGATCCACTAGTTCTAGAGCGGCCGCCACCGCGGTGGA

GCTCCAGCTTTTGTTCCCTTTAGTGAGGGTTAATTGCGCGCTTGGCGTAATCATGGTCATAGC

TGTTTCCTGTGTGAAATTGTTATCCGCTCACAATTCCACACAACATAGGAGCCGGAAGCATAA

AGTGTAAAGCCTGGGGTGCCTAATGAGTGAGGTAACTCACATTAATTGCGTTGCGCTCACTGC

CCGCTTTCCAGTCGGGAAACCTGTCGTGCCAGCTGCATTAATGAATCGGCCAACGCGCGGGGA

GAGGCGGTTTGCGTATTGGGCGCTCTTCCGCTTCCTCGCTCACTGACTCGCTGCGCTCGGTCG

TTCGGCTGCGGCGAGCGGTATCAGCTCACTCAAAGGCGGTAATACGGTTATCCACAGAATCAG

GGGATAACGCAGGAAAGAACATGTGAGCAAAAGGCCAGCAAAAGGCCAGGAACCGTAAAAAGG

CCGCGTTGCTGGCGTTTTTCCATAGGCTCCGCCCCCCTGACGAGCATCACAAAAATCGACGCT

CAAGTCAGAGGTGGCGAAACCCGACAGGACTATAAAGATACCAGGCGTTTCCCCCTGGAAGCT

CCCTCGTGCGCTCTCCTGTTCCGACCCTGCCGCTTACCGGATACCTGTCCGCCTTTCTCCCTT

CGGGAAGCGTGGCGCTTTCTCATAGCTCACGCTGTAGGTATCTCAGTTCGGTGTAGGTCGTTC

GCTCCAAGCTGGGCTGTGTGCACGAACCCCCCGTTCAGCCCGACCGCTGCGCCTTATCCGGTA

ACTATCGTCTTGAGTCCAACCCGGTAAGACACGACTTATCGCCACTGGCAGCAGCCACTGGTA

ACAGGATTAGCAGAGCGAGGTATGTAGGCGGTGCTACAGAGTTCTTGAAGTGGTGGCCTAACT

ACGGCTACACTAGAAGGACAGTATTTGGTATCTGCGCTCTGCTGAAGCCAGTTACCTTCGGAA

AAAGAGTTGGTAGCTCTTGATCCGGCAAACAAACCACCGCTGGTAGCGGTGGTTTTTTTGTTT

GCAAGCAGCAGATTACGCGCAGAAAAAAAGGATCTCAAGAAGATCCTTTGATCTTTTCTACGG

GGTCTGACGCTCAGTGGAACGAAAACTCACGTTAAGGGATTTTGGTCATGAGATTATCAAAAA

GGATCTTCACCTAGATCCTTTTAAATTAAAAATGAAGTTTTAAATCAATCTAAAGTATATATG

AGTAAACTTGGTCTGACAGTTACCAATGCTTAATCAGTGAGGCACCTATCTCAGCGATCTGTC

-continued

TATTTCGTTCATCCATAGTTGCCTGACTCCCCGTCGTGTAGATAACTACGATACGGGAGGGCT

TACCATCTGGCCCCAGTGCTGCAATGATACCGCGAGACCCACGCTCACCGGCTCCAGATTTAT

CAGCAATAAACCAGCCAGCCGGAAGGGCCGAGCGCAGAAGTGGTCCTGCAACTTTATCCGCCT

CCATCCAGTCTATTAATTGTTGCCGGGAAGCTAGAGTAAGTAGTTCGCCAGTTAATAGTTTGC

GCAACGTTGTTGCCATTGCTACAGGCATCGTGGTGTCACGCTCGTCGTTTGGTATGGCTTCAT

TCAGCTCCGGTTCCCAACGATCAAGGCGAGTTACATGATCCCCCATGTTGTGCAAAAAAGCGG

TTAGCTCCTTCGGTCCTCCGATCGTTGTCAGAAGTAAGTTGGCCGCAGTGTTATCACTCATGG

TTATGGCAGCACTGCATAATTCTCTTACTGTCATGCCATCCGTAAGATGCTTTTCTGTGACTG

GTGAGTACTCAACCAAGTCATTCTGAGAATAGTGTATGCGGCGACCGAGTTGCTCTTGCCCGG

CGTCAATACGGGATAATACCGCGCCACATAGCAGAACTTTAAAAGTGCTCATCATTGGAAAAC

GTTCTTCGGGGCGAAAACTCTCAAGGATCTTACCGCTGTTGAGATCCAGTTCGATGTAACCCA

CTCGTGCACCCAACTGATCTTCAGCATCTTTTACTTTCACCAGCGTTTCTGGGTGAGCAAAAA

CAGGAAGGCAAAATGCCGCAAAAAAGGGAATAAGGGCGACACGGAAATGTTGAATACTCATAC

TCTTCCTTTTTCAATATTATTGAAGCATTTATCAGGGTTATTGTCTCATGAGCGGATACATAT

TTGAATGTATTTAGAAAAATAAACAAATAGGGGTTCCGCGCACATTTCCCCGAAAAGTGCCAC

CTGGGCTCGAGGATCTCCTTTCATTTCTGATAAAAGTAAGGCTTCTCTATTTACCTTTTAACC

TACATATTCATAGTTGGAAGTTATCCTTCTAAGTACGTATACAATATTAATTCAACGTAAAAA

CAAAACTTACTGTAAATATGTGTAAAAAAAATCTATTAAATTCATGGCAGTTTCAAGAAAAGA

AAACTATTATGGTCTGGTCACGTGTATACAAATTATTAATTTTAAAACTATATAATTTATTAT

TTTTTTATTTTGAAGTTTAGAGTAATTTTAGTAGTATTTTATATTTTAAATAAATATGCTTTA

AATTTTTACTTAATATTTTATTATTTTTAAATACAACGTTTTTATTTAAAACAAAATTATAAG

TTAAAAAGTTGTTCCGAAAGTAAAATATATTTTATGGGTTTTACAAAAATAAATTATTTTTAA

TGTATTTTTTTAATTATATTTTTGTATGTAATTATATCCACAGGTATTATGTTGAATTTAGCT

GTTTTAGTTTACCTGTGTGGTACTATGATTTTTTTAGAACTCTCCTCTTAGAAATAGGTGGTG

TTGCGGTTGACTTTTAACGATATATCATTTTCAATTTATTTATTTTAAAGTGACATAGAGAGA

TTCCTTTTAATTTTTTAATTTTTATTTTCAATAATTTTAAAAATGGGGGACTTTTAAATTGGA

ACAAAATGAAAAATATCTGTTATACGTGCAACTGAATTTTACTGACCTTAAAGGACTATCTCG

AACTTGGTTCGGAAATCCTTGAAATGATTGATATTTTGGTGGATTTTCTCTGATTTTCAAACA

AGTAGTATTTTATTTAATATTTATTATATTTTTTACATTTTTTTATATTTTTTTATTGTTTGG

AAGGTAAAGCAACAATTACTTTCAAAATATATAAATCAAACTGAAATACTTAATAAGAGACAA

ATAACATTCAAGAATCAAATACTGGGTTATTAATCAAAAGATCTCTCTACATGCGCCCAAATT

CACTATTTAAATTTACTATACCACTGACAGAATATATGAACCCAGATTAAGTAGCCAGAGGCT

CTTCCACTATATTGAGTATATAGCCTTACATATTTTCTGCGCATAATTTACTGATGTAAAATA

AACAAAAATAGTTAGTTTGTAGTTATGAAAAAAGGCTTTTGGAAAATGCGAAATACGTGTTAT

TTAAGGTTAATCAACAAAACGCATATCCATAGTGGATAGTTGGATAAAACTTCAATTGATGAA

TTC yYKU70::pTEF1 > Sp.Cas9 Sequence (SEQ ID NO: 23)

GACGGCACGGCCACGCGTTTAAACCGCCGTTATAGATGATCTTTATGACTATCACATAAATTTTGTAAC

CTTTTTCATTGGTTCAAAGGTTAACCATTTGATGACACGACATTCGCAGATATCTTAAGGTGGGGATC

-continued

AAAAGTTAATGACACTAAAAATTGGTTATATTCTCATGGTCCAAATACAAAACCCATAAATGCATCGAC

TATTAAGTCTAAGGTCAAAAGGACAAAGGAAATAAATAGAGTGAAATTTCGCTGTCCTTTAATATTAG

ACGAAAGAGCAGACTTTGTTGTTTCTGTTAGTGGATACACAATTATATCTCATGAGATTCCTGCATCGA

AATACAAGCTTATATATGATAATGGTACGGTCAAACAAGAAGCGTACTCCCGTCGTGAATATCTTGAT

GCGGAAACTGGAGAAGTGGTACCAAATGACGAACTTGCAAAAACCTTTTCATTTGGAGATGAAATAA

TTGAGTTGTCTGAGGAAGAGAACTCACAAATTCAAAACATATACGGAAATTATGACTCATTTTTGAAG

CTAATAGGATTTAGATCTACCGAGGAATGCTTATGTTTTTACAATAATATCGACGCTCGTCCAACGCCG

GCGGACCTcgaatccttacatcacacccaatcccccacaagtgatcccccacacaccatagcttcaaaatgtttctactcctttttta ctcttccagattttctcggactccgcgcatcgccgtaccacttcaaaacacccaagcacagcatactaaatttcccctctttcttcctcta gggtgtcgttaattacccgtactaaaggtttggaaaagaaaaaagagaccgcctcgtttctttttcttcgtcgaaaaaggcaataaaaa tttttatcacgtttctttttcttgaaaatttttttttttgatttttttctctttcgatgacctcccattgatatttaagttaataaacggtcttcaa tttctcaagtttcagtttcatttttcttgttctattacaactttttttacttcttgctcattagaaagaaagcatagcaaACCTCCCGCG

ACCTCCAAAATCGAACTACCTTCACAATGGATAAGAAATACTCTATCGGTTTGGATATTGGTACTAACT

CCGTTGGTTGGGCCGTTATCACTGATGAATACAAGGTTCCATCTAAGAAGTTCAAAGTTTTGGGTAAC

ACTGATAGACACTCTATCAAGAAGAACTTGATTGGTGCTTTGTTATTTGACTCTGGTGAAACCGCTGAG

GCTACCCGTTTAAAAAGAACTGCTAGACGTAGATACACCCGTCGTAAAAACAGAATCTGTTATTTGCA

AGAGATCTTCTCCAACGAAATGGCTAAGGTTGACGACTCTTTTTTCCATAGATTAGAAGAATCTTTCTT

AGTTGAAGAAGATAAGAAGCACGAACGTCATCCAATCTTCGGTAACATTGTCGACGAAGTTGCTTACC

ATGAAAAGTACCCAACTATCTATCACTTGAGAAAGAAATTGGTTGATTCTACTGACAAAGCCGACTTG

AGATTGATCTACTTGGCTTTAGCTCATATGATCAAATTCCGTGGTCATTTTTTAATTGAAGGTGATTTGA

ACCCAGACAACTCTGACGTTGATAAATTGTTCATCCAATTGGTTCAAACCTATAACCAATTGTTTGAAG

AAAACCCAATTAACGCTTCTGGTGTTGATGCTAAGGCTATCTTGTCTGCTAGATTGTCTAAATCTAGAA

GATTGGAAAACTTAATTGCTCAATTGCCAGGTGAAAAAAAAAACGGTTTGTTCGGTAATTTGATTGCT

TTATCCTTGGGTTTGACCCCAAATTTCAAGTCCAACTTTGATTTGGCTGAAGATGCCAAGTTGCAATTG

TCTAAGGATACTTACGATGATGATTTAGATAACTTATTGGCTCAAATTGGTGATCAATACGCTGATTTG

TTTTTAGCTGCCAAGAATTTGTCCGACGCCATTTTGTTGTCTGACATCTTGAGAGTCAACACTGAAATT

ACCAAGGCCCCTTTGTCTGCTTCTATGATTAAGAGATATGACGAACACCACCAAGACTTGACCTTGTTG

AAGGCTTTGGTTAGACAACAATTACCTGAAAAGTATAAGGAAATTTTTTTCGACCAATCTAAGAACGG

TTACGCTGGTTACATTGACGGTGGTGCCTCTCAAGAAGAATTCTACAAATTCATCAAACCAATCTTGGA

AAAGATGGACGGTACTGAAGAATTGTTAGTTAAATTGAACAGAGAAGACTTGTTGAGAAAACAAAGA

ACCTTTGACAACGGTTCCATTCCTCACCAAATCCACTTGGGTGAGTTACACGCTATTTTGAGAAGACAA

GAAGATTTCTACCCATTCTTAAAGGACAACCGTGAAAAGATTGAAAAGATTTTGACCTTCAGAATTCCA

TACTACGTCGGTCCTTTGGCTCGTGGTAACTCCAGATTCGCCTGGATGACTAGAAAGTCCGAAGAAAC

TATTACTCCATGGAACTTCGAAGAAGTCGTTGACAAGGGTGCTTCTGCTCAATCCTTTATCGAAAGAAT

GACCAACTTCGACAAAAACTTGCCAAACGAAAAAGTCTTGCCAAAGCACTCTTTGTTGTATGAATACTT

TACTGTTTATAATGAATTGACTAAAGTTAAGTACGTTACTGAAGGTATGAGAAAACCAGCTTTTTTATC

TGGTGAACAAAAAAAAAGCTATCGTCGATTTGTTGTTCAAAACTAACCGTAAAGTTACCGTCAAGCAAT

TGAAGGAAGATTACTTCAAGAAGATTGAATGTTTTGACTCCGTCGAAATCTCCGGTGTTGAAGACAGA

TTCAATGCTTCTTTGGGTACTTACCACGACTTGTTGAAAATTATCAAGGACAAGGATTTCTTAGATAAC

GAAGAAAACGAAGACATTTTGGAAGATATTGTCTTGACTTTGACTTTGTTCGAAGATAGAGAAATGAT

TGAAGAAAGATTGAAGACTTATGCTCATTTGTTCGACGATAAGGTCATGAAGCAATTAAAGAGAAGA

CGTTACACTGGTTGGGGTAGATTGTCTAGAAAATTGATTAACGGTATCCGTGATAAACAATCTGGTAA

GACCATCTTGGATTTCTTAAAGTCTGATGGTTTTGCCAACAGAAACTTCATGCAATTGATCCACGACGA

CTCTTTGACTTTCAAGGAGGACATTCAAAAGGCTCAAGTTTCTGGTCAAGGTGACTCTTTGCATGAACA

CATTGCCAACTTGGCTGGTTCTCCAGCTATTAAGAAGGGTATCTTGCAAACTGTTAAGGTTGTTGATGA

ATTAGTTAAGGTCATGGGTAGACACAAGCCAGAAAACATCGTCATCGAAATGGCTAGAGAAAACCAA

ACTACTCAAAAGGGTCAAAAGAATTCTAGAGAAAGAATGAAGAGAATTGAGGAAGGTATTAAGGAA

TTAGGTTCCCAAATTTTGAAGGAACATCCAGTCGAAAACACTCAATTGCAAAACGAAAAATTGTACTT

GTACTACTTACAAAACGGTAGAGATATGTATGTCGACCAAGAGTTGGACATCAACAGATTGTCCGACT

ACGATGTTGATCACATCGTTCCACAATCCTTCTTAAAGGACGACTCTATCGACAACAAGGTCTTAACCA

GATCCGACAAAAACAGAGGTAAGTCTGACAACGTTCCATCCGAAGAAGTTGTTAAAAAGATGAAGAA

CTACTGGAGACAATTGTTGAACGCCAAATTGATCACTCAAAGAAAGTTCGATAATTTGACCAAGGCTG

AAAGAGGTGGTTTGTCTGAATTGGATAAGGCTGGTTTTATTAAAAGACAATTGGTTGAGACTAGACAA

ATCACCAAGCATGTCGCTCAAATTTTAGATTCCAGAATGAACACTAAATACGACGAAAACGATAAGTT

AATTAGAGAAGTTAAGGTTATTACCTTGAAGTCTAAGTTGGTTTCTGATTTCAGAAAGGACTTCCAATT

TTACAAGGTCAGAGAAATTAACAACTACCATCACGCTCATGATGCTTACTTGAACGCCGTTGTTGGTAC

CGCTTTGATTAAAAAGTACCCAAAGTTGGAATCCGAATTTGTCTACGGTGACTACAAGGTCTACGATG

TCAGAAAAATGATCGCTAAGTCCGAACAAGAGATTGGTAAGGCTACTGCCAAGTACTTCTTTTACTCT

AACATCATGAACTTTTTCAAGACTGAAATCACTTTAGCTAACGGTGAAATTCGTAAGAGACCATTGATT

GAAACCAACGGTGAGACTGGTGAAATCGTTTGGGATAAGGGTCGTGATTTCGCTACTGTTAGAAAGG

TCTTATCTATGCCACAAGTTAACATCGTCAAGAAAACCGAAGTTCAAACTGGTGGTTTTTCTAAGGAAT

CTATCTTGCCAAAAAGAAACTCTGATAAATTGATTGCTAGAAAGAAGGATTGGGACCCAAAGAAGTAC

GGTGGTTTCGATTCCCCAACCGTCGCTTACTCCGTCTTGGTTGTCGCTAAAGTTGAAAAGGGTAAGTCC

AAGAAATTGAAGTCTGTTAAGGAATTGTTGGGTATCACTATCATGGAAAGATCTTCCTTCGAAAAGAA

CCCAATCGATTTTTTAGAGGCCAAGGGTTATAAGGAAGTTAAAAAGGACTTAATTATTAAGTTGCCAA

AGTACTCTTTGTTCGAATTAGAAAACGGTAGAAAAAGAATGTTGGCCTCTGCTGGTGAGTTGCAAAAA

GGTAACGAATTGGCCTTGCCATCTAAGTATGTTAACTTTTTGTACTTGGCCTCTCATTACGAGAAGTTG

AAGGGTTCCCCAGAAGATAACGAACAAAAGCAATTGTTCGTCGAACAACACAAACATTACTTGGATGA

AATTATCGAACAAATCTCCGAGTTTTCCAAACGTGTTATCTTGGCTGACGCCAATTTGGATAAGGTTTT

GTCTGCTTATAATAAGCATAGAGATAAGCCAATTAGAGAACAAGCCGAGAACATCATTCACTTGTTCA

CTTTGACTAATTTAGGTGCTCCAGCTGCCTTCAAATATTTCGACACCACCATTGATAGAAAGAGATACA

CCTCCACTAAGGAAGTCTTGGATGCCACCTTGATTCACCAATCTATCACTGGTTTGTACGAAACTAGAA

TCGATTTGTCTCAATTAGGTGGTGATTCCCGTGCCGACCCAAAGAAGAAGAGAAAGGTCTAAACAGG

CCCCTTTTCCTTTGTCGATATCATGTAATTAGTTATGTCACGCTTACATTCACGCCCTCCCCCCACATCCG

CTCTAACCGAAAAGGAAGGAGTTAGACAACCTGAAGTCTAGGTCCCTATTTATTTTTTTATAGTTATGT

TAGTATTAAGAACGTTATTTATATTTCAAATTTTTCTTTTTTTTCTGTACAAACGCGTGTACGCATGTAAC

ATTATACTGAAAACCTTGCTTGAGAAGGTTTTGGCATCCCCGCGTGCTTGGCCGGCCGTTTAATCAGC

GCCCAGAGACTAGCACTGAATGATCAACGGGTAGTTCACACGATGCACGAGCGCAACGCTCACAATG

ACAGTCTGGACATCAATAGTCACACTACAGAAGGTGATCTCTCAACTTCAGCAGACCATAGCGTGTAA

-continued

TAAATGCATAATTATTTTTCTCTAAAAAAAACTCAGCTGAAATTTTATATAAGTACTACATTTTATATAC

ATATTACATACTGAACAATAAGCGCGTTTGACATTTTAATTTTCGAAGACCGCGAATCCTTACATCACA

CCCAGTCCCCCAATAGTTCCCCCACACACCATGCTTCAAAAACGCACTGTACTCCTTTTTACTCTTCCGG

ATTTTCTCGGACTCTCCGCATCGCCGCACGAGCCAAGCCACACCCACACACCTCATACCATGTTTCCCCT

CTTTGACTCTTTCGTGCGGCTCCATTACCCGCATGAAACTGTATAAAAGTAACAAAAGACTATTTCGTT

TCTTTTTCTTTGTCGGAAAAGGCAAAAAAAAAAAATTTTTATCACATTTCTTTTTCTTGAAAATTTTTTTTG

GGATTTTTTCTCTTTCGATGACCTCCCATTGATATTTAAGTTAATAAAAGGTCTCCCGTTTTCCAAGTTTT

AATTTGTTCCTCTTGTTTAGTCATTCTTCTTCTCAGCATTGGTCAATTAGAAAGAGAGCATAGCAAACTG

ATCTAAGTTTTAATTACCATATGAAAAAGCCTGAACTCACCGCGACGTCTGTCGAGAAGTTTCTGATCG

AAAAGTTCGACAGCGTCTCCGACCTGATGCAGCTCTCGGAGGGCGAAGAATCTCGTGCTTTCAGCTTC

GATGTAGGAGGGCGTGGATATGTCCTGCGGGTAAATAGCTGCGCCGATGGTTTCTACAAAGATCGTT

ATGTTTATCGGCACTTTGCATCGGCCGCGCTCCCGATTCCGGAAGTGCTTGACATTGGGGAATTCAGC

GAGAGCCTGACCTATTGCATCTCCCGCCGTGCACAGGGTGTCACGTTGCAAGACCTGCCTGAAACCGA

ACTGCCCGCTGTTCTGCAGCCGGTCGCGGAGGCCATGGATGCGATCGCTGCGGCCGATCTTAGCCAG

ACGAGCGGGTTCGGCCCATTCGGACCGCAAGGAATCGGTCAATACACTACATGGCGTGATTTCATATG

CGCGATTGCTGATCCCCATGTGTATCACTGGCAAACTGTGATGGACGACACCGTCAGTGCGTCCGTCG

CGCAGGCTCTCGATGAGCTGATGCTTTGGGCCGAGGACTGCCCCGAAGTCCGGCACCTCGTGCACGC

GGATTTCGGCTCCAACAATGTCCTGACGGACAATGGCCGCATAACAGCGGTCATTGACTGGAGCGAG

GCGATGTTCGGGGATTCCCAATACGAGGTCGCCAACATCTTCTTCTGGAGGCCGTGGTTGGCTTGTAT

GGAGCAGCAGACGCGCTACTTCGAGCGGAGGCATCCGGAGCTTGCAGGATCGCCGCGGCTCCGGGC

GTATATGCTCCGCATTGGTCTTGACCAACTCTATCAGAGCTTGGTTGACGGCAATTTCGATGATGCAGC

TTGGGCGCAGGGTCGATGCGACGCAATCGTCCGATCCGGAGCCGGGACTGTCGGGCGTACACAAATC

GCCCGCAGAAGCGCGGCCGTCTGGACCGATGGCTGTGTAGAAGTACTCGCCGATAGTGGAAACCGAC

GCCCCAGCACTCGTCCGAGGGCAAAGGAATAGGGAAATTGATAAGACTTTTCTAGTTGCATATCTTTT

ATATTTAAATCTTATCTATTAGTTAATTTTTTGTAATTTATCCTTATATAGTCTGGTTATTCTAAAATATC

ATTTCAGTATCTAAAATAGTTCTTTTTTTTTTTGAGTTAGATTTTTATGGGGGAGAGTTGAAGTGTTGAA

TTTTCCCACTTTGCTTCGGGATTGTGGGTCATTCTGTCGATAACTGATATCACATCATCAATAGAACCTC

TTAGATGCACGAGCGCAACGCTCACAATTAATCAGCGCCCAGAGACTAGCACTGAATGATCAACGGG

TAGTTCACACAGGTCCGCCGGCGTTGGACGAGCGCTATCGTATACCATTTATAGATGAAGTCAGGAAA

CTACCTACTTTATCGAGCTATCCAGAACTACTAGAAAGTGATGATTATCAAGTACTCAGTAGAGTCACT

GAAACGCTCGTGAATTTTTTTCAATTTGAAAAATGGGTACAAGCCTTCTGATTACCACAGCCCAGCGCTT

CAAAGACACTTCACGGTACTCAGAGAGTATCTTCTCCAGATTGAAAGTAAGGAAACTAAAGATCAAGA

TGAAGATGACGAAACTCTTCTGAAAGTCAAACAGATTCACGAAAGAATTGCTGCTTCTGCTCAATCAG

ATGATCCTAAACAGCAAAGACTAGTAAAGTATTTGAAACTATGGAATTCATATTACAATCGCTATAATA

ATTTGGAAATTGAATCAAAACCAAAACAGAATAAACGGAGTAAATTTAATATATAATATATAATAATA

TTCTATCGGCGGTTTAAACGCGTGGCCGTGCCGTC

What is claimed:

1. A method of modifying a target site in a *Kluyveromyces* host cell genome, the method comprising:

(a) contacting the host cell, which has reduced non-homologous end joining (NHEJ) activity, wherein the NHEJ activity is reduced by integrating a nucleic acid at YKU70 or YKU80 loci. with:

(i) a first linear nucleic acid capable of homologous recombination with itself or with one or more additional linear nucleic acids contacted with the host cell, whereby homologous recombination in the host cell results in formation of a circular extrachromosomal nucleic acid comprising a coding sequence for a selectable marker and a stability element comprising a centromere sequence (CEN) sequence at least 95% identical to SEQ ID NO: 2 and an autonomously replicating sequence (ARS) consensus sequence at least 90% identical to SEQ ID NO: 3;

(ii) a nuclease capable of cleaving the target site, wherein the nuclease is an RNA guided endonuclease or a meganuclease; and (iii) a donor DNA molecule capable of homologous recombination at the cleaved target site, whereby homologous recombination in the host cell results in integration of the donor linear nucleic acid at the target site; and (b) selecting a transformed host cell expressing the selectable marker.

2. The method of claim 1 , wherein the stability element is at least 95% identical to SEQ ID NO: 1.

3. The method of claim 1, wherein the host cell is *K marxianus*.

4. The method of claim 1, wherein the nuclease is an RNA-guided DNA endonuclease.

5. The method of claim 1, wherein the nucleic acid integrated at YKU70 or YKU80 loci encodes the RNA guided endonuclease.

6. The method of claim 1, wherein the stability element comprises SEQ ID NO: 1.

7. The method of claim 1, wherein CEN sequence comprises SEQ ID NO: 2 and the ARS consensus sequence comprises SEQ ID NO: 3.

* * * * *

SEQUENCE LISTING

<160> NUMBER OF SEQ ID NOS: 28

<210> SEQ ID NO 1
<211> LENGTH: 1260
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 1

```
ggatccgatc tcctttcatt tctgataaaa gtaaggcttc tctatttacc ttttaaccta     60
catattcata gttggaagtt atccttctaa gtacgtatac aatattaatt caacgtaaaa    120
acaaaactta ctgtaaatat gtgtaaaaaa aatctattaa attcatggca gtttcaagaa    180
aagaaaacta ttatggtctg gtcacgtgta tacaaattat taattttaaa actatataat    240
ttattatttt tttattttga agtttagagt aattttagta gtattttata ttttaaataa    300
atatgcttta aatttttact taatatttta ttatttttaa atacaacgtt tttatttaaa    360
acaaaattat aagttaaaaa gttgttccga aagtaaaata tattttatgg gttttacaaa    420
aataaattat ttttaatgta ttttttaat tatattttg tatgtaatta tatccacagg    480
tattatgttg aatttagctg ttttagttta cctgtgtggt actatgattt ttttagaact    540
ctcctcttag aaataggtgg tgttgcggtt gacttttaac gatatatcat tttcaattta    600
tttattttaa agtgacatag agagattcct tttaattttt taatttttat tttcaataat    660
tttaaaaatg ggggactttt aaattggaac aaaatgaaaa atatctgtta tacgtgcaac    720
tgaattttac tgaccttaaa ggactatctc gaacttggtt cggaaatcct tgaaatgatt    780
gatattttgg tggattttct ctgattttca aacaagtagt attttattta atatttatta    840
tatttttac atttttttat attttttat tgtttggaag gtaaagcaac aattactttc    900
aaaatatata aatcaaactg aaatacttaa taagagacaa ataacattca agaatcaaat    960
actgggttat taatcaaaag atctctctac atgcgcccaa attcactatt taaatttact   1020
ataccactga cagaatatat gaacccagat taagtagcca gaggctcttc cactatattg   1080
agtatatagc cttacatatt ttctgcgcat aatttactga tgtaaaataa acaaaaaatag  1140
ttagtttgta gttatgaaaa aaggcttttg gaaaatgcga aatacgtgtt atttaaggtt   1200
aatcaacaaa acgcatatcc atagtggata gttggataaa acttcaattg atgcggccgc   1260
```

<210> SEQ ID NO 2
<211> LENGTH: 193
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 2

```
tcacgtgtat acaaattatt aattttaaaa ctatataatt tattattttt ttattttgaa     60
gtttagagta attttagtag tattttatat tttaaataaa tatgctttaa atttttactt    120
aatattttat tatttttaaa tacaacgttt ttatttaaaa caaaattata agttaaaaag    180
ttgttccgaa agt                                                       193
```

<210> SEQ ID NO 3
<211> LENGTH: 12

<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 3
ttttattgtt tg 12

<210> SEQ ID NO 4
<211> LENGTH: 1205
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 4
gatccaagtc tgaaggttgg tttggcacta actttactct tgttatattc agaattgtat 60
caagtttatt tggtagagtg gagccttttt ttatccgtaa cactttttcc ctgctccatt 120
ttgaaaaacg atttcaggcc atcttggcta ttccgaatga atttggaata tgtttaaatt 180
aataaaaata aaataaaata aaataaaata aaataaaaat taaatcaaat taaattaaat 240
taaattaaat taaattaaat taaataaaaa taaatacaac caatacaaca tggtaatatt 300
cttgcatcgt aatgaatatt aaatatcact ttattaatct catcatgttt tattgttttt 360
gtaaggactt taatatattt gaatcaatat tctttcaatt actagtactt tttttatatg 420
actaaaattg ttacacattg gactgacagt aatttttaaa atttatgatt tattcttact 480
ttatatcttt aaaagtagaa atattatacg gacgctttga atacaattga caacttatct 540
tactagtgtg aatcaaccct atcgatgtag tactcttaaa atacggcctt cttgataaag 600
tgttaaattc atttgggtaa tgatttttcg aaaaccacat tgaatgaacg atctaaataa 660
atataggatg caaaagcatt ttaataattc agaaacaaac aaattattaa acaggagcag 720
ttgaacggta tgttagcgag ttttgtaaag ggtgagtaca tttatagctc tattgaacat 780
aataaataca tataaatagt attttttgac cctctatgaa gatggcttac cagcaactta 840
tgtcttttaa ttcacgtgac tactaaacaa aaaaatatgt tatttaaaaa atatttattt 900
aaatttttaa actattatag attatttgtg aatgcattat tttttaattt attaattaaa 960
agaattgcta tttacttaaa ataagaataa aagcttttta tttttttaaa agaaaaatat 1020
attaaaaaca cttttccgaa agttaaaata attttatatt tatcggtagc tgcaatttat 1080
agacataata ttttatattt tttaaaattt attattattt tgtttgaaat aataacgtcg 1140
gtgagtgttt aaggtgaact aagactgaaa aagtacataa tttttgttaa ttttatgata 1200
tgatc 1205

<210> SEQ ID NO 5
<211> LENGTH: 192
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 5
tcacgtgact actaaacaaa aaaatatgtt atttaaaaaa tatttattta aatttttaaa 60
ctattataga ttatttgtga atgcattatt ttttaattta ttaattaaaa gaattgctat 120
ttacttaaaa taagaataaa agctttttat ttttttaaaa gaaaaatata ttaaaaacac 180
ttttccgaaa gt 192

<210> SEQ ID NO 6
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 6
ttttattgtt tt 12

<210> SEQ ID NO 7
<211> LENGTH: 2411
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 7
aacagattgg tgggtggtca acgcacaagc gatatcccaa cacagtcgga aaaactctcg 60
ttcattccaa aactgattgc ttcagatcac aactccgctg gagaagatga gtccgtcact 120
ttctttcaag atttgattaa cgttgatcgt ttgaaacgtc tcagaaatgt cactggtatg 180
tctatcgaaa tcgtgcttgg gacgcataga gaaatcccac agcaacagca gcagcagcag 240
gagtcacctg tagcagaagg tgttccggtc gcccaggata atggacatgt aaccacgaac 300
gacaatgcgg caaatacttc attggaagaa ccaagttcac ccattgacca ggtttatgga 360
tacctcctac aacagaacat gtctacgttg ccagaagtta cactttcgga aagtgatatc 420
gctatgagct acccgacgga tccagtaccc tcttacagca gcaactttaa caactttgct 480
ctgcctacta ttgccgatga caaacaagaa ttagaacaga tgagattaaa ggagctagaa 540
agtgaacctc ctatctgaac acttaacgag aaatatttat atgtgtgttt ttgtttgtat 600
gtatgtatgt atgtatgcct gtgtatcatt aaatatatta gcggatcccg gagtttttat 660
tatcgtgttc ttttcattat atagtgaacc taaagtgact ttcaattcca aattatggaa 720
agattcctgg cattatgcct tataataatc acttgtttac aacattccat taacaacaca 780
tgtacactca aattccattc cataaaacca aaaaaaacct tattgaattc tccagacctc 840
tctgtcggct tgactttgct tgctcaattc gcgtttggct gaagatcact ccagaaccta 900
ggacgtcatt attgaaatct gatcacgtga ttcgcatatt catatagacg tatatttttc 960
gccacttttc tctcttgaaa aaaagttgtg ctagatgaac tttgagaaca aaacacattg 1020
aaagaaaagt ggaacattat aataattgga aagaatagta gattgggtgg ccaagtggaa 1080
gaatttagta actttagtgg ttagagcttg tttgaacgac caatccagta aactaatcaa 1140
ccattgaaca atgagtattc ctatctttgg agatcaagtt accgaagaga gagcagaaaa 1200
tgctcgtatg agtgcctttg ttggtgccat cgccgttggt gatctagtga aaactacact 1260
aggtccaaaa ggtatggata agttacttca aagtgcatcc aatagctcga gtttggttac 1320
aaacgatggt gctaccattc taaaatctat tcctttggac aaccctgctg ccaaggtgct 1380
tgttaacatc agtaaagtgc aagatgatga agttggtgac ggtacaacaa gtgttactgt 1440

```
tctaagtgca gaattattga gggaagctga aaaacttgtt gaacaaggca gaattcaccc   1500

acaaactatc atcgagggtt acagaattgc ttctgctgct gccctctctg cattggaaaa   1560

ggctgctgtg gacaactcca agaataaaga agaattttac aatgatttga tcagcatcgc   1620

caacacaacg ctatcttcta aaattctatc tcaagataag gctcacttct ctaagttggc   1680

taccgatgct atcttaagat taaagggctc tacgaacttg gaacacattc aaattattaa   1740

gatcattggt ggtaaattat cggattcttt cctagatgaa ggtttcattt tgccaaagag   1800

atttggtacc aaccaaccaa aacgtgttga aaatgcgaag attttgattg ccaacacttc   1860

tctagataca gacaaggtta aaatctttgg taccaaattt aaggtcgact ctacttccaa   1920

gttagctgaa ctagaaaaag ctgagcgtga aaaaatgaag agaaagatag aaaagattgc   1980

acaattcaac attaatacct ttatcaacag acaattaatc tatgactacc ctgaacagat   2040

gtttaccgac atgggtatca actccatcga acatgctgac tttgaaggtg ttgaaagatt   2100

agcacttgtc actggcggtg aggttgtttc tacatttgac aacccagaaa aatgtaagct   2160

aggtgaatgt aagttgatcg aagaagttat aattggtgag gaaatcttta ctaaatttac   2220

cgggtgcaag tctggtgaag cttgtaccat tgttctaagg ggtgccactg agcaagtctt   2280

ggatgaagca gaaagatctc tacatgatgc cctatctgtt ctttcccaaa caacaaagga   2340

gactagaacc gttcttggtg gtggttgtgc agaaatgata atgtctaaag cagttgatac   2400

tgcagctcaa a                                                        2411
```

<210> SEQ ID NO 8
<211> LENGTH: 529
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 8

```
actttcggaa agtgatatcg ctatgagcta cccgacggat ccagtaccct cttacagcag     60

caactttaac aactttgctc tgcctactat tgccgatgac aaacaagaat tagaacagat    120

gagattaaag gagctagaaa gtgaacctcc tatctgaaca cttaacgaga aatatttata    180

tgtgtgtttt tgtttgtatg tatgtatgta tgtatgcctg tgtatcatta aatatattag    240

cggatcccgg agtttttatt atcgtgttct tttcattata tagtgaacct aaagtgactt    300

tcaattccaa attatggaaa gattcctggc attatgcctt ataataatca cttgtttaca    360

acattccatt aacaacacat gtacactcaa attccattcc ataaaaccaa aaaaaacctt    420

attgaattct ccagacctct ctgtcggctt gactttgctt gctcaattcg cgtttggctg    480

aagatcactc cagaacctag gacgtcatta ttgaaatctg atcacgtga                529
```

<210> SEQ ID NO 9
<211> LENGTH: 10
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 9

```
aaacaacaaa                                                            10
```

<210> SEQ ID NO 10
<211> LENGTH: 1583
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 10

```
tcaattacaa agggtggaaa gtgatggggg gaatatcatc tgcacaattt tggctcgctt     60
tatatagtgc cgagattagt agggtctgga taaaaaagcg aaggagaata ggaagaggaa    120
gaaaattttt tttcttcctc tttgaaaggc cgggtaacaa agtctcatcg tcctccaacc    180
tagggctttc ctttccgctt tttttttctt cttctcctcc aaacaagacc caaccataca    240
cacccacaca gacagaagaa aaagtgtaag gatgagcgtt gtgtcgtttt ttttttttt     300
ttttttttt ttggcggaga atgtgtgcac gtgcacagac acacacggga gcggctgtgc    360
ctccgtatac ggcaactgcc acgacaaccg agggcacaga tacacgaggt tatgtcaaag    420
aggcgtgctg gcctgggggg gggaggctgc ggatgcctga tactggggcc tgatactgag    480
ccccaaggct cagtctcggt ctctgtctca agctcaagcc aattccttcc ggggaaccca    540
accacctccg gatttttcc gaaagtatcc ccgaacgtct atggattatc catgtataca    600
cagaacaggg agtgagtgag tgagtgcgaa aaacgaaaaa aaatacagta aaacataaac    660
cagagatagc agggaaaaga gccgtggtgc ggcgcactgc gcgccgccct ggggacggcg    720
cctctctcta gttcccccag aaaaaagagt cacgtgtaca cagccgcagc cgcagccgca    780
gccgcagtat ctccgtgtca catagattgg actgaactgg actagactag actagactag    840
agagtagacg agaatagacg agactagacg ctctggcgtt tcagataaca ccaacactat    900
ctatgttatc attacacaca cgatacgtaa tacgttgggg ctccagcggt caaggttggg    960
ggtgtggccc acatacgtaa cgtctcgccc tacaccatac acggcatttt tgtctgcctg   1020
ccggctttgg cttgcgcttt ggtacttggt attttttcct ctttcttttt gtttccacct   1080
tcaacagaca tctacgcttt tacagttcaa gacattgaaa tttcaagact agaactagaa   1140
ttagaaattg gaaatgaaat tggaattata atagatatta gaaatagata gatattagaa   1200
tagagataga tattcgagta atagaaagga caaaagtcag gaagaagaaa acttagggcg   1260
agcgaagctg ccgtattaat ctattggaaa actgaaatac taggtttcag agaagaagaa   1320
caaacaaaaa gcgcaataac cagcacttta tccaagttac aagtgtgagt gagtgtatat   1380
ctgcaagcaa ggtgtgattg agtgagtgat ccgcttgtga tggattctgt cgctgatagc   1440
acccttgttt ccaaagctgt agcacagcct tcgccgcatc atgctgtgat aaagcgtgaa   1500
catgagcagg aaagagaaag acaaatagaa gccgaagcag aggcagaagc agaggcagaa   1560
gcagaagcag aaacagaaat aga                                           1583
```

<210> SEQ ID NO 11
<211> LENGTH: 200
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 11

```
ttccgaaagt atccccgaac gtctatggat tatccatgta tacacagaac agggagtgag     60
```

tgagtgagtg cgaaaaacga aaaaaaatac agtaaaacat aaaccagaga tagcagggaa 120
aagagccgtg gtgcggcgca ctgcgcgccg ccctggggac ggcgcctctc tctagttccc 180
ccagaaaaaa gagtcacgtg 200

<210> SEQ ID NO 12
<211> LENGTH: 9
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 12 tttttgttt 9

<210> SEQ ID NO 13
<211> LENGTH: 1256
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 13
gagctccttt catttctgat aaaagtaagg tttctctatt tatcttttca cccacattat 60
ccttcgaagt acgtatacaa tattagttca acgtaaaaac aaaacttact gtaaatatgc 120
gtaaaaaaaa tctattaaat tcatagcagt ttcaaggaaa gagaaccatt atggtctggt 180
cacgtgtgta taaattatta attttaacac tatataattt attatttttt tattttgaag 240
tttagagtaa ttttagtagt attttatatt ttaaataaat atattttaaa tttttactta 300
atattttatt atttttttaat acaatgtttt tatttaaaac aaaattataa attaaaatgt 360
tgttccgaaa gtaaaatata ttttatggtt tttacaaaaa taaattattt ttaatgtatt 420
tttttaatta tatttttgta tgtaattata tccacaggta ttatgttgaa tttagctgtt 480
ttagtttacc tgtgtggtac tatgagtttt ttgcctctca aaagctattt tttagaactc 540
tctctcctct tagaaatagg tggtgttgcg gttgactttt aacgatatat cattttcaat 600
ttatttattt taaagtgaca tagagagatt ccttttaatt ttttaatttt tattttcaat 660
aattttaaaa atgggggact tttagattgg aacaaaatga aaaatatctg ttatacgtgc 720
aactgaattt tactgacctt aaaggactat ctcgaacttg gttcggaaat ccttgaaatg 780
attgatattt tggtggattt tctctgattt tcaaacaagt agtattttat ttaatattta 840
ttatattttt tacatttttt tatatttttt tattgtttgg aagggaaagc aacaattact 900
ttcaaaatat ataaattaaa ctgaaatact taataagaga caaataacat tcaagaatca 960
aatactgggt tattaatcaa aagatctctc tacatgcacc caaattcact atttaaattt 1020
actataccac tgacagaata tatgaaccca gattaagtag ccagaggctc ttccactata 1080
ttgagtatat agccttacat attttctgcg cataattttc tggatgtaaa ataaacaaaa 1140
atagttagtt tgtagttatg aaaaaaggct tttggaaaat gcggaatacg tgttatttaa 1200
ggttaatcaa caaaacgcat atccatagtg gatagttgga taaaacttca attgat 1256

<210> SEQ ID NO 14
<211> LENGTH: 232
<212> TYPE: DNA

<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 14
gtcccaggtc tctacagtga aaatatttgc taattgcata caggaggctt aactatctcc 60
gttatataaa aatatgaaca cccttttaaa acagttgctg tcaactaaat ttagaatgtt 120
ttttcacttt ggatgaactt tttaatgtga tccactagtt ttaattaaat atgattggaa 180
agcacttttc cgtaacaaaa tgatacaaaa tggtcaatgt tagaaagtac tg 232

<210> SEQ ID NO 15
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 15
cacgggcagc gcggggtcg 19

<210> SEQ ID NO 16
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 16
gaatccccca gaccacact 19

<210> SEQ ID NO 17
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 17
gcagttccct tggcgtact 19

<210> SEQ ID NO 18
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 18
ggccgcgggc aacagcccg 19

<210> SEQ ID NO 19
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 19
gtccgcccag cacagcgca 19

<210> SEQ ID NO 20
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 20
gcccggctca aaaccgccc 19

<210> SEQ ID NO 21
<211> LENGTH: 7254
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 21
tcgcgcgttt cggtgatgac ggtgaaaacc tctgacacat gcagctcccg gagacggtca 60
cagcttgtct gtaagcggat gccgggagca gacaagcccg tcagggcgcg tcagcgggtg 120
ttggcgggtg tcggggctgg cttaactatg cggcatcaga gcagattgta ctgagagtgc 180
aaatacacat catcgtccta caagttcatc aaagtgttgg acagacaact ataccagcat 240
ggatctcttg tatcggttct tttctcccgc tctctcgcaa taacaatgaa cactgggtca 300
atcatagcct acacaggtga acagagtagc gtttatacag ggtttatacg gtgattccta 360
cggcaaaaat ttttcatttc taaaaaaaaa aagaaaaatt tttctttcca acgctagaag 420
gaaaagaaaa atctaattaa attgatttgg tgattttctg agagttccct ttttcatata 480
tcgaattttg aatataaaag gagatcgaaa aaatttttct attcaatctg ttttctggtt 540
ttatttgata gtttttttgt gtattattat tatggattag tactggttta tatgggtttt 600
tctgtataac ttctttttat tttagtttgt ttaatcttat tttgagttac attatagttc 660
cctaactgca agagaagtaa cattaaaaat gaccactctt gacgacacgg cttaccggta 720
ccgcaccagt gtcccggggg acgccgaggc catcgaggca ctggatgggt ccttcaccac 780
cgacaccgtc ttccgcgtca ccgccaccgg ggacggcttc accctgcggg aggtgccggt 840
ggacccgccc ctgaccaagg tgttccccga cgacgaatcg gacgacgaat cggacgccgg 900
ggaggacggc gacccggact cccggacgtt cgtcgcgtac ggggacgacg gcgacctggc 960
gggcttcgtg gtcgtctcgt actccggctg gaaccgccgg ctgaccgtcg aggacatcga 1020
ggtcgccccg gagcaccggg ggcacggggt cgggcgcgcg ttgatggggc tcgcgacgga 1080
gttcgcccgc gagcggggcg ccgggcacct ctggctggag gtcaccaacg tcaacgcacc 1140
ggcgatccac gcgtaccggc ggatggggtt caccctctgc ggcctggaca ccgccctgta 1200
cgacggcacc gcctcggacg gcgagcaggc gctctacatg agcatgccct gcccctgagt 1260
ttaacttgat actactagat tttttctctt catttataaa atttttggtt ataattgaag 1320
ctttagaagt atgaaaaaat ccttttttttt cattctttgc aaccaaaata agaagcttct 1380

-continued

```
tttattcatt gaaatgatga atataaacct aacaaaagaa aaagactcga atatcaaaca   1440
ttaaaaaaaa ataaaagagg ttatctgttt tcccatttag ttggagtttg cattttctaa   1500
tagatagaac tctcaattaa tgtggattta gtttctctgt tcgttttttt ttgttttgtt   1560
ctcactgtat ttacatttct atttagtatt tagttattca tataatctta acttgcggtg   1620
tgaaataccg cacagatgcg taaggagaaa ataccgcatc aggaaattgt aagcgttaat   1680
attttgttaa aattcgcgtt aaatttttgt taaatcagct cattttttaa ccaataggcc   1740
gaaatcggca aaatccctta taaatcaaaa gaatagaccg agatagggtt gagtgttgtt   1800
ccagtttgga acaagagtcc actattaaag aacgtggact ccaacgtcaa agggcgaaaa   1860
accgtctatc agggcgatgg cccactacgt gaaccatcac cctaatcaag ttttttgggg   1920
tcgaggtgcc gtaaagcact aaatcggaac cctaaaggga gcccccgatt tagagcttga   1980
cggggaaagc ctctttgaaa agataatgta tgattatgct ttcactcata tttatacaga   2040
aacttgatgt tttctttcga gtatatacaa ggtgattaca tgtacgtttg aagtacaact   2100
ctagattttg tagtgccctc ttgggctagc ggtaaaggtg cgcatttttt cacaccctac   2160
aatgttctgt tcaaaagatt ttggtcaaac gctgtagaag tgaaagttgg tgcgcatgtt   2220
tcggcgttcg aaacttctcc gcagtgaaag ataaatgatc gcagttccct tggcgtactc   2280
gttttagagc tagaaatagc aagttaaaat aaggctagtc cgttatcaac ttgaaaaagt   2340
ggcaccgagt cggtggtgct ttttttgttt tttatgtctc agcttttgtt ccctttagtg   2400
agggttaatt gcgcgcttgg cgtaatcatg gtcatagctg tttcctgtgt gaaattgtta   2460
tccgctcaca attccacaca acataggagc cggaagcata aagtgtaaag cctggggtgc   2520
ctaatgagtg aggtaactca cattaattgc gttgcgctca ctgcccgctt tccagtcggg   2580
aaacctgtcg tgccagggat ccgatctcct ttcatttctg ataaaagtaa ggcttctcta   2640
tttacctttt aacctacata ttcatagttg gaagttatcc ttctaagtac gtatacaata   2700
ttaattcaac gtaaaaacaa aacttactgt aaatatgtgt aaaaaaaatc tattaaattc   2760
atggcagttt caagaaaaga aaactattat ggtctggtca cgtgtataca aattattaat   2820
tttaaaacta tataatttat tatttttta ttttgaagtt tagagtaatt ttagtagtat   2880
tttatatttt aaataaatat gctttaaatt tttacttaat attttattat ttttaaatac   2940
aacgttttta tttaaaacaa aattataagt taaaaagttg ttccgaaagt aaaatatatt   3000
ttatgggttt tacaaaaata aattattttt aatgtatttt tttaattata tttttgtatg   3060
taattatatc cacaggtatt atgttgaatt tagctgtttt agtttacctg tgtggtacta   3120
tgattttttt agaactctcc tcttagaaat aggtggtgtt gcggttgact tttaacgata   3180
tatcatttc aatttattta ttttaaagtg acatagagag attcctttta atttttttaat   3240
ttttattttc aataatttta aaaatggggg acttttaaat tggaacaaaa tgaaaaatat   3300
ctgttatacg tgcaactgaa ttttactgac cttaaaggac tatctcgaac ttggttcgga   3360
aatccttgaa atgattgata ttttggtgga ttttctctga ttttcaaaca agtagtattt   3420
tatttaatat ttattatatt ttttacattt ttttatattt ttttattgtt tggaaggtaa   3480
agcaacaatt actttcaaaa tatataaatc aaactgaaat acttaataag agacaaataa   3540
cattcaagaa tcaaatactg ggttattaat caaaagatct ctctacatgc gcccaaattc   3600
actatttaaa tttactatac cactgacaga atatatgaac ccagattaag tagccagagg   3660
ctcttccact atattgagta tatagcctta catattttct gcgcataatt tactgatgta   3720
aaataaacaa aaatagttag tttgtagtta tgaaaaaagg cttttggaaa atgcgaaata   3780
```

-continued

```
cgtgttattt aaggttaatc aacaaaacgc atatccatag tggatagttg gataaaactt   3840
caattgatgc ggccgcctgc attaatgaat cggccaacgc gcggggagag gcggtttgcg   3900
tattgggcgc tcttccgctt cctcgctcac tgactcgctg cgctcggtcg ttcggctgcg   3960
gcgagcggta tcagctcact caaaggcggt aatacggtta tccacagaat caggggataa   4020
cgcaggaaag aacatgtgag caaaaggcca gcaaaaggcc aggaaccgta aaaaggccgc   4080
gttgctggcg tttttccata ggctccgccc ccctgacgag catcacaaaa atcgacgctc   4140
aagtcagagg tggcgaaacc cgacaggact ataaagatac caggcgtttc cccctggaag   4200
ctccctcgtg cgctctcctg ttccgaccct gccgcttacc ggatacctgt ccgcctttct   4260
cccttcggga agcgtggcgc tttctcatag ctcacgctgt aggtatctca gttcggtgta   4320
ggtcgttcgc tccaagctgg gctgtgtgca cgaacccccc gttcagcccg accgctgcgc   4380
cttatccggt aactatcgtc ttgagtccaa cccggtaaga cacgacttat cgccactggc   4440
agcagccact ggtaacagga ttagcagagc gaggtatgta ggcggtgcta cagagttctt   4500
gaagtggtgg cctaactacg gctacactag aaggacagta tttggtatct gcgctctgct   4560
gaagccagtt accttcggaa aaagagttgg tagctcttga tccggcaaac aaaccaccgc   4620
tggtagcggt ggtttttttg tttgcaagca gcagattacg cgcagaaaaa aaggatctca   4680
agaagatcct ttgatctttt ctacggggtc tgacgctcag tggaacgaaa actcacgtta   4740
agggattttg gtcatgagat tatcaaaaag gatcttcacc tagatccttt taaattaaaa   4800
atgaagtttt aaatcaatct aaagtatata tgagtaaact tggtctgaca gttaccaatg   4860
cttaatcagt gaggcaccta tctcagcgat ctgtctattt cgttcatcca tagttgcctg   4920
actccccgtc gtgtagataa ctacgatacg ggagggctta ccatctggcc ccagtgctgc   4980
aatgataccg cgagacccac gctcaccggc tccagattta tcagcaataa accagccagc   5040
cggaagggcc gagcgcagaa gtggtcctgc aactttatcc gcctccatcc agtctattaa   5100
ttgttgccgg gaagctagag taagtagttc gccagttaat agtttgcgca acgttgttgc   5160
cattgctaca ggcatcgtgg tgtcacgctc gtcgtttggt atggcttcat tcagctccgg   5220
ttcccaacga tcaaggcgag ttacatgatc ccccatgttg tgcaaaaaag cggttagctc   5280
cttcggtcct ccgatcgttg tcagaagtaa gttggccgca gtgttatcac tcatggttat   5340
ggcagcactg cataattctc ttactgtcat gccatccgta agatgctttt ctgtgactgg   5400
tgagtactca accaagtcat tctgagaata gtgtatgcgg cgaccgagtt gctcttgccc   5460
ggcgtcaata cgggataata ccgcgccaca tagcagaact ttaaaagtgc tcatcattgg   5520
aaaacgttct tcggggcgaa aactctcaag gatcttaccg ctgttgagat ccagttcgat   5580
gtaacccact cgtgcaccca actgatcttc agcatctttt actttcacca gcgtttctgg   5640
gtgagcaaaa acaggaaggc aaaatgccgc aaaaaaggga ataagggcga cacggaaatg   5700
ttgaatactc atactcttcc tttttcaata ttattgaagc atttatcagg gttattgtct   5760
catgagcgga tacatatttg aatgtattta gaaaaataaa caaatagggg ttccgcgcac   5820
atttccccga aaagtgccac ctgaacgaag catctgtgct tcattttgta gaacaaaaat   5880
gcaacgcgag agcgctaatt tttcaaacaa agaatctgag ctgcattttt acagaacaga   5940
aatgcaacgc gaaagcgcta ttttaccaac gaagaatctg tgcttcattt ttgtaaaaca   6000
aaaatgcaac gcgagagcgc taatttttca aacaaagaat ctgagctgca tttttacaga   6060
acagaaatgc aacgcgagag cgctatttta ccaacaaaga atctatactt ctttttttgtt   6120
```

ctacaaaaat gcatcccgag agcgctattt ttctaacaaa gcatcttaga ttactttttt 6180
tctcctttgt gcgctctata atgcagtctc ttgataactt tttgcactgt aggtccgtta 6240
aggttagaag aaggctactt tggtgtctat tttctcttcc ataaaaaaag cctgactcca 6300
cttcccgcgt ttactgatta ctagcgaagc tgcgggtgca ttttttcaag ataaaggcat 6360
ccccgattat attctatacc gatgtggatt gcgcatactt tgtgaacaga aagtgatagc 6420
gttgatgatt cttcattggt cagaaaatta tgaacggttt cttctatttt gtctctatat 6480
actacgtata ggaaatgttt acattttcgt attgttttcg attcactcta tgaatagttc 6540
ttactacaat ttttttgtct aaagagtaat actagagata aacataaaaa atgtagaggt 6600
cgagtttaga tgcaagttca aggagcgaaa ggtggatggg taggttatat agggatatag 6660
cacagagata tatagcaaag agatactttt gagcaatgtt tgtggaagcg gtattcgcaa 6720
tattttagta gctcgttaca gtccggtgcg tttttggttt tttgaaagtg cgtcttcaga 6780
gcgcttttgg ttttcaaaag cgctctgaag ttcctatact ttctagagaa taggaacttc 6840
ggaataggaa cttcaaagcg tttccgaaaa cgagcgcttc cgaaaatgca acgcgagctg 6900
cgcacataca gctcactgtt cacgtcgcac ctatatctgc gtgttgcctg tatatatata 6960
tacatgagaa gaacggcata gtgcgtgttt atgcttaaat gcgtacttat atgcgtctat 7020
ttatgtagga tgaaaggtag tctagtacct cctgtgatat tatcccattc catgcggggt 7080
atcgtatgct tccttcagca ctacccttta gctgttctat atgctgccac tcctcaattg 7140
gattagtctc atccttcaat gctatcattt cctttgatat tggatcatat taagaaacca 7200
ttattatcat gacattaacc tataaaaata ggcgtatcac gaggcccttt cgtc 7254

<210> SEQ ID NO 22
<211> LENGTH: 7500
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 22
tcgcgcgttt cggtgatgac ggtgaaaacc tctgacacat gcagctcccg gagacggtca 60
cagcttgtct gtaagcggat gccgggagca gacaagcccg tcagggcgcg tcagcgggtg 120
ttggcgggtg tcggggctgg cttaactatg cggcatcaga gcagattgta ctgagagtgc 180
aaatacacat catcgtccta caagttcatc aaagtgttgg acagacaact ataccagcat 240
ggatctcttg tatcggttct tttctcccgc tctctcgcaa taacaatgaa cactgggtca 300
atcatagcct acacaggtga acagagtagc gtttatacag ggtttatacg gtgattccta 360
cggcaaaaat ttttcatttc taaaaaaaaa aagaaaaatt tttctttcca acgctagaag 420
gaaaagaaaa atctaattaa attgatttgg tgattttctg agagttccct ttttcatata 480
tcgaattttg aatataaaag gagatcgaaa aaatttttct attcaatctg ttttctggtt 540
ttatttgata gtttttttgt gtattattat tatggattag tactggttta tatgggtttt 600
tctgtataac ttctttttat tttagtttgt ttaatcttat tttgagttac attatagttc 660
cctaactgca agagaagtaa cattaaaaat gggtaaggaa aagactcacg tttcgaggcc 720
gcgattaaat tccaacatgg atgctgattt atatgggtat aaatgggctc gcgataatgt 780
cgggcaatca ggtgcgacaa tctatcgatt gtatgggaag cccgatgcgc cagagttgtt 840
tctgaaacat ggcaaaggta gcgttgccaa tgatgttaca gatgagatgg tcagactaaa 900

```
ctggctgacg gaatttatgc ctcttccgac catcaagcat tttatccgta ctcctgatga    960
tgcatggtta ctcaccactg cgatccccgg caaaacagca ttccaggtat tagaagaata   1020
tcctgattca ggtgaaaata ttgttgatgc gctggcagtg ttcctgcgcc ggttgcattc   1080
gattcctgtt tgtaattgtc cttttaacag cgatcgcgta tttcgtctcg ctcaggcgca   1140
atcacgaatg aataacggtt tggttgatgc gagtgatttt gatgacgagc gtaatggctg   1200
gcctgttgaa caagtctgga aagaaatgca taagcttttg ccattctcac cggattcagt   1260
cgtcactcat ggtgatttct cacttgataa ccttattttt gacgagggga aattaatagg   1320
ttgtattgat gttggacgag tcggaatcgc agaccgatac caggatcttg ccatcctatg   1380
gaactgcctc ggtgagtttt ctccttcatt acagaaacgg ctttttcaaa aatatggtat   1440
tgataatcct gatatgaata aattgcagtt tcatttgatg ctcgatgagt ttttctaagt   1500
ttaacttgat actactagat tttttctctt catttataaa atttttggtt ataattgaag   1560
ctttagaagt atgaaaaaat cctttttttt cattctttgc aaccaaaata agaagcttct   1620
tttattcatt gaaatgatga atataaacct aacaaaagaa aaagactcga atatcaaaca   1680
ttaaaaaaaa ataaaagagg ttatctgttt tcccatttag ttggagtttg cattttctaa   1740
tagatagaac tctcaattaa tgtggattta gtttctctgt tcgttttttt ttgttttgtt   1800
ctcactgtat ttacatttct atttagtatt tagttattca tataatctta acttgcggtg   1860
tgaaataccg cacagatgcg taaggagaaa ataccgcatc aggaaattgt aagcgttaat   1920
attttgttaa aattcgcgtt aaatttttgt taaatcagct cattttttaa ccaataggcc   1980
gaaatcggca aaatccctta taaatcaaaa gaatagaccg agataggtt gagtgttgtt   2040
ccagtttgga acaagagtcc actattaaag aacgtggact ccaacgtcaa agggcgaaaa   2100
accgtctatc agggcgatgg cccactacgt gaaccatcac cctaatcaag ttttttgggg   2160
tcgaggtgcc gtaaagcact aaatcggaac cctaaaggga gcccccgatt tagagcttga   2220
cggggaaagc cggcgaacgt ggcgagaaag gaagggaaga aagcgaaagg agcgggcgct   2280
agggcgctgg caagtgtagc ggtcacgctg cgcgtaacca ccacacccgc cgcgcttaat   2340
gcgccgctac agggcgcgtc gcgccattcg ccattcaggc tgcgcaactg ttgggaaggg   2400
cgatcggtgc gggcctcttc gctattacgc cagctggcga aagggggatg tgctgcaagg   2460
cgattaagtt gggtaacgcc agggttttcc cagtcacgac gttgtaaaac gacggccagt   2520
gagcgcgcgt aatacgactc actatagggc ggaataaaaa acacgctttt tcagttcgag   2580
tttatcatta tcaatactgc catttcaaag aatacgtaaa taattaatag tagtgatttt   2640
cctaacttta tttagtcaaa aaattagcct tttaattctg ctgtaacccg tacatgccca   2700
aaatagggggg cgggttacac agaatatata acatcgtagg tgtctgggtg aacagtttat   2760
tcctggcatc cactaaatat aatggagccc gctttttaag ctggcatcca gaaaaaaaaa   2820
gaatcccagc accaaaatat tgttttcttc accaaccatc agttcatagg tccattctct   2880
tagcgcaact acagagaaca ggggcacaaa caggcaaaaa acgggcacaa cctcaatgga   2940
gtgatgcaac ctgcctggag taaatgatga cacaaggcaa ttgacccacg catgtatcta   3000
tctcattttc ttacaccttc tattaccttc tgctctctct gatttggaaa aagctgaaaa   3060
aaaaggttga aaccagttcc ctgaaattat tcccctactt gactaataag tatataaaga   3120
cggtaggtat tgattgtaat tctgtaaatc tatttcttaa acttcttaaa ttctactttt   3180
atagttagtc ttttttttag ttttaaaaca ccaagaactt agtttcgaat aaacacacat   3240
```

```
aaacaaacaa aatgactaag ttgtattctg acttgtacag gacctgcatg acatgcggag   3300
aagaaaaatt gtcaaccgag ttctacgtca ggaacaagaa gaccggagtt agacattcat   3360
catgcaaaga gtgtgacaag gtcagggtca aatcaagaca caaggagaac cctgaaagga   3420
ccaaaaacaa cgacttgaag agattgtacg gaatcacctt ggacgagcat acccaaatgt   3480
atgaggaaca aaatggtgta tgtgcaattt gcaagggaga aggagatgga aagtggaaga   3540
aattgtgtgt tgaccatgat cacgaaacag gaaaggtcag gcagttgttg tgtaggaact   3600
gcaatatgat gttgggtcag gtcaacgaca acgttaactt attatcagaa atgataaagt   3660
atttgaaaag atatcagtaa aacctgcagg ccgcgagcgc cgattaagtg aatttacttt   3720
aaatcttgca tttaaataaa ttttcttttt atagctttat gacttagttt caatttatat   3780
actattttaa tgacattttc gattcattga ttgaaagctt tgtgtttttt cttgatgcgc   3840
tattgcattg ttcttgtctt tttcgccaca tgtaatatct gtagtagata cctgatacat   3900
tgtggatgct gagtgaaatt ttagttaata atggaggcgc tcttaataat tttggggata   3960
ttggcttaac gcgatcgccg acgccgccga tgggggatcc actagttcta gagcggccgc   4020
caccgcggtg gagctccagc ttttgttccc tttagtgagg gttaattgcg cgcttggcgt   4080
aatcatggtc atagctgttt cctgtgtgaa attgttatcc gctcacaatt ccacacaaca   4140
taggagccgg aagcataaag tgtaaagcct ggggtgccta atgagtgagg taactcacat   4200
taattgcgtt gcgctcactg cccgctttcc agtcgggaaa cctgtcgtgc cagctgcatt   4260
aatgaatcgg ccaacgcgcg gggagaggcg gtttgcgtat tgggcgctct tccgcttcct   4320
cgctcactga ctcgctgcgc tcggtcgttc ggctgcggcg agcggtatca gctcactcaa   4380
aggcggtaat acggttatcc acagaatcag gggataacgc aggaaagaac atgtgagcaa   4440
aaggccagca aaaggccagg aaccgtaaaa aggccgcgtt gctggcgttt ttccataggc   4500
tccgcccccc tgacgagcat cacaaaaatc gacgctcaag tcagaggtgg cgaaacccga   4560
caggactata aagataccag gcgtttcccc ctggaagctc cctcgtgcgc tctcctgttc   4620
cgaccctgcc gcttaccgga tacctgtccg cctttctccc ttcgggaagc gtggcgcttt   4680
ctcatagctc acgctgtagg tatctcagtt cggtgtaggt cgttcgctcc aagctgggct   4740
gtgtgcacga accccccgtt cagcccgacc gctgcgcctt atccggtaac tatcgtcttg   4800
agtccaaccc ggtaagacac gacttatcgc cactggcagc agccactggt aacaggatta   4860
gcagagcgag gtatgtaggc ggtgctacag agttcttgaa gtggtggcct aactacggct   4920
acactagaag gacagtattt ggtatctgcg ctctgctgaa gccagttacc ttcggaaaaa   4980
gagttggtag ctcttgatcc ggcaaacaaa ccaccgctgg tagcggtggt ttttttgttt   5040
gcaagcagca gattacgcgc agaaaaaaag gatctcaaga agatcctttg atcttttcta   5100
cggggtctga cgctcagtgg aacgaaaact cacgttaagg gattttggtc atgagattat   5160
caaaaaggat cttcacctag atccttttaa attaaaaatg aagttttaaa tcaatctaaa   5220
gtatatatga gtaaacttgg tctgacagtt accaatgctt aatcagtgag gcacctatct   5280
cagcgatctg tctatttcgt tcatccatag ttgcctgact ccccgtcgtg tagataacta   5340
cgatacggga gggcttacca tctggcccca gtgctgcaat gataccgcga gacccacgct   5400
caccggctcc agatttatca gcaataaacc agccagccgg aagggccgag cgcagaagtg   5460
gtcctgcaac tttatccgcc tccatccagt ctattaattg ttgccgggaa gctagagtaa   5520
gtagttcgcc agttaatagt ttgcgcaacg ttgttgccat tgctacaggc atcgtggtgt   5580
cacgctcgtc gtttggtatg gcttcattca gctccggttc ccaacgatca aggcgagtta   5640
```

catgatcccc catgttgtgc aaaaaagcgg ttagctcctt cggtcctccg atcgttgtca 5700
gaagtaagtt ggccgcagtg ttatcactca tggttatggc agcactgcat aattctctta 5760
ctgtcatgcc atccgtaaga tgcttttctg tgactggtga gtactcaacc aagtcattct 5820
gagaatagtg tatgcggcga ccgagttgct cttgcccggc gtcaatacgg gataataccg 5880
cgccacatag cagaacttta aaagtgctca tcattggaaa acgttcttcg gggcgaaaac 5940
tctcaaggat cttaccgctg ttgagatcca gttcgatgta acccactcgt gcacccaact 6000
gatcttcagc atcttttact ttcaccagcg tttctgggtg agcaaaaaca ggaaggcaaa 6060
atgccgcaaa aaagggaata agggcgacac ggaaatgttg aatactcata ctcttccttt 6120
ttcaatatta ttgaagcatt tatcagggtt attgtctcat gagcggatac atatttgaat 6180
gtatttagaa aaataaacaa ataggggttc cgcgcacatt tccccgaaaa gtgccacctg 6240
ggctcgagga tctcctttca tttctgataa aagtaaggct tctctattta ccttttaacc 6300
tacatattca tagttggaag ttatccttct aagtacgtat acaatattaa ttcaacgtaa 6360
aaacaaaact tactgtaaat atgtgtaaaa aaaatctatt aaattcatgg cagtttcaag 6420
aaaagaaaac tattatggtc tggtcacgtg tatacaaatt attaatttta aaactatata 6480
atttattatt tttttatttt gaagtttaga gtaattttag tagtatttta tattttaaat 6540
aaatatgctt taaattttta cttaatattt tattattttt aaatacaacg tttttattta 6600
aaacaaaatt ataagttaaa aagttgttcc gaaagtaaaa tatattttat gggttttaca 6660
aaaataaatt atttttaatg tattttttta attatatttt tgtatgtaat tatatccaca 6720
ggtattatgt tgaatttagc tgttttagtt tacctgtgtg gtactatgat ttttttagaa 6780
ctctcctctt agaaataggt ggtgttgcgg ttgactttta acgatatatc attttcaatt 6840
tatttatttt aaagtgacat agagagattc cttttaattt tttaattttt attttcaata 6900
attttaaaaa tgggggactt ttaaattgga acaaaatgaa aaatatctgt tatacgtgca 6960
actgaatttt actgacctta aaggactatc tcgaacttgg ttcggaaatc cttgaaatga 7020
ttgatatttt ggtggatttt ctctgatttt caaacaagta gtattttatt taatatttat 7080
tatatttttt acattttttt atattttttt attgtttgga aggtaaagca acaattactt 7140
tcaaaatata taaatcaaac tgaaatactt aataagagac aaataacatt caagaatcaa 7200
atactgggtt attaatcaaa agatctctct acatgcgccc aaattcacta tttaaattta 7260
ctataccact gacagaatat atgaacccag attaagtagc cagaggctct tccactatat 7320
tgagtatata gccttacata ttttctgcgc ataatttact gatgtaaaat aaacaaaaat 7380
agttagtttg tagttatgaa aaaaggcttt tggaaaatgc gaaatacgtg ttatttaagg 7440
ttaatcaaca aaacgcatat ccatagtgga tagttggata aaacttcaat tgatgaattc 7500

<210> SEQ ID NO 23
<211> LENGTH: 8090
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 23
gacggcacgg ccacgcgttt aaaccgccgt tatagatgat ctttatgact atcacataaa 60
ttttgtaacc tttttcattg gttcaaaggt taaaccattt gatgacacga cattcgcaga 120

-continued

```
tatcttaagg tggggatcaa aagttaatga cactaaaaat tggttatatt ctcatggtcc    180
aaatacaaaa cccataaatg catcgactat taagtctaag gtcaaaagga caaaggaaat    240
aaatagagtg aaatttcgct gtcctttaat attagacgaa agagcagact ttgttgtttc    300
tgttagtgga tacacaatta tatctcatga gattcctgca tcgaaataca agcttatata    360
tgataatggt acggtcaaac aagaagcgta ctcccgtcgt gaatatcttg atgcggaaac    420
tggagaagtg gtaccaaatg acgaacttgc aaaaaccttt tcatttggag atgaaataat    480
tgagttgtct gaggaagaga actcacaaat tcaaaacata tacggaaatt atgactcatt    540
tttgaagcta ataggattta gatctaccga ggaatgctta tgtttttaca ataatatcga    600
cgctcgtcca acgccggcgg acctcgaatc cttacatcac acccaatccc ccacaagtga    660
tcccccacac accatagctt caaaatgttt ctactccttt tttactcttc cagattttct    720
cggactccgc gcatcgccgt accacttcaa aacacccaag cacagcatac taaatttccc    780
ctctttcttc ctctagggtg tcgttaatta cccgtactaa aggtttggaa aagaaaaaag    840
agaccgcctc gtttcttttt cttcgtcgaa aaaggcaata aaaattttta tcacgtttct    900
ttttcttgaa aatttttttt tttgattttt ttctctttcg atgacctccc attgatattt    960
aagttaataa acggtcttca atttctcaag tttcagtttc atttttcttg ttctattaca   1020
actttttta cttcttgctc attagaaaga aagcatagca aacctcccgc gacctccaaa   1080
atcgaactac cttcacaatg gataagaaat actctatcgg tttggatatt ggtactaact   1140
ccgttggttg ggccgttatc actgatgaat acaaggttcc atctaagaag ttcaaagttt   1200
tgggtaacac tgatagacac tctatcaaga agaacttgat tggtgctttg ttatttgact   1260
ctggtgaaac cgctgaggct acccgtttaa aaagaactgc tagacgtaga tacacccgtc   1320
gtaaaaacag aatctgttat ttgcaagaga tcttctccaa cgaaatggct aaggttgacg   1380
actctttttt ccatagatta gaagaatctt tcttagttga agaagataag aagcacgaac   1440
gtcatccaat cttcggtaac attgtcgacg aagttgctta ccatgaaaag tacccaacta   1500
tctatcactt gagaaagaaa ttggttgatt ctactgacaa agccgacttg agattgatct   1560
acttggcttt agctcatatg atcaaattcc gtggtcattt tttaattgaa ggtgatttga   1620
acccagacaa ctctgacgtt gataaattgt tcatccaatt ggttcaaacc tataaccaat   1680
tgtttgaaga aaacccaatt aacgcttctg gtgttgatgc taaggctatc ttgtctgcta   1740
gattgtctaa atctagaaga ttggaaaact taattgctca attgccaggt gaaaaaaaaa   1800
acggtttgtt cggtaatttg attgctttat ccttgggttt gaccccaaat ttcaagtcca   1860
actttgattt ggctgaagat gccaagttgc aattgtctaa ggatacttac gatgatgatt   1920
tagataactt attggctcaa attggtgatc aatacgctga tttgttttta gctgccaaga   1980
atttgtccga cgccattttg ttgtctgaca tcttgagagt caacactgaa attaccaagg   2040
cccctttgtc tgcttctatg attaagagat atgacgaaca ccaccaagac ttgaccttgt   2100
tgaaggcttt ggttagacaa caattacctg aaaagtataa ggaaattttt ttcgaccaat   2160
ctaagaacgg ttacgctggt tacattgacg gtggtgcctc tcaagaagaa ttctacaaat   2220
tcatcaaacc aatcttggaa aagatggacg gtactgaaga attgttagtt aaattgaaca   2280
gagaagactt gttgagaaaa caaagaacct ttgacaacgg ttccattcct caccaaatcc   2340
acttgggtga gttacacgct attttgagaa gacaagaaga tttctaccca ttcttaaagg   2400
acaaccgtga aaagattgaa aagattttga ccttcagaat tccatactac gtcggtcctt   2460
tggctcgtgg taactccaga ttcgcctgga tgactagaaa gtccgaagaa actattactc   2520
```

```
catggaactt cgaagaagtc gttgacaagg gtgcttctgc tcaatccttt atcgaaagaa   2580
tgaccaactt cgacaaaaac ttgccaaacg aaaaagtctt gccaaagcac tctttgttgt   2640
atgaatactt tactgtttat aatgaattga ctaaagttaa gtacgttact gaaggtatga   2700
gaaaaccagc tttttatct ggtgaacaaa aaaaagctat cgtcgatttg ttgttcaaaa   2760
ctaaccgtaa agttaccgtc aagcaattga aggaagatta cttcaagaag attgaatgtt   2820
ttgactccgt cgaaatctcc ggtgttgaag acagattcaa tgcttctttg ggtacttacc   2880
acgacttgtt gaaaattatc aaggacaagg atttcttaga taacgaagaa aacgaagaca   2940
ttttggaaga tattgtcttg actttgactt tgttcgaaga tagagaaatg attgaagaaa   3000
gattgaagac ttatgctcat ttgttcgacg ataaggtcat gaagcaatta aagagaagac   3060
gttacactgg ttggggtaga ttgtctagaa aattgattaa cggtatccgt gataaacaat   3120
ctggtaagac catcttggat ttcttaaagt ctgatggttt tgccaacaga aacttcatgc   3180
aattgatcca cgacgactct ttgactttca aggaggacat tcaaaaggct caagtttctg   3240
gtcaaggtga ctctttgcat gaacacattg ccaacttggc tggttctcca gctattaaga   3300
agggtatctt gcaaactgtt aaggttgttg atgaattagt taaggtcatg ggtagacaca   3360
agccagaaaa catcgtcatc gaaatggcta gagaaaacca aactactcaa aagggtcaaa   3420
agaattctag agaaagaatg aagagaattg aggaaggtat taaggaatta ggttcccaaa   3480
ttttgaagga acatccagtc gaaaacactc aattgcaaaa cgaaaaattg tacttgtact   3540
acttacaaaa cggtagagat atgtatgtcg accaagagtt ggacatcaac agattgtccg   3600
actacgatgt tgatcacatc gttccacaat ccttcttaaa ggacgactct atcgacaaca   3660
aggtcttaac cagatccgac aaaaacagag gtaagtctga caacgttcca tccgaagaag   3720
ttgttaaaaa gatgaagaac tactggagac aattgttgaa cgccaaattg atcactcaaa   3780
gaaagttcga taatttgacc aaggctgaaa gaggtggttt gtctgaattg gataaggctg   3840
gttttattaa aagacaattg gttgagacta gacaaatcac caagcatgtc gctcaaattt   3900
tagattccag aatgaacact aaatacgacg aaaacgataa gttaattaga gaagttaagg   3960
ttattacctt gaagtctaag ttggtttctg atttcagaaa ggacttccaa ttttacaagg   4020
tcagagaaat taacaactac catcacgctc atgatgctta cttgaacgcc gttgttggta   4080
ccgctttgat taaaaagtac ccaaagttgg aatccgaatt tgtctacggt gactacaagg   4140
tctacgatgt cagaaaaatg atcgctaagt ccgaacaaga gattggtaag gctactgcca   4200
agtacttctt ttactctaac atcatgaact tttcaagac tgaaatcact ttagctaacg   4260
gtgaaattcg taagagacca ttgattgaaa ccaacggtga gactggtgaa atcgtttggg   4320
ataagggtcg tgatttcgct actgttagaa aggtcttatc tatgccacaa gttaacatcg   4380
tcaagaaaac cgaagttcaa actggtggtt tttctaagga atctatcttg ccaaaaagaa   4440
actctgataa attgattgct agaaagaagg attgggaccc aaagaagtac ggtggtttcg   4500
attccccaac cgtcgcttac tccgtcttgg ttgtcgctaa agttgaaaag ggtaagtcca   4560
agaaattgaa gtctgttaag gaattgttgg gtatcactat catggaaaga tcttccttcg   4620
aaaagaaccc aatcgatttt ttagaggcca agggttataa ggaagttaaa aaggacttaa   4680
ttattaagtt gccaaagtac tctttgttcg aattagaaaa cggtagaaaa agaatgttgg   4740
cctctgctgg tgagttgcaa aaaggtaacg aattggcctt gccatctaag tatgttaact   4800
ttttgtactt ggcctctcat tacgagaagt tgaagggttc cccagaagat aacgaacaaa   4860
```

-continued

```
agcaattgtt cgtcgaacaa cacaaacatt acttggatga aattatcgaa caaatctccg   4920
agttttccaa acgtgttatc ttggctgacg ccaatttgga taaggttttg tctgcttata   4980
ataagcatag agataagcca attagagaac aagccgagaa catcattcac ttgttcactt   5040
tgactaattt aggtgctcca gctgccttca aatatttcga caccaccatt gatagaaaga   5100
gatacacctc cactaaggaa gtcttggatg ccaccttgat tcaccaatct atcactggtt   5160
tgtacgaaac tagaatcgat ttgtctcaat taggtggtga ttcccgtgcc gacccaaaga   5220
agaagagaaa ggtctaaaca ggcccctttt cctttgtcga tatcatgtaa ttagttatgt   5280
cacgcttaca ttcacgccct ccccccacat ccgctctaac cgaaaaggaa ggagttagac   5340
aacctgaagt ctaggtccct atttattttt ttatagttat gttagtatta agaacgttat   5400
ttatatttca aatttttctt ttttttctgt acaaacgcgt gtacgcatgt aacattatac   5460
tgaaaacctt gcttgagaag gttttggcat ccccgcgtgc ttggccggcc gtttaatcag   5520
cgcccagaga ctagcactga atgatcaacg ggtagttcac acgatgcacg agcgcaacgc   5580
tcacaatgac agtctggaca tcaatagtca cactacagaa ggtgatctct caacttcagc   5640
agaccatagc gtgtaataaa tgcataatta tttttctcta aaaaaaactc agctgaaatt   5700
ttatataagt actacatttt atatacatat tacatactga acaataagcg cgtttgacat   5760
tttaattttc gaagaccgcg aatccttaca tcacacccag tcccccaata gttcccccac   5820
acaccatgct tcaaaaacgc actgtactcc tttttactct tccggatttt ctcggactct   5880
ccgcatcgcc gcacgagcca agccacaccc acacacctca taccatgttt cccctctttg   5940
actctttcgt gcggctccat tacccgcatg aaactgtata aaagtaacaa aagactattt   6000
cgtttctttt tctttgtcgg aaaaggcaaa aaaaaaaatt tttatcacat ttcttttttct   6060
tgaaaatttt ttttgggatt ttttctcttt cgatgacctc ccattgatat ttaagttaat   6120
aaaaggtctc ccgttttcca agttttaatt tgttcctctt gtttagtcat tcttcttctc   6180
agcattggtc aattagaaag agagcatagc aaactgatct aagttttaat taccatatga   6240
aaaagcctga actcaccgcg acgtctgtcg agaagtttct gatcgaaaag ttcgacagcg   6300
tctccgacct gatgcagctc tcggagggcg aagaatctcg tgctttcagc ttcgatgtag   6360
gagggcgtgg atatgtcctg cgggtaaata gctgcgccga tggtttctac aaagatcgtt   6420
atgtttatcg gcactttgca tcggccgcgc tcccgattcc ggaagtgctt gacattgggg   6480
aattcagcga gagcctgacc tattgcatct cccgccgtgc acagggtgtc acgttgcaag   6540
acctgcctga aaccgaactg cccgctgttc tgcagccggt cgcggaggcc atggatgcga   6600
tcgctgcggc cgatcttagc cagacgagcg ggttcggccc attcggaccg caaggaatcg   6660
gtcaatacac tacatggcgt gatttcatat gcgcgattgc tgatccccat gtgtatcact   6720
ggcaaactgt gatggacgac accgtcagtg cgtccgtcgc gcaggctctc gatgagctga   6780
tgctttgggc cgaggactgc cccgaagtcc ggcacctcgt gcacgcggat ttcggctcca   6840
acaatgtcct gacggacaat ggccgcataa cagcggtcat tgactggagc gaggcgatgt   6900
tcggggattc ccaatacgag gtcgccaaca tcttcttctg gaggccgtgg ttggcttgta   6960
tggagcagca gacgcgctac ttcgagcgga ggcatccgga gcttgcagga tcgccgcggc   7020
tccgggcgta tatgctccgc attggtcttg accaactcta tcagagcttg gttgacggca   7080
atttcgatga tgcagcttgg gcgcagggtc gatgcgacgc aatcgtccga tccggagccg   7140
ggactgtcgg gcgtacacaa atcgcccgca gaagcgcggc cgtctggacc gatggctgtg   7200
tagaagtact cgccgatagt ggaaaccgac gccccagcac tcgtccgagg gcaaaggaat   7260
```

agggaaattg ataagacttt tctagttgca tatcttttat atttaaatct tatctattag 7320
ttaatttttt gtaatttatc cttatatagt ctggttattc taaaatatca tttcagtatc 7380
taaaatagtt cttttttttt ttgagttaga tttttatggg ggagagttga agtgttgaat 7440
tttcccactt tgcttcggga ttgtgggtca ttctgtcgat aactgatatc acatcatcaa 7500
tagaacctct tagatgcacg agcgcaacgc tcacaattaa tcagcgccca gagactagca 7560
ctgaatgatc aacgggtagt tcacacaggt ccgccggcgt tggacgagcg ctatcgtata 7620
ccatttatag atgaagtcag gaaactacct actttatcga gctatccaga actactagaa 7680
agtgatgatt atcaagtact cagtagagtc actgaaacgc tcgtgaattt tttcaatttg 7740
aaaaatgggt acaagccttc tgattaccac agcccagcgc ttcaaagaca cttcacggta 7800
ctcagagagt atcttctcca gattgaaagt aaggaaacta aagatcaaga tgaagatgac 7860
gaaactcttc tgaaagtcaa acagattcac gaaagaattg ctgcttctgc tcaatcagat 7920
gatcctaaac agcaaagact agtaaagtat ttgaaactat ggaattcata ttacaatcgc 7980
tataataatt tggaaattga atcaaaacca aaacagaata aacggagtaa atttaatata 8040
taatatataa taatattcta tcggcggttt aaacgcgtgg ccgtgccgtc 8090

<210> SEQ ID NO 24
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 24
ccttataaat caaaagaata gaccgagata gg 32

<210> SEQ ID NO 25
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 25
tgttgtgtgg aattgtgagc gg 22

<210> SEQ ID NO 26
<211> LENGTH: 35
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 26
gttttagagc tagaaatagc aagttaaaat aaggc 35

<210> SEQ ID NO 27
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:

-continued

```
      Synthetic oligonucleotide"

<400> SEQUENCE: 27

cgatcattta tctttcactg cggag                                          25


<210> SEQ ID NO 28
<211> LENGTH: 9
<212> TYPE: PRT
<213> ORGANISM: Unknown
<220> FEATURE:
<221> NAME/KEY: source
<223> OTHER INFORMATION: /note="Description of Unknown:
      'LAGLIDADG' family motif peptide"

<400> SEQUENCE: 28

Leu Ala Gly Leu Ile Asp Ala Asp Gly
1               5
```